US012012463B2

(12) United States Patent
Ho et al.

(10) Patent No.: US 12,012,463 B2
(45) Date of Patent: Jun. 18, 2024

(54) HIGH AFFINITY MONOCLONAL ANTIBODIES TARGETING GLYPICAN-2 AND USES THEREOF

(71) Applicant: The U.S.A., as represented by the Secretary, Department of Health and Human Services, Bethesda, MD (US)

(72) Inventors: Mitchell Ho, Urbana, MD (US); Nan Li, Laurel, MD (US); Bryan D. Fleming, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 806 days.

(21) Appl. No.: 17/266,419

(22) PCT Filed: Aug. 6, 2019

(86) PCT No.: PCT/US2019/045338
§ 371 (c)(1),
(2) Date: Feb. 5, 2021

(87) PCT Pub. No.: WO2020/033430
PCT Pub. Date: Feb. 13, 2020

(65) Prior Publication Data
US 2021/0292428 A1    Sep. 23, 2021

Related U.S. Application Data

(60) Provisional application No. 62/716,169, filed on Aug. 8, 2018.

(51) Int. Cl.
| *C07K 16/30* | (2006.01) |
| *A61K 47/68* | (2017.01) |
| *A61P 35/00* | (2006.01) |
| *C07K 14/725* | (2006.01) |
| *C12N 15/86* | (2006.01) |
| *G01N 33/574* | (2006.01) |
| *A61K 39/00* | (2006.01) |

(52) U.S. Cl.
CPC .......... *C07K 16/30* (2013.01); *A61K 47/6829* (2017.08); *A61P 35/00* (2018.01); *C07K 14/7051* (2013.01); *C12N 15/86* (2013.01); *G01N 33/5748* (2013.01); *A61K 2039/505* (2013.01)

(58) Field of Classification Search
CPC ................ C07K 16/30; C07K 14/7051; A61K 47/6829; A61K 35/00; A61K 2039/505; C12N 15/86; G01N 33/5748
See application file for complete search history.

(56) References Cited

U.S. PATENT DOCUMENTS 11,066,479 B2 *   7/2021   Ho .......................... C07K 7/08

FOREIGN PATENT DOCUMENTS

| WO | WO 2017/083296 | 5/2017 |
| WO | WO 2018/026533 | 2/2018 |

OTHER PUBLICATIONS

Li et al., CAR T cells targeting tumor-associated exons of glypican 2 regress neuroblastoma in mice; 2021, Cell Reports Medicine, 2, 100297. (Year: 2021).*
Bosse et al., "Identification of GPC2 as an Oncoprotein and Candidate Immunotherapeutic Target in High-Risk Neuroblastoma," Cancer Cell, vol. 32:295-309, 2017.
Bosse et al., "The Antibody-Drug Conjugate D3-GPC2-PBD Potently Eradicates Neuroblastoma Patient-Derived Xenografts," Abstract In: Proceedings of the American Association for Cancer Research Annual Meeting 2018; Apr. 14-18, 2018; Chicago, IL. Philadelphia (PA): AACR; Cancer Res 78(13 Suppl):Abstract 4636, 2018, pp. 1-2 . . . .
Li et al., "Therapeutically Targeting Glypican-2 via Single-Domain Antibody-Based Chimeric Antigen Receptors and Immunotoxins in Neuroblastoma," Proc. Nat. Acad.Sci. USA, vol. 114:E6623-E6631, 2017.
International Search Report and Written Opinion, dated Oct. 31, 2019, for PCT/US2019/045338 (14 pages).

* cited by examiner

Primary Examiner — Daniel E Kolker
Assistant Examiner — James Ryland Melchior
(74) Attorney, Agent, or Firm — Klarquist Sparkman, LLP

(57) ABSTRACT

Monoclonal antibodies that bind glypican-2 (GPC2) with high affinity are described. Immunotoxins and chimeric antigen receptors (CARs) that include the disclosed antibodies or antigen-binding fragments thereof are further described. In some instances, the antibody or antigen-binding fragment is humanized. The disclosed GPC2-specific antibodies and conjugates can be used, for example, for the diagnosis or treatment of GPC2-positive cancers, including neuroblastoma, medulloblastoma and retinoblastoma.

45 Claims, 26 Drawing Sheets
Specification includes a Sequence Listing.

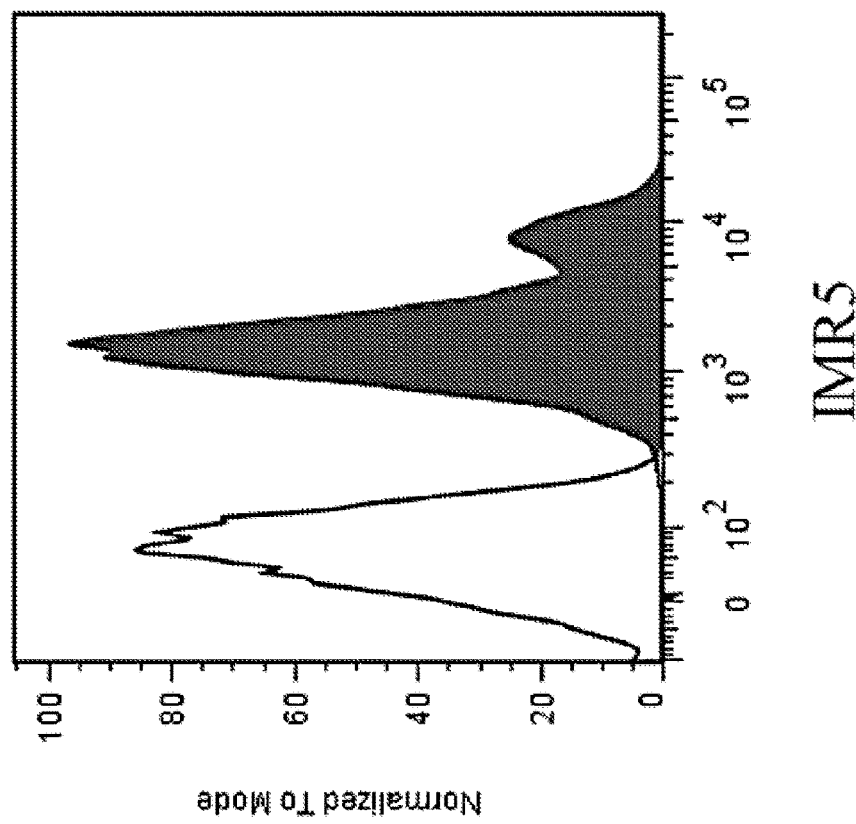
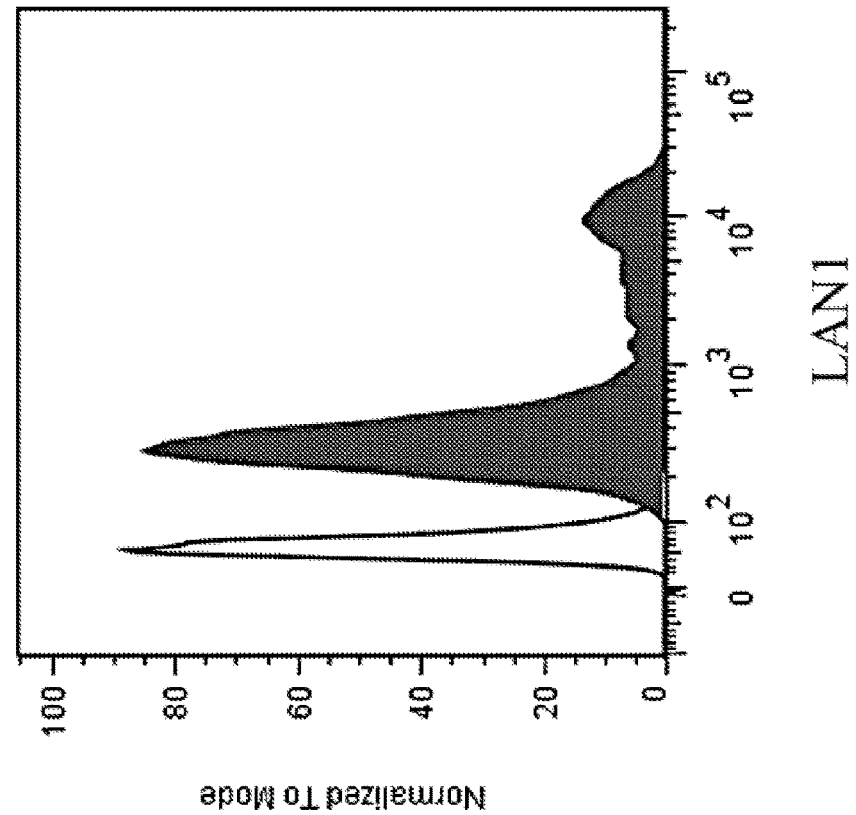
FIG. 2A

FIG. 2B
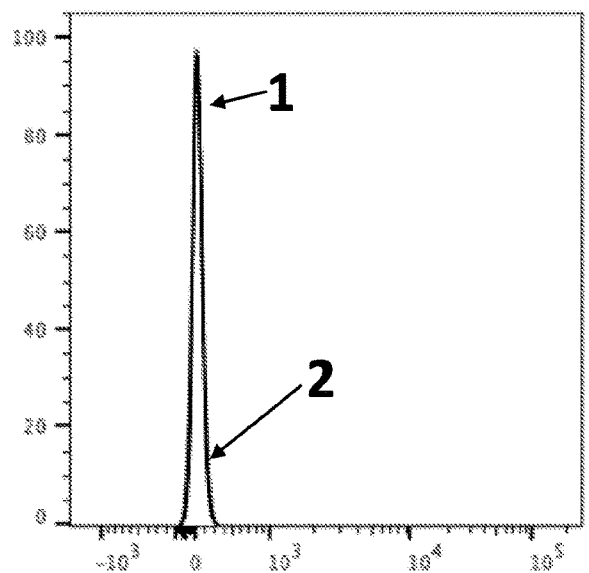
A431
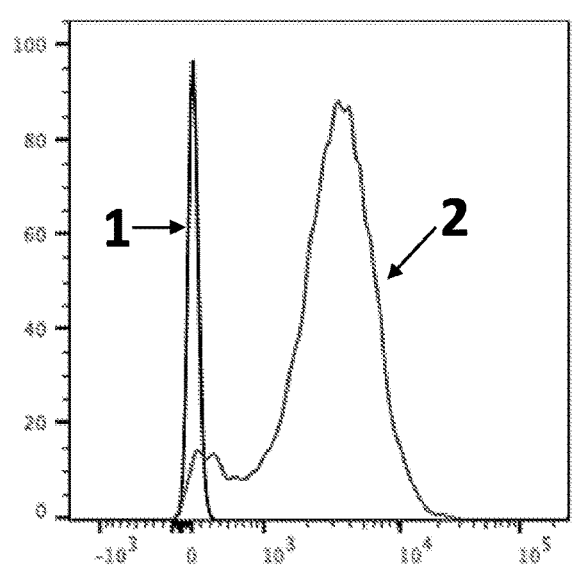
G10 (GPC2 overexpressing -A431 cells)
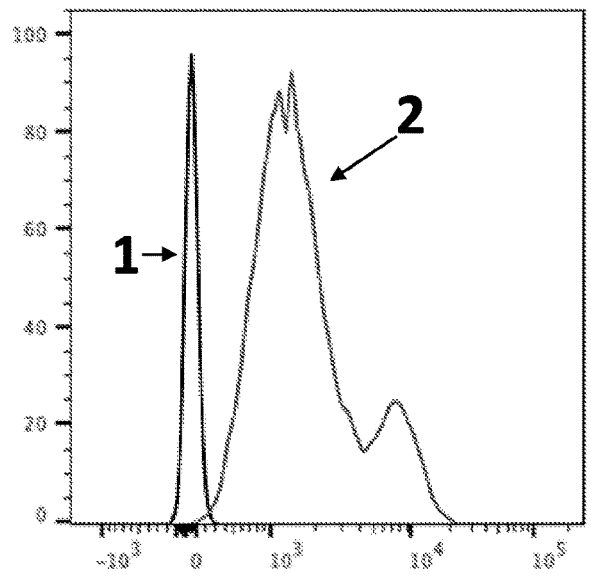
IMR5
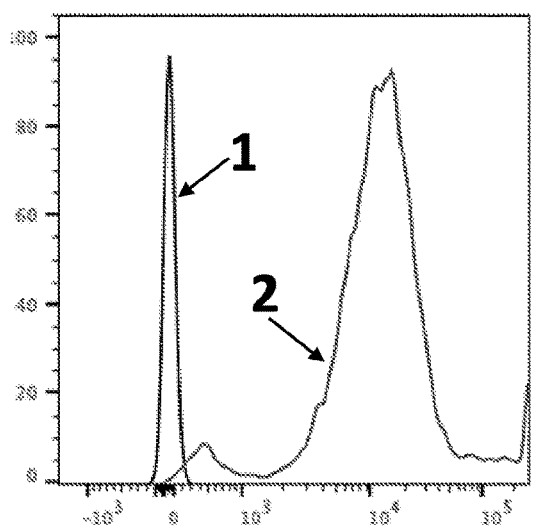
F8 (GPC2 overexpressing -IMR5 cells)

FIG. 8A A431
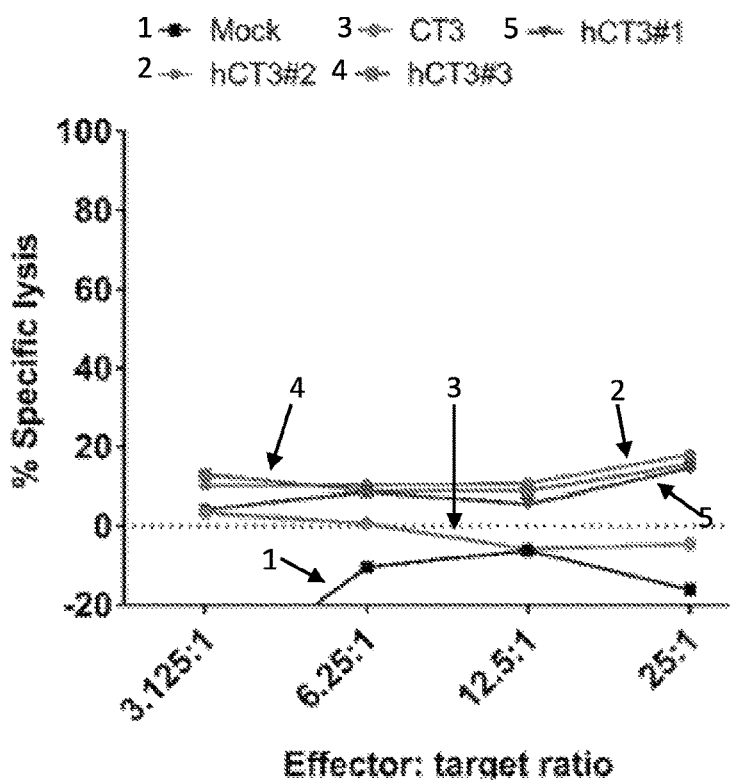
FIG. 8B G10
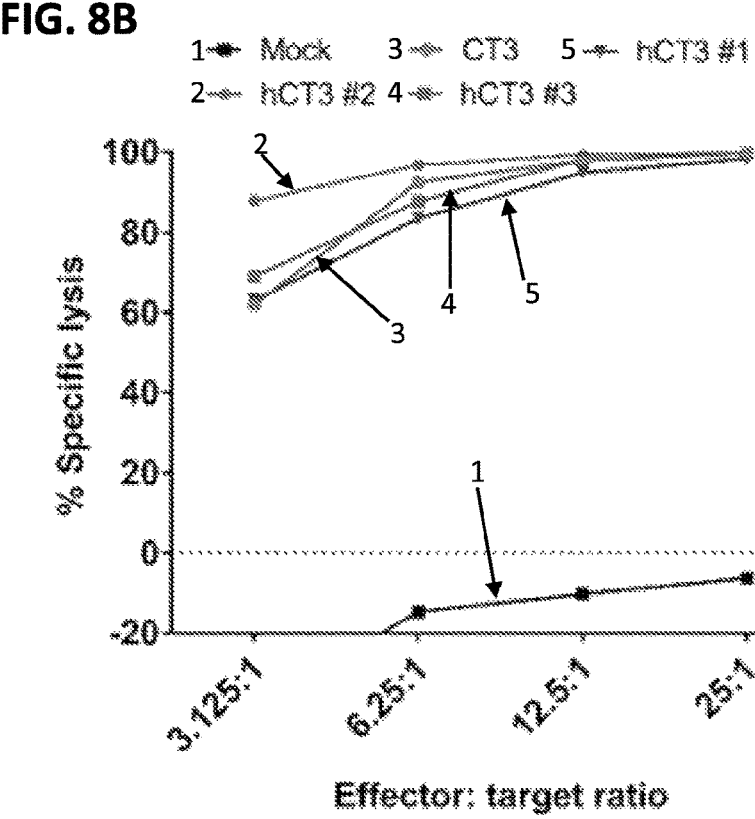

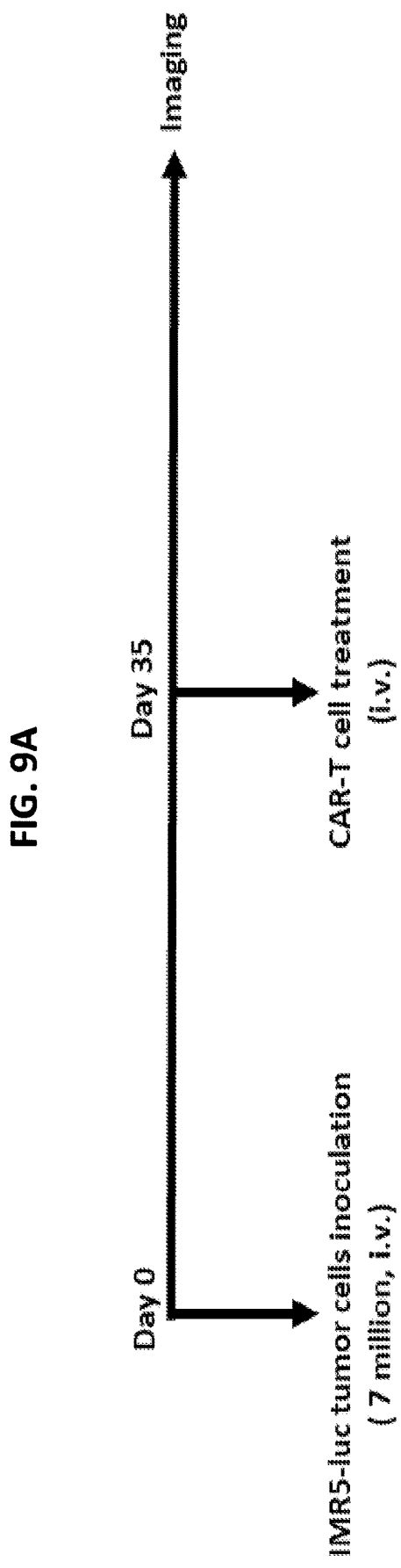

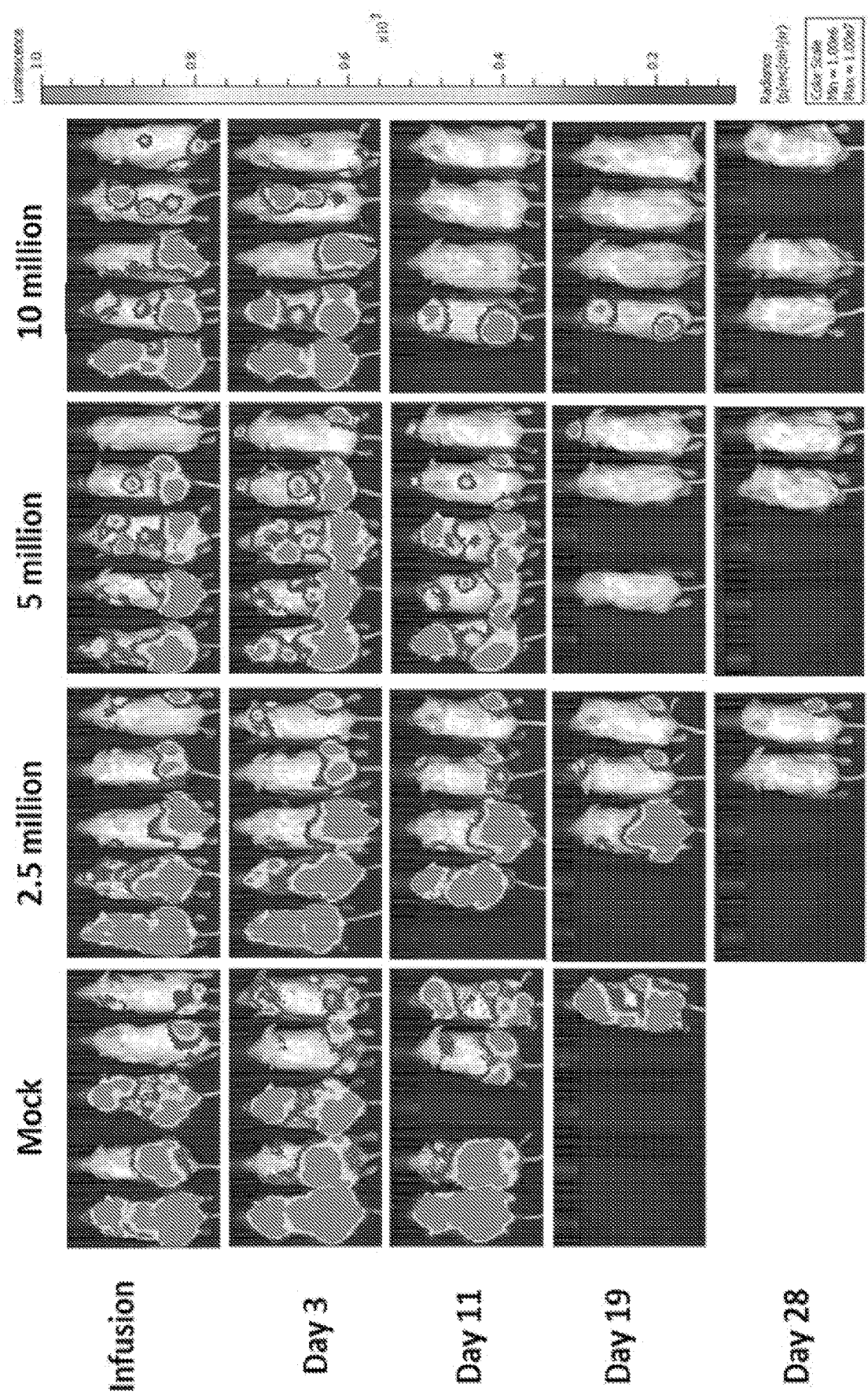

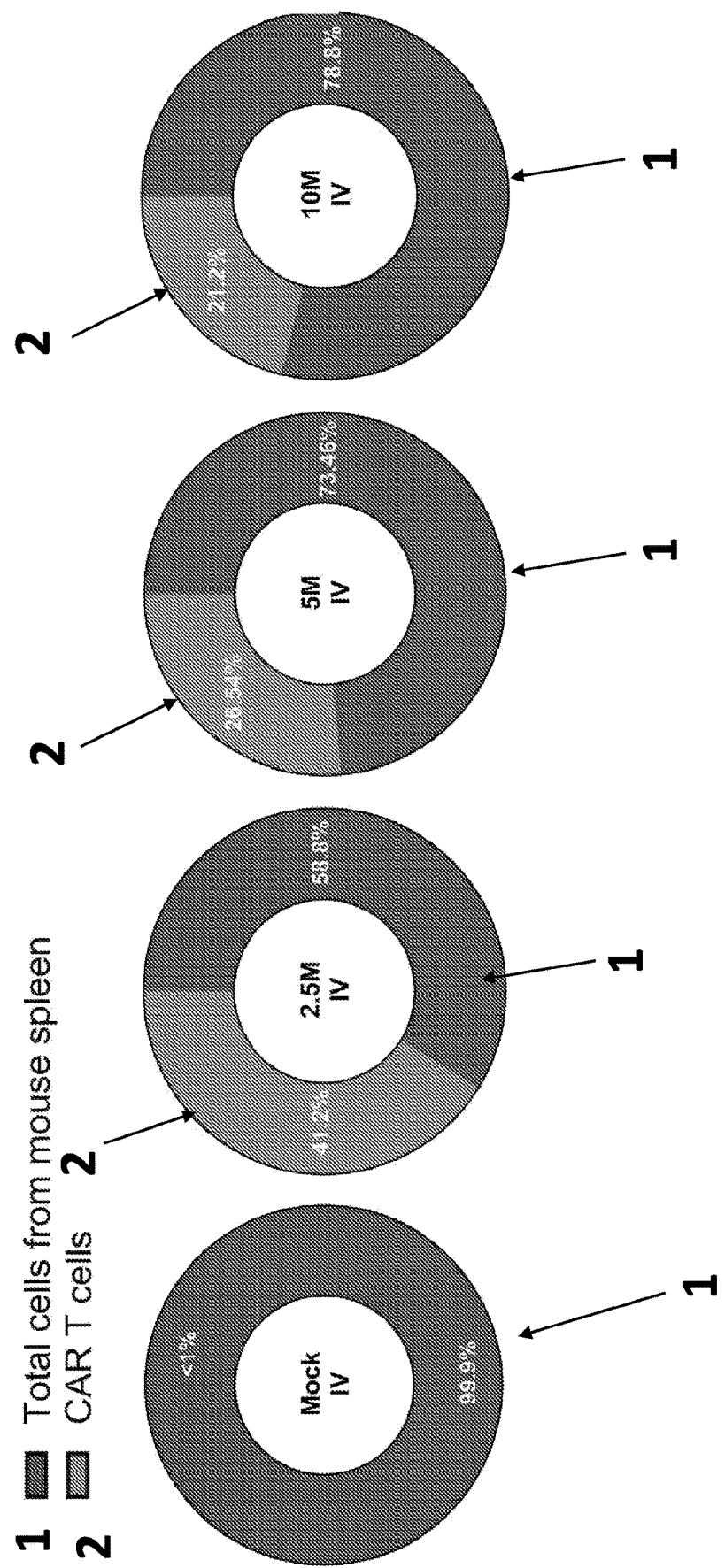

52.4 kD predicted

FIG. 12A
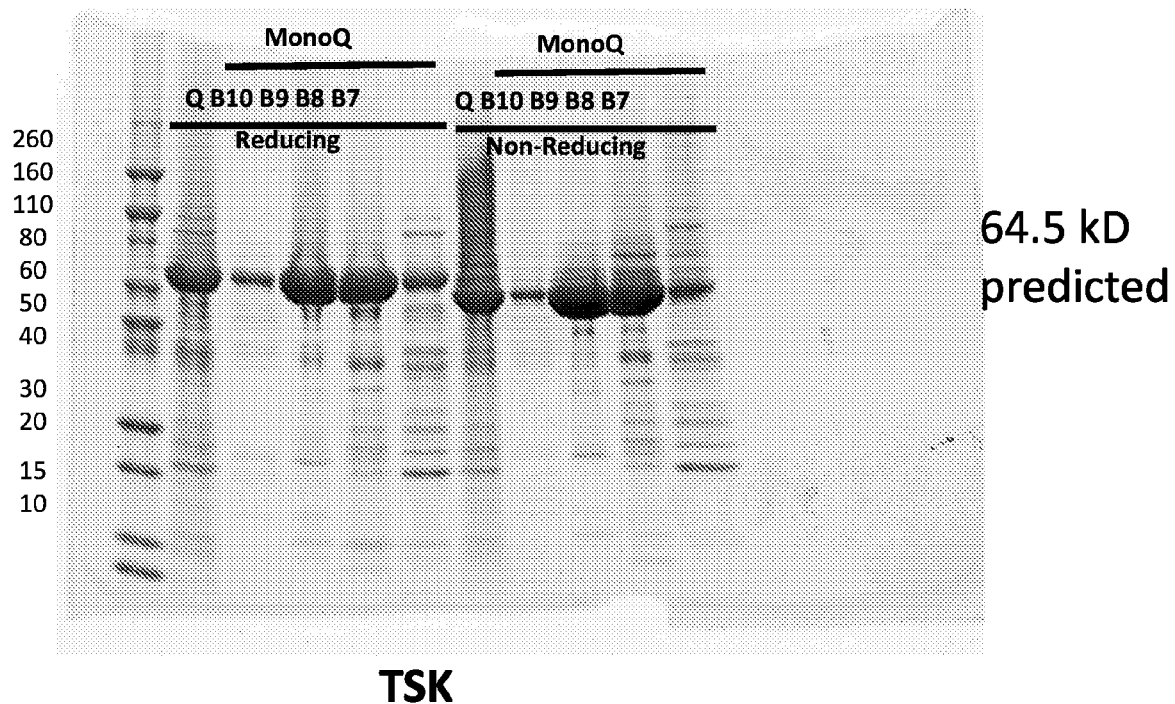
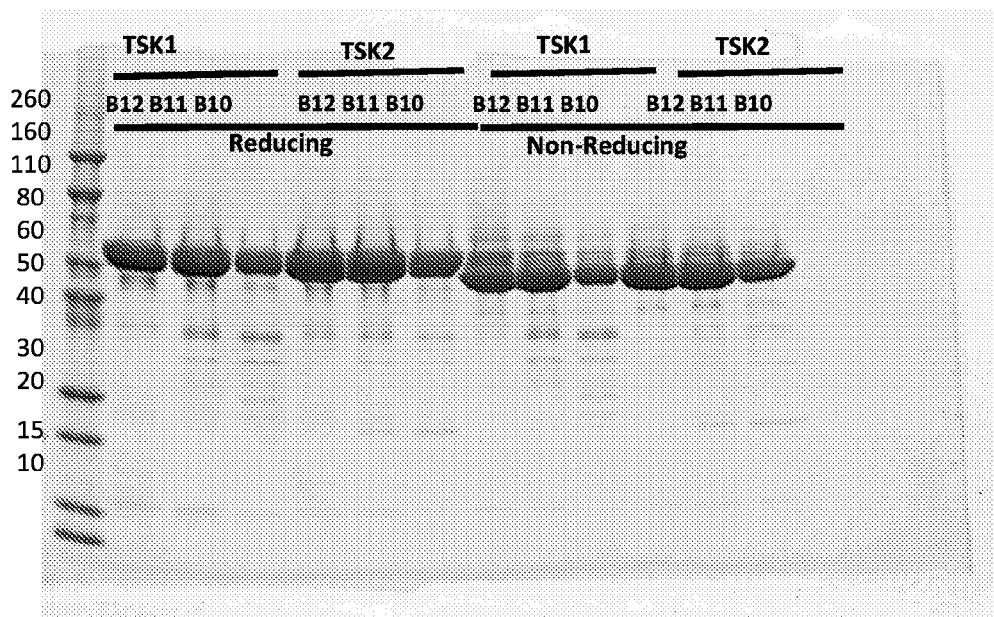
FIG. 12B

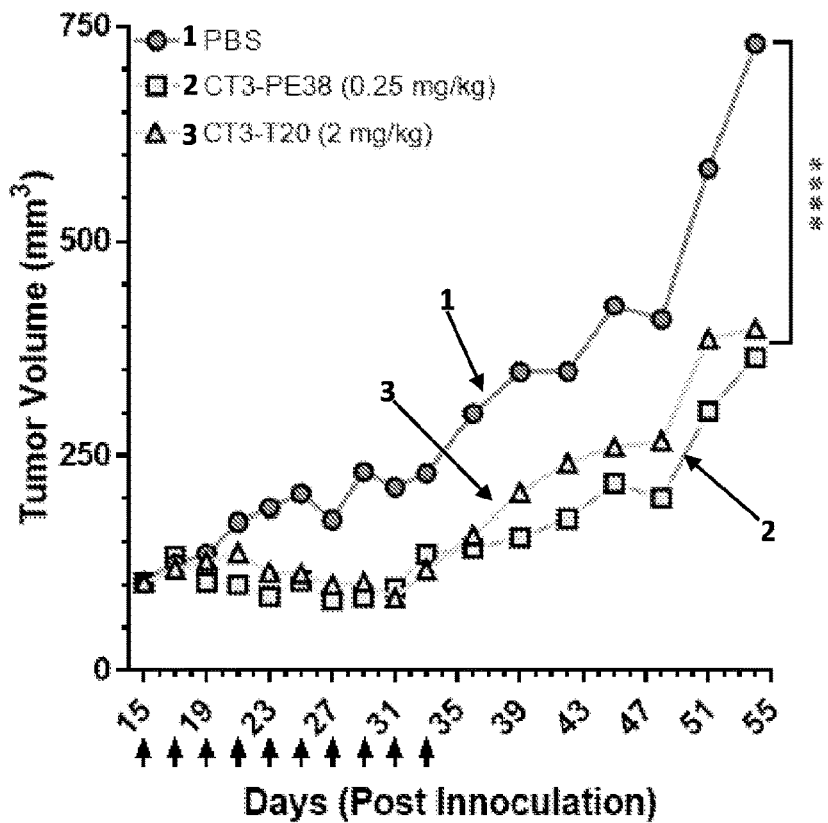
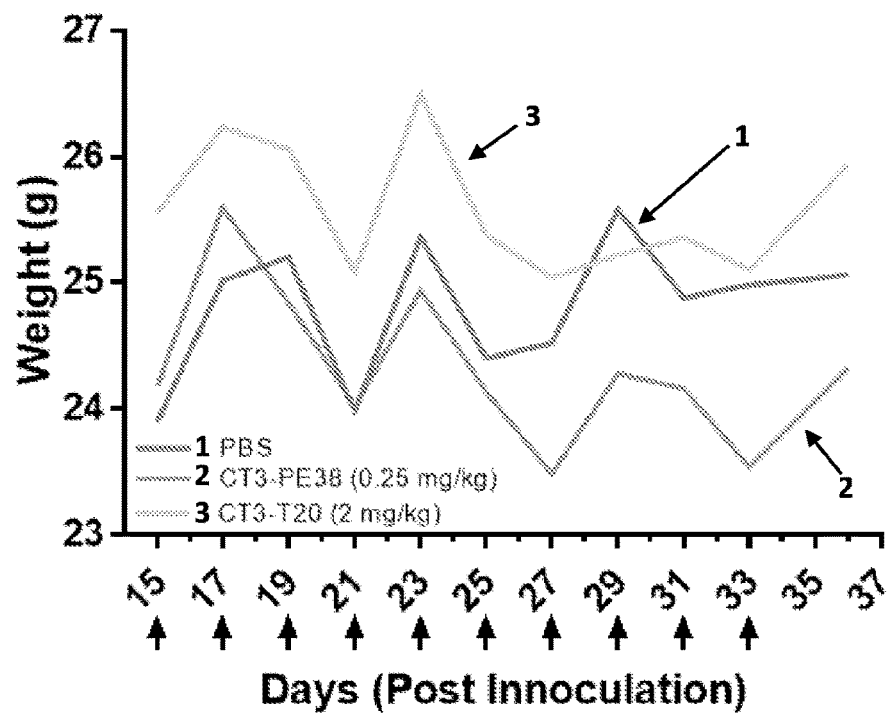
FIG. 13

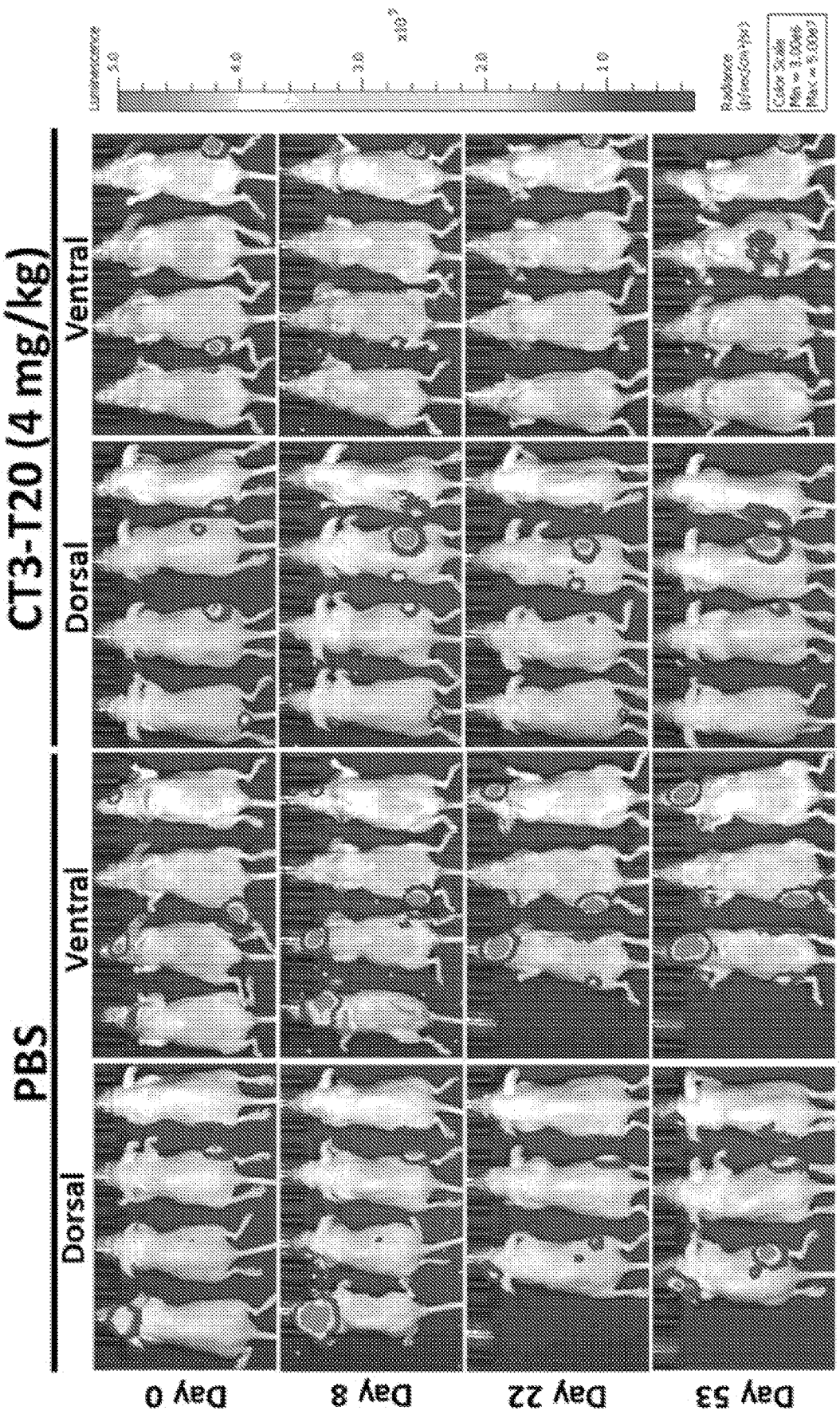

FIG. 15B
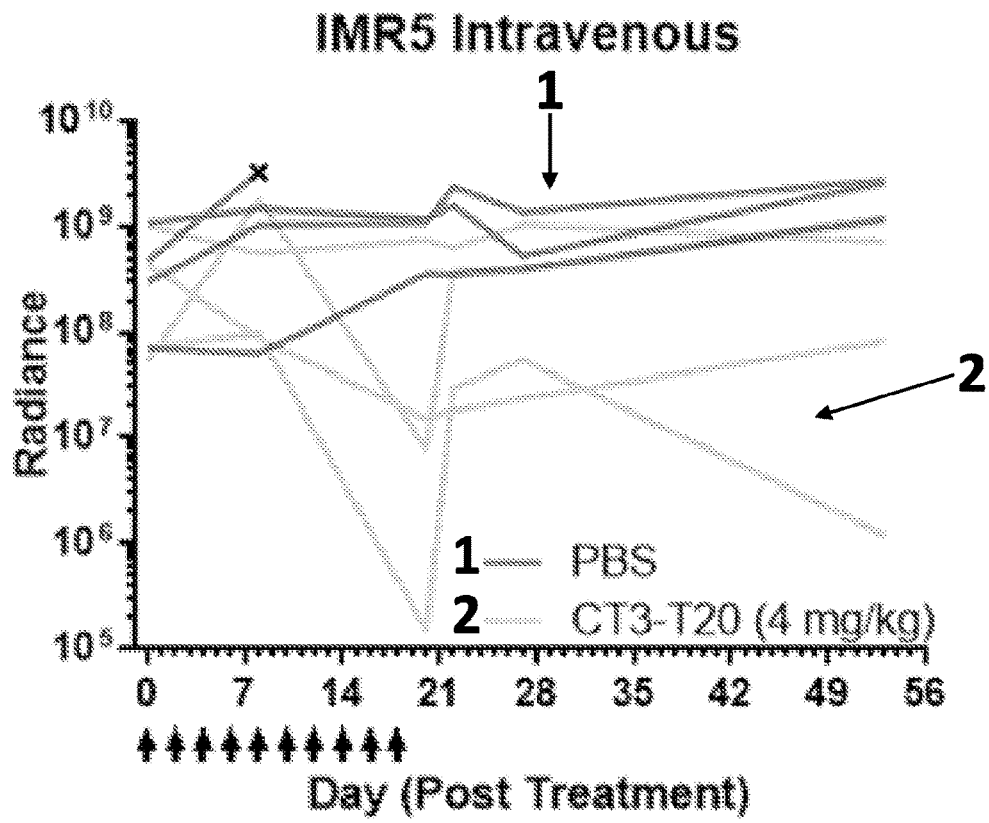
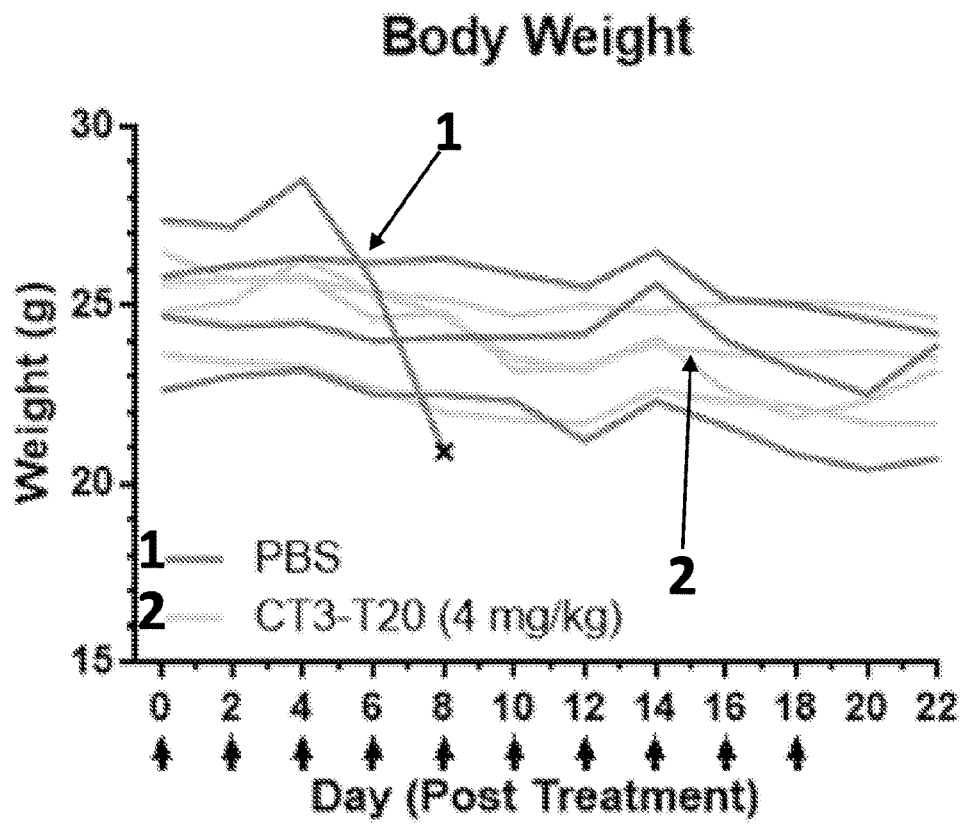

SEQUENCE LISTING

<160> NUMBER OF SEQ ID NOS: 23

<210> SEQ ID NO 1
<211> LENGTH: 369
<212> TYPE: DNA
<213> ORGANISM: Artificial Sequence
<220> FEATURE:
<223> OTHER INFORMATION: Synthetic polynucleotide

<400> SEQUENCE: 1

```
gaggtccagc tgcaacagtc tggacctgaa ctggtgaagc ctggggcttc agtaaagatg      60
tcctgcaagg cttctagatt cacattcact gactacaaca tacactgggt gaagcagagc     120
cctggaaaga cccttgaatg gattggatat attaacccta acaatggtga tattttctac     180
aaacagaagt tcaatggcaa ggccacattg actataaaca gtcctccaa cacagcctac     240 atggagctcc gcagcctgac atcggaggat tctgcagtct attactgtgt aagatcctct     300
aatattcgtt atactttcga caggttcttc gatgtctggg gcacagggac cacggtcacc     360
gtctcctca                                                             369
```

<210> SEQ ID NO 2
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 2

Glu Val Gln Leu Gln Gln Ser Gly Pro Glu Leu Val Lys Pro Gly Ala
1               5                   10                  15

Ser Val Lys Met Ser Cys Lys Ala Ser Arg Phe Thr Phe Thr Asp Tyr

```
            20                  25                  30
Asn Ile His Trp Val Lys Gln Ser Pro Gly Lys Thr Leu Glu Trp Ile
        35                  40                  45

Gly Tyr Ile Asn Pro Asn Asn Gly Asp Ile Phe Tyr Lys Gln Lys Phe
    50                  55                  60

Asn Gly Lys Ala Thr Leu Thr Ile Asn Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Val Arg Ser Ser Asn Ile Arg Tyr Thr Phe Asp Arg Phe Phe Asp Val
            100                 105                 110

Trp Gly Thr Gly Thr Thr Val Thr Val Ser Ser
            115                 120
```

<210> SEQ ID NO 3
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 3

```
gaaaatgtgc tcacccagtc tccagcaatc atgtctgcat ctctagggga gaaggtcacc      60
atgagctgca gggccagctc aagtgtaaat tacatttact ggtaccagca gaagtcagat     120
gcctccccca aactatggat ttattacaca tccaacctgg ctcctggagt cccagctcgc     180
ttcagtggca gtgggtctgg gaactcttat tctctcacaa tcagcagcat ggagggtgaa     240
gatgctgcca cttattactg ccagcagttt tctagttccc catccacgtt cggtactggg     300
accaagctgg agctgaaa                                                    318
```

<210> SEQ ID NO 4
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 4

```
Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Ile
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Ser Pro Ser Thr
                85                  90                  95

Phe Gly Thr Gly Thr Lys Leu Glu Leu Lys
            100                 105
```

<210> SEQ ID NO 5
<211> LENGTH: 357
<212> TYPE: DNA
<213> ORGANISM: Artificial Sequence
<220> FEATURE:

<223> OTHER INFORMATION: Synthetic polynucleotide

<400> SEQUENCE: 5

```
gaggtgaaac tggtggagtc tggaggaggc ttggtacagt ctgggcgttc tctgagactc      60
tcctgtgcaa cttctggatt caccttcagt gatttctaca tggagtgggt ccgccaagct     120
ccagggaagg gactggagtg gattgttgca agtagagaca aagctaatga ttatacaaca     180
gcgtatagtg catctgtgaa gggtcggttc atcgtctcca gagacacttc ccaaagcatc     240
ctctaccttc agatgaatgc cctgagagct gaggacactg ccatttatta ctgtgtaaga     300
gatttctatg attacgacga ggcttactgg ggccaaggga ctctggtcac tgtctct       357
```

<210> SEQ ID NO 6
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 6

```
Glu Val Lys Leu Val Glu Ser Gly Gly Gly Leu Val Gln Ser Gly Arg
1               5                   10                  15
Ser Leu Arg Leu Ser Cys Ala Thr Ser Gly Phe Thr Phe Ser Asp Phe
            20                  25                  30
Tyr Met Glu Trp Val Arg Gln Ala Pro Gly Lys Gly Leu Glu Trp Ile
        35                  40                  45
Val Ala Ser Arg Asp Lys Ala Asn Asp Tyr Thr Thr Ala Tyr Ser Ala
    50                  55                  60
Ser Val Lys Gly Arg Phe Ile Val Ser Arg Asp Thr Ser Gln Ser Ile
65                  70                  75                  80
Leu Tyr Leu Gln Met Asn Ala Leu Arg Ala Glu Asp Thr Ala Ile Tyr
                85                  90                  95
Tyr Cys Val Arg Asp Phe Tyr Asp Tyr Asp Glu Ala Tyr Trp Gly Gln
            100                 105                 110
Gly Thr Leu Val Thr Val Ser
        115
```

<210> SEQ ID NO 7
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 7

```
gacatccaga tgactcagtc tccgtcctca ctgtctgcct ctctgggagg tacagtcacc      60
atcacttgca aggcaagcga agacattaac aactatatag cttggtacca acacaagcct     120
ggaaaaggtc ctcggctgct catacaaatac acatctacat tacagccagg catcccatca     180
aggttcagtg gaagtgggtc tgggcgagat tattccctca gcatcagcaa cctgcagcct     240
gaagatattg caacttatta ttgtctacag tatgatattc tgtggacgtt cggtggaggc     300
accaagctgg aaatcaaa                                                   318
```

<210> SEQ ID NO 8
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 8

```
Asp Ile Gln Met Thr Gln Ser Pro Ser Ser Leu Ser Ala Ser Leu Gly
1               5                   10                  15

Gly Thr Val Thr Ile Thr Cys Lys Ala Ser Glu Asp Ile Asn Asn Tyr
            20                  25                  30

Ile Ala Trp Tyr Gln His Lys Pro Gly Lys Gly Pro Arg Leu Leu Ile
        35                  40                  45

Gln Tyr Thr Ser Thr Leu Gln Pro Gly Ile Pro Ser Arg Phe Ser Gly
    50                  55                  60

Ser Gly Ser Gly Arg Asp Tyr Ser Leu Ser Ile Ser Asn Leu Glu Pro
65                  70                  75                  80

Glu Asp Ile Ala Thr Tyr Tyr Cys Leu Gln Tyr Asp Ile Leu Trp Thr
                85                  90                  95

Phe Gly Gly Gly Thr Lys Leu Glu Ile Lys
            100                 105
```

<210> SEQ ID NO 9
<211> LENGTH: 244
<212> TYPE: PRT
<213> ORGANISM: Artificial Sequence
<220> FEATURE:
<223> OTHER INFORMATION: Synthetic polypeptide

<400> SEQUENCE: 9

```
Glu Val Gln Leu Gln Gln Ser Gly Pro Glu Leu Val Lys Pro Gly Ala
1               5                   10                  15

Ser Val Lys Met Ser Cys Lys Ala Ser Arg Phe Thr Phe Thr Asp Tyr
            20                  25                  30

Asn Ile His Trp Val Lys Gln Ser Pro Gly Lys Thr Leu Glu Trp Ile
        35                  40                  45

Gly Tyr Ile Asn Pro Asn Asn Gly Asp Ile Phe Tyr Lys Gln Lys Phe
    50                  55                  60

Asn Gly Lys Ala Thr Leu Thr Ile Asn Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Val Arg Ser Ser Asn Ile Arg Tyr Thr Phe Asp Arg Phe Phe Asp Val
            100                 105                 110

Trp Gly Thr Gly Thr Thr Val Thr Val Ser Ser Gly Gly Gly Gly Ser
        115                 120                 125

Gly Gly Gly Gly Ser Gly Gly Gly Gly Ser Glu Asn Val Leu Thr Gln
    130                 135                 140

Ser Pro Ala Ile Met Ser Ala Ser Leu Gly Glu Lys Val Thr Met Ser
145                 150                 155                 160

Cys Arg Ala Ser Ser Ser Val Asn Tyr Ile Tyr Trp Tyr Gln Gln Lys
                165                 170                 175

Ser Asp Ala Ser Pro Lys Leu Trp Ile Tyr Tyr Thr Ser Asn Leu Ala
            180                 185                 190

Pro Gly Val Pro Ala Arg Phe Ser Gly Ser Gly Ser Gly Asn Ser Tyr
        195                 200                 205

Ser Leu Thr Ile Ser Ser Met Glu Gly Glu Asp Ala Ala Thr Tyr Tyr
    210                 215                 220

Cys Gln Gln Phe Ser Ser Ser Pro Ser Thr Phe Gly Thr Gly Thr Lys
225                 230                 235                 240
```

Leu Glu Leu Lys

<210> SEQ ID NO 10
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Arg Phe Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Asn Pro Asn Asn Gly Asp Ile Phe Tyr Lys Gln Lys Phe
    50                  55                  60

Asn Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Val Arg Ser Ser Asn Ile Arg Tyr Thr Phe Asp Arg Phe Phe Asp Val
            100                 105                 110

Trp Gly Gln Gly Thr Leu Val Thr Val Ser Gly Gly Gly Gly Ser Gly
        115                 120                 125

Gly Gly Gly Ser Gly Gly Gly Ser Asp Val Val Met Thr Gln Ser
    130                 135                 140

Pro Leu Ser Leu Pro Val Thr Pro Gly Glu Pro Ala Ser Ile Ser Cys
145                 150                 155                 160

Arg Ala Ser Ser Ser Val Asn Tyr Ile Tyr Trp Tyr Leu Gln Lys Pro
                165                 170                 175

Gly Gln Ser Pro Gln Leu Trp Ile Tyr Tyr Thr Ser Asn Leu Ala Pro
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Val Tyr Tyr Cys
    210                 215                 220

Gln Gln Phe Ser Ser Ser Pro Ser Thr Phe Gly Gln Gly Thr Lys Leu
225                 230                 235                 240

Glu Ile Lys
```

<210> SEQ ID NO 11
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Arg Phe Thr Phe Thr Asp Tyr
            20                  25                  30

Asn Ile His Trp Val Arg Gln Ala Pro Gly Gln Arg Leu Glu Trp Ile
        35                  40                  45

Gly Tyr Ile Asn Pro Asn Asn Gly Asp Ile Phe Tyr Lys Gln Lys Phe
```

```
            50                  55                  60
Asn Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Ser Asn Ile Arg Tyr Thr Phe Asp Arg Phe Phe Asp Val
                100                 105                 110

Trp Gly Gln Gly Thr Leu Val Thr Val Ser Gly Gly Gly Gly Ser Gly
                115                 120                 125

Gly Gly Gly Ser Gly Gly Gly Ser Asp Val Val Met Thr Gln Ser
                130                 135                 140

Pro Ala Phe Leu Ser Val Thr Pro Gly Glu Lys Val Thr Ile Thr Cys
145                 150                 155                 160

Arg Ala Ser Ser Ser Val Asn Tyr Ile Tyr Trp Tyr Gln Gln Lys Pro
                165                 170                 175

Asp Gln Ala Pro Lys Leu Trp Ile Tyr Tyr Thr Ser Asn Leu Ala Pro
                180                 185                 190

Gly Val Pro Ser Arg Phe Ser Gly Ser Gly Ser Gly Thr Asp Phe Thr
                195                 200                 205

Phe Thr Ile Ser Ser Leu Glu Ala Glu Asp Ala Ala Thr Tyr Tyr Cys
210                 215                 220

Gln Gln Phe Ser Ser Pro Ser Thr Phe Gly Gln Gly Thr Lys Leu
225                 230                 235                 240

Glu Ile Lys

<210> SEQ ID NO 12
<211> LENGTH: 245
<212> TYPE: PRT
<213> ORGANISM: Artificial Sequence
<220> FEATURE:
<223> OTHER INFORMATION: Synthetic polypeptide

<400> SEQUENCE: 12

Met Gln Val Gln Leu Gln Gln Ser Gly Pro Glu Leu Glu Lys Pro Gly
 1                5                  10                  15

Ala Ser Val Lys Ile Ser Cys Lys Ala Ser Arg Phe Thr Phe Thr Asp
                 20                  25                  30

Tyr Asn Ile His Trp Val Lys Gln Ser His Gly Lys Cys Leu Glu Trp
             35                  40                  45

Ile Gly Tyr Ile Asn Pro Asn Asn Gly Asp Ile Phe Tyr Lys Gln Lys
         50                  55                  60

Phe Asn Gly Lys Ala Thr Leu Thr Val Asp Lys Ser Ser Ser Thr Ala
 65                  70                  75                  80

Tyr Met Asp Leu Leu Ser Leu Thr Ser Glu Asp Ser Ala Val Tyr Phe
                 85                  90                  95

Cys Val Arg Ser Ser Asn Ile Arg Tyr Thr Phe Asp Arg Phe Phe Asp
                100                 105                 110

Val Trp Gly Gln Gly Thr Thr Val Thr Val Ser Ser Gly Gly Gly Gly
                115                 120                 125

Ser Gly Gly Gly Gly Ser Gly Gly Gly Ser Asp Ile Glu Leu Thr
                130                 135                 140

Gln Ser Pro Ala Ile Met Ser Ala Ser Pro Gly Glu Lys Val Thr Met
145                 150                 155                 160

Thr Cys Arg Ala Ser Ser Ser Val Asn Tyr Ile Tyr Trp Tyr Gln Gln
                165                 170                 175
```

```
Lys Ser Gly Thr Ser Pro Lys Leu Trp Ile Tyr Tyr Thr Ser Asn Leu
            180                 185                 190

Ala Pro Gly Val Pro Gly Arg Phe Ser Gly Ser Gly Ser Gly Asn Ser
        195                 200                 205

Tyr Ser Leu Thr Ile Ser Ser Val Glu Ala Glu Asp Asp Ala Thr Tyr
        210                 215                 220

Tyr Cys Gln Gln Phe Ser Ser Pro Ser Thr Phe Gly Cys Gly Thr
225                 230                 235                 240

Lys Leu Glu Ile Lys
            245

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide

<400> SEQUENCE: 13

Asn Tyr His Leu Glu Asn Glu Val Ala Arg Leu Lys Lys Leu
1               5                   10

<210> SEQ ID NO 14
<211> LENGTH: 22
<212> TYPE: PRT
<213> ORGANISM: Homo sapiens

<400> SEQUENCE: 14

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 15
<211> LENGTH: 45
<212> TYPE: PRT
<213> ORGANISM: Homo sapiens

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 16
<211> LENGTH: 21
<212> TYPE: PRT
<213> ORGANISM: Homo sapiens

<400> SEQUENCE: 16

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 17
<211> LENGTH: 42
<212> TYPE: PRT
<213> ORGANISM: Artificial Sequence
```

```
<220> FEATURE:
<223> OTHER INFORMATION: Synthetic polypeptide

<400> SEQUENCE: 17

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 18
<211> LENGTH: 112
<212> TYPE: PRT
<213> ORGANISM: Homo sapiens

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 19
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 19

Glu Gly Arg Gly Ser Leu Leu Thr Cys Gly Asp Val Glu Glu Asn Pro
1               5                   10                  15

Gly Pro

<210> SEQ ID NO 20
<211> LENGTH: 335
<212> TYPE: PRT
<213> ORGANISM: Homo sapiens

<400> SEQUENCE: 20

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
```

```
                65                  70                  75                  80
Arg Thr Asp Leu His Ala Phe Glu Asn Leu Glu Ile Ile Arg Gly Arg
                    85                  90                  95

Thr Lys Gln His Gly Gln Phe Ser Leu Ala Val Val Ser Leu Asn Ile
                100                 105                 110

Thr Ser Leu Gly Leu Arg Ser Leu Lys Glu Ile Ser Asp Gly Asp Val
                115                 120                 125

Ile Ile Ser Gly Asn Lys Asn Leu Cys Tyr Ala Asn Thr Ile Asn Trp
            130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
                180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
        290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 21
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Arg Phe Thr Phe Thr Asp Tyr
                20                  25                  30

Asn Ile His Trp Val Arg Gln Ala Pro Gly Gln Gly Leu Glu Trp Ile
            35                  40                  45

Gly Tyr Ile Asn Pro Asn Asn Gly Asp Ile Phe Tyr Lys Gln Lys Phe
        50                  55                  60

Asn Gly Lys Ala Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Ser Ser Asn Ile Arg Tyr Thr Phe Asp Arg Phe Phe Asp Val
```

```
                    100                 105                 110
Trp Gly Gln Gly Thr Leu Val Thr Val Ser Gly Gly Gly Ser Gly
            115                 120                 125
Gly Gly Gly Ser Gly Gly Gly Ser Asp Ile Gln Met Thr Gln Ser
        130                 135                 140
Pro Ser Ser Leu Ser Ala Ser Val Gly Asp Arg Val Thr Ile Thr Cys
145                 150                 155                 160
Arg Ala Ser Ser Val Asn Tyr Ile Tyr Trp Tyr Gln Gln Lys Ser
                165                 170                 175
Gly Lys Ala Pro Lys Leu Trp Ile Tyr Tyr Thr Ser Asn Leu Ala Pro
            180                 185                 190
Gly Val Pro Ser Arg Phe Ser Gly Ser Gly Ser Gly Thr Asp Phe Thr
        195                 200                 205
Leu Thr Ile Ser Ser Leu Gln Pro Glu Asp Phe Ala Thr Tyr Tyr Cys
    210                 215                 220
Gln Gln Phe Ser Ser Pro Ser Thr Phe Gly Gln Gly Thr Lys Leu
225                 230                 235                 240
Glu Ile Lys

<210> SEQ ID NO 22
<211> LENGTH: 355
<212> TYPE: PRT
<213> ORGANISM: Artificial Sequence
<220> FEATURE:
<223> OTHER INFORMATION: Synthetic polypeptide

<400> SEQUENCE: 22

Ser Ala Ala Lys Ala Ser Gly Gly Pro Glu Gly Gly Ser Leu Ala Ala
1                   5                   10                  15
Leu Thr Ala His Gln Ala Cys His Leu Pro Leu Glu Thr Phe Thr Arg
                20                  25                  30
His Arg Gln Pro Arg Gly Trp Glu Gln Leu Glu Gln Cys Gly Tyr Pro
            35                  40                  45
Val Gln Arg Leu Val Ala Leu Tyr Leu Ala Ala Arg Leu Ser Trp Asn
        50                  55                  60
Gln Val Asp Gln Val Ile Arg Asn Ala Leu Ala Ser Pro Gly Ser Gly
65                  70                  75                  80
Gly Asp Leu Gly Glu Ala Ile Arg Glu Gln Pro Glu Gln Ala Arg Leu
                85                  90                  95
Ala Leu Thr Leu Ala Ala Ala Glu Ser Glu Arg Phe Val Arg Gln Gly
            100                 105                 110
Thr Gly Asn Asp Glu Ala Gly Ala Ala Asn Gly Pro Ala Asp Ser Gly
        115                 120                 125
Asp Ala Leu Leu Glu Arg Asn Tyr Pro Thr Gly Ala Glu Phe Leu Gly
    130                 135                 140
Asp Gly Gly Asp Val Ser Phe Ser Thr Arg Gly Thr Gln Asn Trp Thr
145                 150                 155                 160
Val Glu Arg Leu Leu Gln Ala His Arg Gln Leu Glu Glu Arg Gly Tyr
                165                 170                 175
Val Phe Val Gly Tyr His Gly Thr Phe Leu Glu Ala Ala Gln Ser Ile
            180                 185                 190
Val Phe Gly Gly Val Arg Ala Arg Ser Gln Asp Leu Asp Ala Ile Trp
        195                 200                 205
Arg Gly Phe Tyr Ile Ala Gly Asp Pro Ala Leu Ala Tyr Gly Tyr Ala
    210                 215                 220
```

Gln Asp Gln Glu Pro Asp Ala Arg Gly Arg Ile Arg Asn Gly Ala Leu
225                 230                 235                 240

Leu Arg Val Tyr Val Pro Arg Ser Ser Leu Pro Gly Phe Tyr Arg Thr
            245                 250                 255

Ser Leu Thr Leu Ala Ala Pro Glu Ala Ala Gly Glu Val Glu Arg Leu
        260                 265                 270

Ile Gly His Pro Leu Pro Leu Arg Leu Asp Ala Ile Thr Gly Pro Glu
    275                 280                 285

Glu Glu Gly Gly Arg Leu Glu Thr Ile Leu Gly Trp Pro Leu Ala Glu
290                 295                 300

Arg Thr Val Val Ile Pro Ser Ala Ile Pro Thr Asp Pro Arg Asn Val
305                 310                 315                 320

Gly Gly Asp Leu Asp Pro Ser Ser Ile Pro Asp Lys Glu Gln Ala Ile
            325                 330                 335

Ser Ala Leu Pro Asp Tyr Ala Ser Gln Pro Gly Lys Pro Pro Arg Glu
        340                 345                 350

Asp Leu Lys
    355

<210> SEQ ID NO 23
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 23

Lys Leu Lys Ala Ser Gly Gly Arg His Arg Gln Pro Arg Gly Trp Glu
1               5                   10                  15

Gln Leu Gly Gly Gly Gly Ser Pro Thr Gly Ala Glu Phe Leu Gly
            20                  25                  30

Asp Gly Gly Asp Val Ser Phe Ser Thr Arg Gly Thr Gln Asn Trp Thr
        35                  40                  45

Val Glu Arg Leu Leu Gln Ala His Ala Gln Leu Glu Glu Arg Gly Tyr
50                  55                  60

Val Phe Val Gly Tyr His Gly Thr Ala Leu Glu Ala Ala Gln Ser Ile
65                  70                  75                  80

Val Phe Gly Gly Val Arg Ala Arg Ser Gln Asp Leu Asp Ala Ile Trp
            85                  90                  95

Arg Gly Phe Tyr Ile Ala Gly Asp Pro Ala His Ala Tyr Gly Tyr Ala
        100                 105                 110

Gln Asp Gln Glu Pro Asp Ala Arg Gly Arg Ile Ala Asn Gly Ala Leu
    115                 120                 125

Leu Arg Val Tyr Val Pro Ala Ser Ser Leu Pro Gly Phe Tyr Arg Thr
130                 135                 140

Ser Leu Thr Leu Ala Ala Pro Glu Ala Ala Gly Glu Val Glu Arg Leu
145                 150                 155                 160

Ile Gly His Pro Leu Pro Leu Arg Leu Asp Ala Ile Thr Gly Pro Glu
            165                 170                 175

Glu Glu Gly Gly Arg Glu Glu Thr Ile Leu Gly Trp Pro Leu Ala Glu
        180                 185                 190

Arg Thr Val Val Ile Pro Ser Ala Ile Pro Thr Asp Pro Arg Asn Val
    195                 200                 205

Gly Gly Asp Leu Asp Pro Ser Ser Ile Pro Asp Lys Glu Gln Ala Ile
210                 215                 220

```
Ser Ala Leu Pro Asp Tyr Ala Ser Gln Pro Gly Lys Pro Pro Arg Glu
225                 230                 235                 240

Asp Leu Lys
```

HIGH AFFINITY MONOCLONAL ANTIBODIES TARGETING GLYPICAN-2 AND USES THEREOF

CROSS REFERENCE TO RELATED APPLICATIONS

This application is the U.S. National Stage of International Application No. PCT/US2019/045338, filed Aug. 6, 2019, published in English under PCT Article 21(2), which claims the benefit of U.S. Provisional Application No. 62/716,169, filed Aug. 8, 2018, which is herein incorporated by reference in its entirety.

ACKNOWLEDGMENT OF GOVERNMENT SUPPORT

This invention was made with government support under project number Z01 BC010891 awarded by the National Institutes of Health. The government has certain rights in the invention.

FIELD

This disclosure concerns monoclonal antibodies that specifically bind glypican-2 and uses thereof, such as for the treatment of pediatric cancers.

BACKGROUND

Neuroblastoma is the most common extracranial solid tumors of children. Derived from neuroendocrine tissue of the sympathetic nervous system, it accounts for 8-10% of childhood cancers in the USA (Maris and Hogarty, *Lancet* 369:2106-2120, 2007). Neuroblastoma is a complex and heterogeneous disease, with nearly 50% of patients having a high-risk phenotype characterized by widespread dissemination of the cancer and poor long-term survival even if intensive multimodal treatments are used (Yu et al., *New Engl J Med* 363:1324-1334, 2010). Approximately 45% of patients receiving standard therapy have a relapse and ultimately succumb to metastatic disease (Matthay et al., *New Engl J Med* 341:1165-1173, 1999). As such, there is an unmet urgent need for a safe and effective treatment of neuroblastoma.

One of the most difficult challenges for the treatment of neuroblastoma and other deadly solid tumors is the lack of tumor-specific targets. It has been shown that glypican-2 (GPC2) mRNA is highly expressed in neuroblastoma and other pediatric cancers (Orentas et al., *Front Oncol* 2:194, 2012). GPC2 belongs to the six-member human glypican family of proteins that are attached to the cell surface by a glycosylphosphatidylinositol (GPI) anchor (Filmus et al., *Genome Biol* 9:224, 2008). Unlike other known glypicans, GPC2 is uniquely expressed in the nervous system (Stipp et al., *J Cell Biol* 124:149-160, 1994), participates in cell adhesion and is thought to regulate the growth and guidance of axons.

SUMMARY

The present disclosure describes two high affinity GPC2-specific monoclonal antibodies isolated by mouse hybridoma technology. The GPC2 antibodies, referred to as CT3 and CT5, specifically bind GPC2, but not other glypicans Immunotoxins and chimeric antigen receptor (CAR) T cells comprised of the disclosed antibodies are capable of potently killing GPC2 positive-tumor cells.

Provided herein are monoclonal antibodies (or antigen-binding fragments) that bind, such as specifically bind, GPC2. In some embodiments, the monoclonal antibody or antigen-binding fragment includes the complementarity determining region (CDR) sequences of CT3 or CT5. Also provided herein are conjugates that include a disclosed monoclonal antibody or antigen-binding fragment. In some examples, provided are immunoconjugates, CARs, multi-specific antibodies, antibody-drug conjugates (ADCs), antibody-nanoparticles, conjugates or fusion proteins that include a monoclonal antibody or antigen-binding fragment disclosed herein. Compositions that include a GPC-specific monoclonal antibody or antigen-binding fragment and a pharmaceutically acceptable carrier are also provided by the present disclosure.

Also provided herein are nucleic acid molecules and vectors encoding the GPC2-specific monoclonal antibodies or antigen-binding fragments, immunoconjugates, CARs, multi-specific antibodies and fusion proteins disclosed herein.

Further provided are nucleic acid constructs that encode both a GPC2-specific CAR and a truncated human epidermal growth factor receptor (huEGFRt). The encoded CARs include a GPC2-specific monoclonal antibody fragment (such as a scFv) fused to an extracellular hinge region, a transmembrane region, an intracellular co-stimulatory domain and an intracellular signaling domain. The huEGFRt includes two EGFR extracellular domains (Domain III and Domain IV) and the EGFR transmembrane domain, but lacks the two membrane distal extracellular domains and all intracellular domains. In some embodiments, the nucleic acid molecule includes, in the 5' to 3' direction, a nucleic acid encoding a first signal sequence; a nucleic acid encoding a GPC2-specific antibody or antigen-binding fragment thereof; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second signal sequence; and a nucleic acid encoding a huEGFRt. Also provided are vectors, such as viral vectors, that include a nucleic acid molecule disclosed herein. Isolated cells, such as T lymphocytes, that co-express the disclosed CARs and huEGFRt are also disclosed.

Methods of treating a GPC2-positive cancer in a subject, and methods of inhibiting tumor growth or metastasis of a GPC2-positive cancer in a subject are also provided. In some embodiments, the methods include administering to the subject a monoclonal antibody or antigen-binding fragment disclosed herein, or administering to the subject an immunoconjugate, CAR, ADC, multi-specific antibody, antibody-nanoparticle conjugate or fusion protein comprising a monoclonal antibody or antigen-binding fragment disclosed herein.

Further provided herein are methods of detecting expression of GPC2 in a sample. In some embodiments, the method includes contacting the sample with a monoclonal antibody or antigen-binding fragment disclosed herein, and detecting binding of the antibody to the sample.

Also provided are methods of diagnosing a subject as having a GPC2-positive cancer. In some embodiments, the method includes contacting a sample obtained from the subject with a monoclonal antibody or antigen-binding fragment disclosed herein, and detecting binding of the antibody to the sample.

The foregoing and other objects and features of the disclosure will become more apparent from the following detailed description, which proceeds with reference to the accompanying figures.

BRIEF DESCRIPTION OF THE DRAWINGS

FIG. 2A: Cell-surface GPC2 expression of GPC2-positive neuroblastoma cell lines, LAN1 and IMR5, as determined by flow cytometry. White peaks represent cell-surface staining with isotype control antibody, and black peaks represent cell-surface staining by CT5 antibody. CT5 at 10 ng/ml was used for staining.

FIG. 2B: Specific binding of CT3 antibody to human GPC2 on the cell surface. A431 cells, which do not express GPC2, were used as a control. G10 is a GPC2-overexpressing A431 cell line. F8 is a GPC2-overexpressing IMR5 cell line. Peaks labelled "1" represent cell surface staining with an isotype control antibody, and peaks labelled "2" represent cell surface staining by anti-GPC2 antibody CT3. CT3 specifically recognizes GPC2 expressed on the cell surface.

(FIG. 7A) Schematic diagram of the lentiviral construct expressing CT3 CAR targeting GPC2 along with truncated human EGFR (huEGFRt) using the T2A ribosomal skipping sequence. (FIG. 7B) CT3 CAR expression on human T cells transduced with lentiviral particles was analyzed using flow cytometry by detection of huEGFRt expression. (FIGS. 7C-7E) Cytolytic activities of GPC2 targeting CAR T cells in cell assays. The luciferase expressing SKNBE2 (FIG. 7C), NBEB (FIG. 7D) and LAN1 (FIG. 7E) neuroblastoma cells were co-cultured with mock or CT3 CAR-transduced T cells at the indicated effector (E): Target (T) ratios for 20 hours, and specific lysis was measured using a luminescent-based cytolytic assay. CT3 CAR T cells induced efficient lysis of GPC2-expressing neuroblastoma cells.

FIGS. 8A-8D: Cytolytic activity of GPC2-targeted CAR T cells after 20 hours of co-culture with GPC2-positive cells (G10, IMR5, F8) and GPC2-negative cells (A431) at the indicated E:T ratios. Specific lysis was measured using a luminescent-based cytolytic assay. hCT3 #1, #2 and #3 represent three CAR versions with different humanized CT3 antibodies (set forth herein as SEQ ID NOs: 10, 11 and 21, respectively). The CT3 and humanized CT3 (hCT3) CAR T cells potently lysed GPC2-positive tumor cells, but not GPC2-negative A431 cells.

FIGS. 9A-9B: (FIG. 9A) Experimental schematic of IMR5 tumor-bearing NSG mice treated with intravenous tail vein injections of mock T cells (mock), 2.5 million, 5 million, and 10 million (CT3) CAR T cells. Tumor burden was monitored by bioluminescent imaging at Day 0 (Infusion), Day 3, Day 11, Day 10 and Day 28 post-CAR T cell infusion. (FIG. 9B) CT3 CAR regresses metastatic IMR5 neuroblastoma tumors. Partial response was obtained with dose as low as 2.5 million CT3 CAR T cells while complete responses were obtained in both the 5 million and 10 million CT3 CAR T cell groups.

FIG. 10: Detection of CAR vector positive cells in mouse spleens after 2-4 weeks of treatment. The spleens were harvested at Day 34 (2.5M #737), Day 14 (5M #733) and Day 28 (10M #742) after treatment. CT3 CAR T cells present in mouse spleen one month after treatment ranged between 21.2% to 41.2% of the total mouse spleen cells.

(FIG. 11A) Human GPC2-His (250 ng/ml) was loaded onto Ni-NTA biosensor using an Octet Red96e system Immunotoxins (CT3-PE38 and CT3-T20) were added at 100 nM to determine the affinity of binding. Association occurred for 600 seconds and dissociation occurred for 1800 seconds. Affinity ($K_D$) of CT3-PE38 and CT3-T20 for human GPC2 was determined to be 0.22 nM and 0.16 nM, respectively. (FIGS. 11B-11C) The CT3-PE38 immunotoxin was purified using anionic exchange and size exclusion chromatography. Tris-Glycine 4-20% gels were used to assess fraction purities during protein elution. FIG. 11B represents selected fractions from the Qseph and MonoQ column elutions. FIG. 11C represents fractions from the TSK column elution. (FIGS. 11D-11E) The CT3-T20 immunotoxin was purified using anionic exchange and size exclusion chromatography. Tris-Glycine 4-20% gels were used to assess fraction purities during protein elution. FIG. 11D represents selected fractions from the Qseph and MonoQ column elutions. FIG. 11E represents fractions from the TSK column elution. (FIGS. 11F-11G) The CT3-PE38 (FIG. 11F) and CT3-T20 (FIG. 11G) immunotoxins selectively kill GPC2-expressing cells lines. Cells were incubated with varying concentrations of immunotoxin for three days, then cell number was determined using the WST-8 cell proliferation assay. Cell proliferation in the untreated wells was set to 100% when calculating inhibition of cell proliferation. Treatment with CT3-PE38 and CT3-T20 caused inhibition of GPC2-positive cells including G10, F8, and IMR5. The antigen-low IMR32 and antigen-negative-A431 cells showed no inhibition.

FIGS. 12A-12C: Characterization of the sCT3-PE38 immunotoxin. (FIGS. 12A-12B) The sCT3-PE38 immunotoxin was purified using anionic exchange and size exclusion chromatography. Tris-Glycine 4-20% gels were used to assess fraction purities during protein elution. FIG. 12A represents selected fractions from the Qseph and MonoQ column elutions. FIG. 12B represents fractions from the two independent TSK column runs. (FIG. 12C) The sCT3-PE38 immunotoxin selectively kills GPC2-expressing cells lines. Cells were incubated with varying concentrations of immunotoxin for three days, then cell number was determined using the WST-8 cell proliferation assay. Cell proliferation in the untreated wells was set to 100% when calculating inhibition of cell proliferation. Treatment with sCT3-PE38 caused inhibition of GPC2-positive cells including G10, F8, IMR5 and SKNBE. The antigen-negative A431 and SKNAS cells showed no inhibition by sCT3-PE38.

FIG. 13: Ten million F8 cells in Matrigel were injected into the right dorsal flank of nude mice. Treatment with PBS, CT3-PE38 (0.25 mg/kg) or CT3-T20 (2 mg/kg) began when average tumor volume reached 100 mm$^3$. Arrows indicate treatment days. A 2-way ANOVA test was used to determine significance for tumor volume, ****$p<0.0001$, n=5. Body weight of treated mice was also measured. CT3 based immunotoxins were well tolerated in nude mice and significantly inhibited F8 subcutaneous xenografts.

FIGS. 15A-15B: Five million IMR5 cells were injected via tail vein into nude mice. Mice were treated with PBS or CT3-T20 (4 mg/kg). Arrows indicate treatment days. Radiance was determined with an IVIS Lumina Series III following a 100 μl injection of xenolight D-luciferin (30 mg/ml) (FIG. 15A). Treatment with CT3-T20 immunotoxin caused reduced tumor burden without significantly changing body weight in the IMR5 metastatic model (FIG. 15B).

SEQUENCE LISTING

Figure 1A:
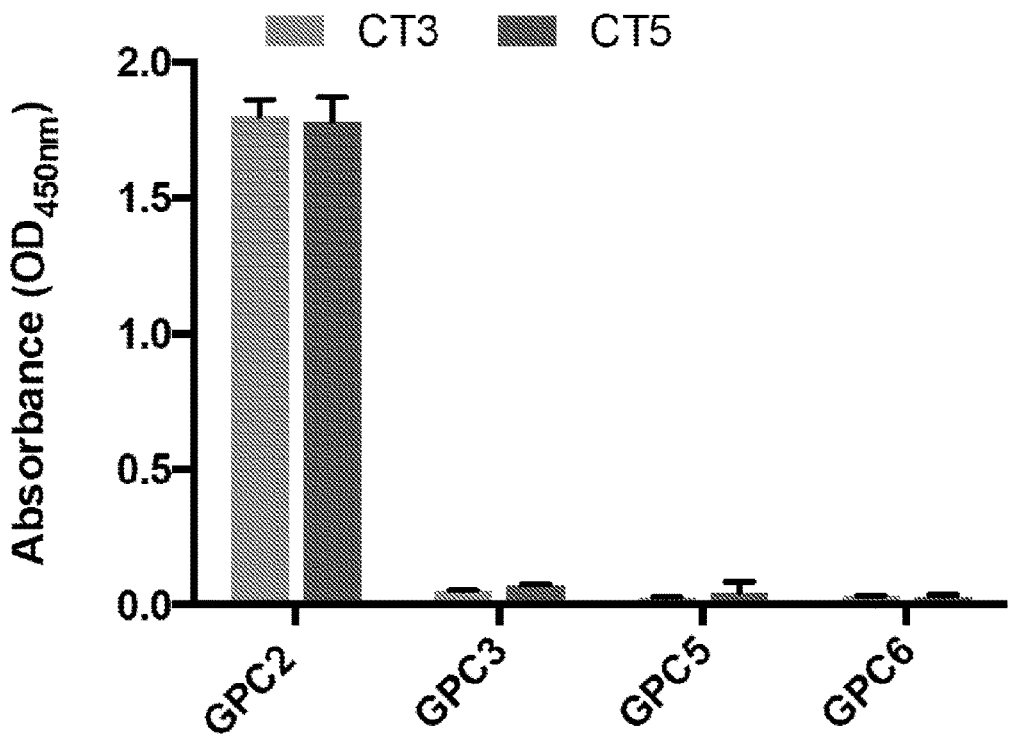
FIG. 1A: ELISA analysis of CT3 and CT5 binding to GPC2 and other glypican proteins. Both antibodies specifically bind GPC2.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 1, 2021, 28.6 KB, which is incorporated by reference herein. In the accompanying sequence listing:

SEQ ID NO: 1 is the nucleotide sequence of the CT3 VH domain.
SEQ ID NO: 2 is the amino acid sequence of the CT3 VH domain.
SEQ ID NO: 3 is the nucleotide sequence of the CT3 VL domain.
SEQ ID NO: 4 is the amino acid sequence of the CT3 VL domain.
SEQ ID NO: 5 is the nucleotide sequence of the CT5 VH domain.
SEQ ID NO: 6 is the amino acid sequence of the CT5 VH domain.
SEQ ID NO: 7 is the nucleotide sequence of the CT5 VL domain.
SEQ ID NO: 8 is the amino acid sequence of the CT5 VL domain.
SEQ ID NO: 9 is the amino acid sequence of the CT3 scFv.
SEQ ID NO: 10 is the amino acid sequence of a humanized CT3 scFv (hCT3-1).
SEQ ID NO: 11 is the amino acid sequence of a humanized CT3 scFv (hCT3-2).
SEQ ID NO: 12 is the amino acid sequence of the sCT3 scFv comprising the CDR sequences of CT3 and framework sequences from murine antibody SS1.
SEQ ID NO: 13 is the amino acid sequence of a peptide neo-epitope.
SEQ ID NO: 14 is the amino acid sequence of the GM-CSF receptor signal sequence.
SEQ ID NO: 15 is the amino acid sequence of the CD8α hinge region.
SEQ ID NO: 16 is the amino acid sequence of the CD8α transmembrane domain.
SEQ ID NO: 17 is the amino acid sequence of 4-1BB.
SEQ ID NO: 18 is the amino acid sequence of CD3ζ.
SEQ ID NO: 19 is the amino acid sequence of the T2A self-cleaving peptide sequence.
SEQ ID NO: 20 is the amino acid sequence of truncated human epidermal growth factor receptor (huEGFRt).
SEQ ID NO: 21 is the amino acid sequence of a humanized CT3 scFv (hCT3-3).
SEQ ID NO: 22 is an amino acid sequence of PE38.
SEQ ID NO: 23 is an amino acid sequence of T20.

DETAILED DESCRIPTION

I. Abbreviations

ADC antibody-drug conjugate
ADCC antibody-dependent cell-mediated cytotoxicity
CAR chimeric antigen receptor
CDR complementarity determining region
CTL cytotoxic T lymphocyte
EF1α elongation factor 1 alpha
EGF epidermal growth factor
EGFR epidermal growth factor receptor
ELISA enzyme-linked immunosorbent assay
FACS fluorescence activated cells sorting
GMCSFRss granulocyte-macrophage colony stimulating factor receptor signal sequence
GPC2 glypican-2
GPI glycosylphosphatidylinositol
hFc human Fc
huEGFRt human truncated epidermal growth factor receptor
Ig immunoglobulin
IL interleukin
i.p. intraperitoneal
i.v. intravenous
mFc murine Fc
PE *Pseudomonas* exotoxin
s.c. subcutaneous
scFv single chain variable fragment
VH or $V_H$ variable heavy
VL or $V_L$ variable light

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

4-1BB: A co-stimulatory molecule expressed by T cell receptor (TCR)-activated lymphocytes, and by other cells including natural killer cells. Ligation of 4-1BB induces a signaling cascade that results in cytokine production, expression of anti-apoptotic molecules and an enhanced immune response. An exemplary amino acid sequence of 4-1BB is set forth herein as SEQ ID NO: 17.

Acute lymphoblastic leukemia (ALL): An acute form of leukemia characterized by the overproduction of lymphoblasts. ALL is most common in childhood, peaking at ages 2-5.

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the VH region and the VL region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., JMB 273,927-948, 1997; the "Chothia" numbering scheme), Kunik et al. (see Kunik et al., *PLoS Comput Biol* 8:e1002388, 2012; and Kunik et al., *Nucleic Acids Res* 40 (Web Server issue):W521-524, 2012; "Paratome CDRs") and the ImMunoGeneTics (IMGT) database (see, Lefranc, *Nucleic Acids Res* 29:207-9, 2001; the "IMGT" numbering scheme). The Kabat, Paratome and IMGT databases are maintained online.

A "single-domain antibody" refers to an antibody having a single domain (a variable domain) that is capable of specifically binding an antigen, or an epitope of an antigen, in the absence of an additional antibody domain. Single-domain antibodies include, for example, VH domain antibodies, $V_{NAR}$ antibodies, camelid $V_HH$ antibodies, and $V_L$ domain antibodies. $V_{NAR}$ antibodies are produced by cartilaginous fish, such as nurse sharks, wobbegong sharks, spiny dogfish and bamboo sharks. Camelid $V_HH$ antibodies are produced by several species including camel, llama, alpaca, dromedary, and guanaco, which produce heavy chain antibodies that are naturally devoid of light chains.

A "monoclonal antibody" is an antibody produced by a single clone of lymphocytes or by a cell into which the coding sequence of a single antibody has been transfected. Monoclonal antibodies are produced by methods known to those of skill in the art. Monoclonal antibodies include humanized monoclonal antibodies.

A "chimeric antibody" has framework residues from one species, such as human, and CDRs (which generally confer antigen binding) from another species.

A "humanized" antibody is an immunoglobulin including a human framework region and one or more CDRs from a non-human (for example a mouse, rabbit, rat, shark or synthetic) immunoglobulin. The non-human immunoglobulin providing the CDRs is termed a "donor," and the human immunoglobulin providing the framework is termed an "acceptor." In one embodiment, all CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A humanized antibody binds to the same antigen as the donor antibody that provides the CDRs. Humanized or other monoclonal antibodies can have additional conservative amino acid substitutions which have substantially no effect on antigen binding or other immunoglobulin functions.

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In other embodiments, antibody affinity is measured by flow cytometry or by surface plasmon reference. An antibody that "specifically binds" an antigen (such as GPC2) is an antibody that binds the antigen with high affinity and does not significantly bind other unrelated antigens.

Bispecific antibody: A recombinant protein that includes antigen-binding fragments of two different monoclonal antibodies, and is thereby capable of binding two different antigens. In some embodiments, bispecific antibodies are used for cancer immunotherapy by simultaneously targeting, for example, both CTLs (such as a CTL receptor component such as CD3) or effector natural killer (NK) cells, and a tumor antigen. Similarly, a multi-specific antibody is a recombinant protein that includes antigen-binding fragments of at least two different monoclonal antibodies, such as two, three or four different monoclonal antibodies.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neuroblastoma. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds GPC2 used in combination with a radioactive or chemical compound.

Chimeric antigen receptor (CAR): A chimeric molecule that includes an antigen-binding portion (such as a scFv) and a signaling domain, such as a signaling domain from a T cell receptor (e.g. CD3ζ). Typically, CARs are comprised of an antigen-binding moiety, a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody. The light and heavy chains of a mammalian immunoglobulin each have three CDRs, designated L-CDR1, L-CDR2, L-CDR3 and H-CDR1, H-CDR2, H-CDR3, respectively.

Conjugate: In the context of the present disclosure, a "conjugate" is an antibody or antibody fragment (such as an antigen-binding fragment) covalently linked to an effector molecule or a second protein (such as a second antibody). The effector molecule can be, for example, a drug, toxin, therapeutic agent, detectable label, protein, nucleic acid, lipid, nanoparticle, carbohydrate or recombinant virus. An antibody conjugate is often referred to as an "immunoconjugate." When the conjugate comprises an antibody linked to a drug (e.g., a cytotoxic agent), the conjugate is often referred to as an "antibody-drug conjugate" or "ADC." Other antibody conjugates include, for example, multi-specific (such as bispecific or trispecific) antibodies and chimeric antigen receptors (CARs).

Conservative variant: "Conservative" amino acid substitutions are those substitutions that do not substantially affect or decrease the affinity of a protein, such as an antibody to GPC2. For example, a monoclonal antibody that specifically binds GPC2 can include at most about 1, at most about 2, at most about 5, and most about 10, or at most about 15 conservative substitutions and specifically bind the GPC2 polypeptide. The term "conservative variant" also includes the use of a substituted amino acid in place of an unsubstituted parent amino acid, provided that antibody specifically binds GPC2. Non-conservative substitutions are those that reduce an activity or binding to GPC2.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxic agent: Any drug or compound that kills cells.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Desmoplastic small round cell tumor (DRCT): A soft tissue sarcoma that predominantly occurs in childhood, particularly in boys. DRCT is an aggressive and rare type of cancer that primarily occurs as a masses in the abdomen, but can also be found in the lymph nodes, the lining of the abdomen, diaphragm, spleen, liver, chest wall, skull, spinal cord, intestine, bladder, brain, lungs, testicles, ovaries and the pelvis.

Diagnostic: Identifying the presence or nature of a pathologic condition, such as neuroblastoma. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as neuroblastoma.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms. Therapeutic agents (or drugs) include such compounds as nucleic acids, proteins, peptides, amino acids or derivatives, glycoproteins, radio-isotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-GPC2 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e., that elicit a specific immune response. An antibody specifically binds a particular antigenic epitope on a polypeptide, such as GPC2.

Ewing's sarcoma: A rare type of malignant tumor found in bone or soft tissue. Ewing's sarcoma is a small, blue, round cell tumor.

Framework region: Amino acid sequences interposed between CDRs. Framework regions include variable light and variable heavy framework regions. The framework regions serve to hold the CDRs in an appropriate orientation for antigen binding.

Fusion protein: A protein comprising at least a portion of two different (heterologous) proteins.

Glypican-2 (GPC2): A member of the six-member glypican family of heparan sulfate (HS) proteoglycans that are attached to the cell surface by a GPI anchor (Filmus et al., *Genome Biol* 9:224, 2008). GPC2 is uniquely expressed in the nervous system (Stipp et al., *J Cell Biol* 124:149-160, 1994), participates in cell adhesion and is thought to regulate the growth and guidance of axons. In addition, GPC2 mRNA is highly expressed in neuroblastoma and other pediatric cancers (Orentas et al., *Front Oncol* 2:194, 2012). GPC2 is also known as cerebroglycan proteoglycan and glypican proteoglycan 2. GPC2 genomic, mRNA and protein sequences are publically available (see, for example, NCBI Gene ID 221914).

GPC2-positive cancer: A cancer that overexpresses GPC2. Examples of GPC2-positive cancers include, but are not limited to, neuroblastoma, medulloblastoma, retinoblastoma, acute lymphoblastic leukemia, embryonal rhabdomyosarcoma, alveolar rhabdomyosarcoma, Ewing's sarcoma, desmoplastic small round cell tumor or osteosarcoma.

Heterologous: Originating from a separate genetic source or species.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunoliposome: A liposome with antibodies or antibody fragments conjugated to its surface Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody (such as one provided herein) or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins may be used. Examples of labels for polypeptides include, but are not limited to, the following: radioisotopes or radionucleotides (such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Medulloblastoma: A fast-growing type of cancer that forms in the cerebellum. Medulloblastomas tend to spread through the cerebrospinal fluid to the spinal cord or to other parts of the brain. They may also spread to other parts of the body, but this is rare. Medulloblastomas are most common in children and young adults. They are a type of central nervous system embryonal tumor.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Neuroblastoma: A solid tumor arising from embryonic neural crest cells. Neuroblastoma commonly arises in and around the adrenal glands, but can occur anywhere that sympathetic neural tissue is found, such as in the abdomen, chest, neck or nerve tissue near the spine. Neuroblastoma typically occurs in children younger than 5 years of age.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Osteosarcoma: A type of cancerous tumor found in the bone. Osteosarcoma is an aggressive cancer arising from primitive transformed cells of mesenchymal origin. This type of cancer is most prevalent in children and young adults.

Pediatric cancer: A cancer that develops in children ages 0 to 14. The major types of pediatric cancers include, for example, neuroblastoma, acute lymphoblastic leukemia (ALL), embryonal rhabdomyosarcoma (ERMS), alveolar rhabdomyosarcoma (ARMS), Ewing's sarcoma, desmoplastic small round cell tumor (DRCT), osteosarcoma, brain and other CNS tumors (such as medulloblastoma), Wilm's tumor, non-Hodgkin lymphoma, and retinoblastoma.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Retinoblastoma: A type of cancer that forms in the tissues of the retina. Retinoblastoma usually occurs in children younger than 5 years. It may be hereditary or nonhereditary (sporadic).

Rhabdomyosarcoma (RMS): A soft tissue malignant tumor of skeletal muscle origin. The most common primary sites for rhabdomyosarcoma are the head and neck (e.g., parameningeal, orbit, pharyngeal, etc.), the genitourinary tract, and the extremities. Other less common primary sites include the trunk, chest wall, the abdomen (including the retroperitoneum and biliary tract), and the perineal/anal region. There are at least two types of RMS; the most common forms are alveolar RMS (ARMS) and embryonal histological RMS (ERMS). Approximately 20% of children with rhabdomyosarcoma have the ARMS subtype. An increased frequency of this subtype is noted in adolescents and in patients with primary sites involving the extremities, trunk, and perineum/perianal region. ARMS is associated with chromosomal translocations encoding a fusion gene involving FKHR on chromosome 13 and members of the PAX family. The embryonal subtype is the most frequently observed subtype in children, accounting for approximately 60-70% of rhabdomyosarcomas of childhood. Tumors with embryonal histology typically arise in the head and neck region or in the genitourinary tract, although they may occur at any primary site. ERMS is characterized by a younger age at diagnosis, loss of heterozygosity, and altered genomic imprinting.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a VH of an antibody that specifically binds a GPC2 polypeptide are typically characterized by possession of at least about 75%, for example at least about 80%, 90%, 95%, 96%, 97%, 98% or 99% sequence identity counted over the full-length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Synthetic: Produced by artificial means in a laboratory, for example a synthetic nucleic acid or protein (for example, an antibody) can be chemically synthesized in a laboratory.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. In some embodiments, the vector is a virus vector, such as a lentivirus vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Monoclonal Antibodies Specific for Glypican-2 (GPC2)

Disclosed herein are high affinity anti-GPC2 monoclonal antibodies. Antibodies CT3 and CT5 were isolated from a mouse hybridoma and found to specifically bind GPC2; these antibodies do not other proteins of the glypican family. The anti-GPC2 antibodies bind GPC2-positive neuroblastoma, medulloblastoma and retinoblastoma tumor cells, but not normal (healthy) tissues. CARs based on the GPC2-specific antibodies exhibited superior killing of GPC2-expressing neuroblastoma tumor cells Immunotoxins based on engineered CT3 antibody inhibited proliferation of multiple GPC2-expressing cell lines. Specificity of the disclosed antibodies for GPC2 and GPC2-expressing tumors makes these antibodies excellent therapeutics for the treatment of pediatric cancers, including neuroblastoma, medulloblastoma and retinoblastoma. The disclosed antibodies are also useful for the detection of GPC2-expressing cells and the diagnosis of GPC2-positive tumors.

The nucleotide and amino acid sequences of the VH and VL domain of CT3 and CT4 are provided below and set forth herein as SEQ ID NOs: 1-8. Tables 1-4 list the amino acid positions of CDR1, CDR2 and CDR3 as determined using either Kabat, IMGT, or Paratome, or a combination of all three. One of skill in the art could readily determine the CDR boundaries using an alternative numbering scheme, such as the Chothia numbering scheme.

CT3 $V_H$ DNA (SEQ ID NO: 1)
GAGGTCCAGCTGCAACAGTCTGGACCTGAACTGGTGAAGCCTGGGGCTT
CAGTAAAGATGTCCTGCAAGGCTTCTAGATTCACATTCACTGACTACAA
CATACACTGGGTGAAGCAGAGCCCTGGAAAGACCCTTGAATGGATTGGA
TATATTAACCCTAACAATGGTGATATTTTCTACAAACAGAAGTTCAATG
GCAAGGCCACATTGACTATAAACAAGTCCTCCAACACAGCCTACATGGA
GCTCCGCAGCCTGACATCGGAGGATTCTGCAGTCTATTACTGTGTAAGA
TCCTCTAATATTCGTTATACTTTCGACAGGTTCTTCGATGTCTGGGGCA
CAGGGACCACGGTCACCGTCTCCTCA

CT3 $V_H$ Protein (SEQ ID NO: 2)
EVQLQQSGPELVKPGASVKMSCKASRFTFTDYNIHWVKQSPGKTLEWIG
YINPNNGDIFYKQKFNGKATLTINKSSNTAYMELRSLTSEDSAVYYCVR
SSNIRYTFDRFFDVWGTGTTVTSS

TABLE 1

Locations of the CDRs in the CT3 VH domain (SEQ ID NO: 2)

| Scheme | CDR1 | CDR2 | CDR3 |
|---|---|---|---|
| Kabat | 31-35 | 50-66 | 99-112 |
| IMGT | 26-33 | 51-58 | 97-112 |
| Paratome | 26-35 | 47-61 | 97-112 |
| Combined | 26-35 | 47-66 | 97-112 |

CT3 $V_L$ DNA (SEQ ID NO: 3)
GAAAATGTGCTCACCCAGTCTCCAGCAATCATGTCTGCATCTCTAGGGG
AGAAGGTCACCATGAGCTGCAGGGCCAGCTCAAGTGTAAATTACATTTA
CTGGTACCAGCAGAAGTCAGATGCCTCCCCCAAACTATGGATTTATTAC
ACATCCAACCTGGCTCCTGGAGTCCCAGCTCGCTTCAGTGGCAGTGGGT
CTGGGAACTCTTATTCTCTCACAATCAGCAGCATGGAGGGTGAAGATGC
TGCCACTTATTACTGCCAGCAGTTTTCTAGTTCCCCATCCACGTTCGGT
ACTGGGACCAAGCTGGAGCTGAAA

CT3 $V_L$ Protein (SEQ ID NO: 4)
ENVLTQSPAIMSASLGEKVTMSCRASSSVNYIYWYQQKSDASPKLWIYY
TSNLAPGVPARFSGSGSGNSYSLTISSMEGEDAATYYCQQFSSSPSTFG
TGTKLELK

TABLE 2

Locations of the CDRs in the CT3 VL domain (SEQ ID NO: 4)

| Scheme | CDR1 | CDR2 | CDR3 |
|---|---|---|---|
| Kabat | 24-33 | 49-55 | 88-96 |
| IMGT | 27-31 | 49-51 | 88-96 |
| Paratome | 27-33 | 45-55 | 88-95 |
| Combined | 24-33 | 45-55 | 88-96 |

CT5 $V_H$ DNA (SEQ ID NO: 5)
GAGGTGAAACTGGTGGAGTCTGGAGGAGGCTTGGTACAGTCTGGGCGTT
CTCTGAGACTCTCCTGTGCAACTTCTGGATTCACCTTCAGTGATTTCTA
CATGGAGTGGGTCCGCCAAGCTCCAGGGAAGGGACTGGAGTGGATTGTT
GCAAGTAGAGACAAAGCTAATGATTATACAACAGCGTATAGTGCATCTG
TGAAGGGTCGGTTCATCGTCTCCAGAGACACTTCCCAAAGCATCCTCTA
CCTTCAGATGAATGCCCTGAGAGCTGAGGACACTGCCATTTATTACTGT
GTAAGAGATTTCTATGATTACGACGAGGCTTACTGGGGCCAAGGGACTC
TGGTCACTGTCTCT

CT5 $V_H$ Protein (SEQ ID NO: 6)
EVKLVESGGGLVQSGRSLRLSCATSGFTFSDFYMEWVRQAPGKGLEWIV
ASRDKANDYTTAYSASVKGRFIVSRDTSQSILYLQMNALRAEDTAIYYC
VRDFYDYDEAYWGQGTLVTVS

TABLE 3

Locations of the CDRs in the CT5 VH domain (SEQ ID NO: 6)

| Scheme | CDR1 | CDR2 | CDR3 |
|---|---|---|---|
| Kabat | 31-35 | 50-68 | 101-109 |
| IMGT | 26-33 | 51-60 | 99-109 |
| Paratome | 27-35 | 47-62 | 99-109 |
| Combined | 26-35 | 47-68 | 99-109 |

CT5 V_L DNA
(SEQ ID NO: 7)
GACATCCAGATGACTCAGTCTCCGTCCTCACTGTCTGCCTCTCTGGGAG
GTACAGTCACCATCACTTGCAAGGCAAGCGAAGACATTAACAACTATAT
AGCTTGGTACCAACACAAGCCTGGAAAAGGTCCTCGGCTGCTCATACAA
TACACATCTACATTACAGCCAGGCATCCCATCAAGGTTCAGTGGAAGTG
GGTCTGGGCGAGATTATTCCCTCAGCATCAGCAACCTGGAGCCTGAAGA
TATTGCAACTTATTATTGTCTACAGTATGATATTCTGTGGACGTTCGGT
GGAGGCACCAAGCTGGAAATCAAA

CT5 V_L Protein
(SEQ ID NO: 8)
DIQMTQSPSSLSASLGGTVTITCKASEDINNYIAWYQHKPGKGPRLLIQ
YTSTLQPGIPSRFSGSGSGRDYSLSISNLEPEDIATYYCLQYDILWTFG
GGTKLEIK

TABLE 4

Locations of the CDRs in the CT5 VL domain (SEQ ID NO: 8)

| Scheme | CDR1 | CDR2 | CDR3 |
| --- | --- | --- | --- |
| Kabat | 24-34 | 50-56 | 89-96 |
| IMGT | 27-32 | 50-52 | 89-96 |
| Paratome | 27-34 | 46-56 | 89-95 |
| Combined | 24-34 | 46-56 | 89-96 |

Also disclosed herein are scFv molecules based on CT3. In the amino acid sequences below, the combined Kabat/IMGT/Paratome CDRs are shown in bold, framework residues are in normal font and a $(G_3S)_4$ linker sequence located between VH and VL domains is underlined. The CT3 scFv includes both CDR and framework sequences from the original CT3 antibody. The hCT3-1, hCT3-2 and hCT3-3 scFv molecules include the CDR sequences of CT3 and human framework sequences. The sCT3 scFv includes the CDR sequences of CT3 and framework sequences from murine antibody SS1 (see U.S. Pat. No. 6,809,184; Chowdhury and Pastan, *Nat Biotechnol* 17:568-572, 1999; Pastan et al., *Nat Rev Cancer* 6:559-565, 2006).

CT3 scFv
(SEQ ID NO: 9)
EVQLQQSGPELVKPGASVKMSCKASRFTFTDYNIHWVKQSPGKTLEWIG
YINPNNGDIFYKQKFNGKATLTINKSSNTAYMELRSLTSEDSAVYYCVR
SSNIRYTFDRFFDVWGTGTTVTVSSGGGGSGGGGSGGGGSENVLTQSPA
IMSASLGEKVTMSCRASSSVNYIYWYQQKSDASPKLWIYYTSNLAPGVP
ARFSGSGSGNSYSLTISSMEGEDAATYYCQQFSSSPSTFGTGTKLELK
Bold = combined Kabat/IMGT/Paratome CDRs
Underline = linker
Normal font = CT3 framework hCT3-1 scFv
(SEQ ID NO: 10)
QVQLVQSGAEVKKPGASVKVSCKASRFTFTDYNIHWVRQAPGQGLEWIG
YINPNNGDIFYKQKFNGRVTLTADKSTSTAYMELSSLTSEDTAVYYCVR
SSNIRYTFDRFFDVWGQGTLVTVSGGGGSGGGGSGGGGSDVVMTQSPLS
LPVTPGEPASISCRASSSVNYIYWYLQKPGQSPQLWIYYTSNLAPGVPD
RFSGSGSGTDFTLKISRVEAEDVGVYYCQQFSSSPSTFGQGTKLEIK
Bold = combined Kabat/IMGT/Paratome CDRs
Underline = linker
Normal font = human framework hCT3-2 scFv
(SEQ ID NO: 11)
QVQLVQSGAEVKKPGASVKVSCKASRFTFTDYNIHWVRQAPGQRLEWIG
YINPNNGDIFYKQKFNGRVTITRDTSASTAYMELSSLRSEDTAVYYCVR
SSNIRYTFDRFFDVWGQGTLVTVSGGGGSGGGGSGGGGSDVVMTQSPAF
LSVTPGEKVTITCRASSSVNYIYWYQQKPDQAPKLWIYYTSNLAPGVPS
RFSGSGSGTDFTFTISSLEAEDAATYYCQQFSSSPSTFGQGTKLEIK
Bold = combined Kabat/IMGT/Paratome CDRs
Underline = linker
Normal font = human framework hCT3-3 scFv
(SEQ ID NO: 21)
QVQLVQSGAEVKKPGASVKVSCKASRFTFTDYNIHWVRQAPGQGLEWIG
YINPNNGDIFYKQKFNGKATMTVDTSTSTVYMELSSLRSEDTAVYYCVR
SSNIRYTFDRFFDVWGQGTLVTVSGGGGSGGGGSGGGGSDIQMTQSPSS
LSASVGDRVTITCRASSSVNYIYWYQQKSGKAPKLWIYYTSNLAPGVPS
RFSGSGSGTDFTLTISSLQPEDFATYYCQQFSSSPSTFGQGTKLEIK
Bold = combined Kabat/IMGT/Paratome CDRs
Underline = linker
Normal font = human framework sCT3 (CT3 with SS1 framework; SEQ ID NO: 12)
MQVQLQQSGPELEKPGASVKISCKASRFTFTDYNIHWVKQSHGKCLEWI
GYINPNNGDIFYKQKFNGKATLTVDKSSSTAYMDLLSLTSEDSAVYFCV
RSSNIRYTFDRFFDVWGQGTTVTVSSGGGGSGGGGSGGGGSDIELTQSP
AIMSASPGEKVTMTCRASSSVNYIYWYQQKSGTSPKLWIYYTSNLAPGV
PGRFSGSGSGNSYSLTISSVEAEDDATYYCQQFSSSPSTFGCGTKLEIK
Bold = combined Kabat/IMGT/Paratome CDRs
Underline = linker
Normal font = SS1 (murine) framework Provided herein are isolated monoclonal antibodies, or antigen-binding fragments thereof, that bind (such as specifically bind) GPC2. The monoclonal antibodies or antigen-binding fragments include a variable heavy (VH) domain and a variable light (VL) domain. In some embodiments, the monoclonal antibodies or antigen-binding fragments include at least a portion of the amino acid sequence set forth herein as SEQ ID NO: 2, SEQ ID NO: 4, SEQ ID NO: 6 or SEQ ID NO: 8, such as one or more (such as all three) CDR sequences from SEQ ID NO: 2, SEQ ID NO: 4, SEQ ID NO: 6 or SEQ ID NO: 8. In some examples, the CDR locations are determined IMGT, Kabat, Paratome, Chothia, or a combination of one or more thereof.

In some embodiments, the VH domain of the antibody (or antigen-binding fragment) comprises the CDR sequences of SEQ ID NO: 2 and the VL domain of the antibody (or antigen-binding fragment thereof) comprises the CDR sequences of SEQ ID NO: 4. In some examples, the CDR sequences are determined using the Kabat, IMGT, Paratome or Chothia numbering scheme, or a combination thereof. In particular examples, the CDR sequences are determined using a combination of Kabat, IMGT and Paratome.

In some embodiments, the VH domain of the antibody (or antigen-binding fragment) comprises the CDR sequences of SEQ ID NO: 6 and the VL domain of the antibody (or antigen-binding fragment thereof) comprises the CDR sequences of SEQ ID NO: 8. In some examples, the CDR sequences are determined using the Kabat, IMGT, Paratome or Chothia numbering scheme, or a combination thereof. In particular examples, the CDR sequences are determined using a combination of Kabat, IMGT and Paratome.

In some embodiments, the VH domain of the antibody or antigen-binding fragment comprises residues 31-35, 50-66 and 99-112 of SEQ ID NO: 2. In some embodiments, the VL domain of the antibody or antigen-binding fragment comprises residues 24-33, 49-55 and 88-96 of SEQ ID NO: 4. In some examples, the VH domain comprises residues 31-35, 50-66 and 99-112 of SEQ ID NO: 2 and the VL domain comprises residues 24-33, 49-55 and 88-96 of SEQ ID NO: 4.

In some embodiments, the VH domain of the antibody or antigen-binding fragment comprises residues 31-35, 50-68 and 101-109 of SEQ ID NO: 6. In some embodiments, the VL domain of the antibody or antigen-binding fragment comprises residues 24-34, 50-56 and 89-96 of SEQ ID NO: 8. In some examples, the VH domain comprises residues 31-35, 50-68 and 101-109 of SEQ ID NO: 6 and the VL domain comprises residues 24-34, 50-56 and 89-96 of SEQ ID NO: 8.

In some embodiments, the VH domain of the antibody or antigen-binding fragment comprises residues 26-33, 51-58 and 97-112 of SEQ ID NO: 2. In some embodiments, the VL domain of the antibody or antigen-binding fragment comprises residues 27-31, 49-51 and 88-96 of SEQ ID NO: 4. In some examples, the VH domain comprises residues 26-33, 51-58 and 97-112 of SEQ ID NO: 2 and the VL domain comprises residues 27-31, 49-51 and 88-96 of SEQ ID NO: 4.

In some embodiments, the VH domain of the antibody or antigen-binding fragment comprises residues 26-33, 51-60 and 99-109 of SEQ ID NO: 6. In some embodiments, VL domain of the antibody or antigen-binding fragment comprises residues 27-32, 50-52 and 89-96 of SEQ ID NO: 8. In some examples, the VH domain comprises residues 26-33, 51-60 and 99-109 of SEQ ID NO: 6 and the VL domain comprises residues 27-32, 50-52 and 89-96 of SEQ ID NO: 8.

In some embodiments, the VH domain of the antibody or antigen-binding fragment comprises residues 26-35, 47-61 and 97-112 of SEQ ID NO: 2. In some embodiments, the VL domain of the antibody or antigen-binding fragment comprises residues 27-33, 45-55 and 88-95 of SEQ ID NO: 4. In some examples, the VH domain comprises residues 26-35, 47-61 and 97-112 of SEQ ID NO: 2 and the VL domain comprises residues 27-33, 45-55 and 88-95 of SEQ ID NO: 4.

In some embodiments, the VH domain of the antibody or antigen-binding fragment comprises residues 27-35, 47-62 and 99-109 of SEQ ID NO: 6. In some embodiments, the VL domain of the antibody or antigen-binding fragment comprises residues 27-34, 46-56 and 89-95 of SEQ ID NO: 8. In some examples, the VH domain comprises residues 27-35, 47-62 and 99-109 of SEQ ID NO: 6 and the VL domain comprises residues 27-34, 46-56 and 89-95 of SEQ ID NO: 8.

In some embodiments, the VH domain of the antibody or antigen-binding fragment comprises residues 26-35, 47-66 and 97-112 of SEQ ID NO: 2. In some embodiments, the VL domain of the antibody or antigen-binding fragment comprises residues 24-33, 45-55 and 88-96 of SEQ ID NO: 4. In some examples, the VH domain comprises residues 26-35, 47-66 and 97-112 of SEQ ID NO: 2 and the VL domain comprises residues 24-33, 45-55 and 88-96 of SEQ ID NO: 4.

In some embodiments, the VH domain of the antibody or antigen-binding fragment comprises residues 26-35, 47-68 and 99-109 of SEQ ID NO: 6. In some embodiments, the VL domain of the antibody or antigen-binding fragment comprises residues 27-34, 46-56 and 89-96 of SEQ ID NO: 8. In some examples, the VH domain comprises residues 26-35, 47-68 and 99-109 of SEQ ID NO: 6 and the VL domain comprises residues 27-34, 46-56 and 89-96 of SEQ ID NO: 8.

In some embodiments, the amino acid sequence of the VH domain is at least 80%, at least 85%, at least 90%, at least 95%, at least 96%, at least 97%, at least 98% or at least 99% identical to SEQ ID NO: 2 and/or the amino acid sequence of the VL domain is at least 80%, at least 85%, at least 90%, at least 95%, at least 96%, at least 97%, at least 98% or at least 99% identical to SEQ ID NO: 4. In some examples, the amino acid sequence of the VH domain comprises or consists of SEQ ID NO: 2 and/or the amino acid sequence of the VL domain comprises or consists of SEQ ID NO: 4.

In some embodiments, the amino acid sequence of the VH domain is at least 80%, at least 85%, at least 90%, at least 95%, at least 96%, at least 97%, at least 98% or at least 99% identical to SEQ ID NO: 6 and/or the amino acid sequence of the VL domain is at least 80%, at least 85%, at least 90%, at least 95%, at least 96%, at least 97%, at least 98% or at least 99% identical to SEQ ID NO: 8. In some examples, amino acid sequence of the VH domain comprises or consists of SEQ ID NO: 6 and/or the amino acid sequence of the VL domain comprises or consists of SEQ ID NO: 8.

In some embodiments, the monoclonal antibody or antigen-binding fragment is a humanized, chimeric or synthetic monoclonal antibody or antigen-binding fragment.

In some examples, the monoclonal antibody is an IgG. In other examples, the monoclonal antibody is an IgA, IgD, IgE or IgM.

In some embodiments, the antigen-binding fragment is a single chain variable fragment (scFv), an Fab fragment, an Fab' fragment, an F(ab)'₂ fragment, or a disulfide stabilized variable fragment (dsFv). In some examples, the antigen-binding fragment is a scFv. In particular examples, the scFv comprises an amino acid sequence at least 80%, at least 85%, at least 90%, at least 95%, at least 96%, at least 97%, at least 98% or at least 99% identical to SEQ ID NO: 9, SEQ ID NO: 10, SEQ ID NO: 11, SEQ ID NO: 12 or SEQ ID NO: 21. In non-limiting examples, the scFv comprises or consists of the amino acid sequence of SEQ ID NO: 9, SEQ ID NO: 10, SEQ ID NO: 11, SEQ ID NO: 12 or SEQ ID NO: 21.

Also provided herein are chimeric antigen receptors (CARs) that include a monoclonal antibody or antigen-binding fragment disclosed herein. In some embodiments, the CAR further includes a hinge region, a transmembrane domain, a costimulatory signaling moiety, a signaling domain, or any combination thereof. Further provided are cells expressing a GPC2-specific CAR. In some examples, the cell is a T lymphocyte, such as a CTL. CARs and CAR-expressing T cells are further described in section V.

Also provided herein are immunoconjugates that include a monoclonal antibody or antigen-binding fragment disclosed herein and an effector molecule. In some embodiments, the effector molecule is a toxin, such as, but not limited to, *Pseudomonas* exotoxin or a variant thereof, such as PE38. In other embodiments, the effector molecule is a detectable label, such as, but not limited to, a fluorophore, an enzyme or a radioisotope. Immunoconjugates are further described in section IV.

Further provided herein are antibody-drug conjugates (ADCs) that include a drug conjugated to a monoclonal antibody or antigen-binding fragment disclosed herein. In some embodiments, the drug is a small molecule, for example an anti-microtubule agent, an anti-mitotic agent and/or a cytotoxic agent. ADCs are further described in section VI.

Also provided herein are multi-specific antibodies that include a monoclonal antibody or antigen-binding fragment disclosed herein and at least one additional monoclonal antibody or antigen-binding fragment thereof. In some embodiments, the multi-specific antibody is a bispecific antibody. In other embodiments, the multi-specific antibody is a trispecific antibody. In some embodiments, the at least one additional monoclonal antibody or antigen binding fragment thereof specifically binds a component of the T cell receptor or a natural killer (NK) cell activating receptor. Multi-specific antibodies are further described in section VII.

Further provided herein are antibody-nanoparticle conjugates that include a nanoparticle conjugated to a monoclonal antibody or antigen-binding fragment disclosed herein. In some embodiments, the nanoparticle comprises a polymeric nanoparticle, nanosphere, nanocapsule, liposome, dendrimer, polymeric micelle, or niosome. In some embodiments, the nanoparticle includes a cytotoxic agent. Antibody-nanoparticle conjugates are further described in section VIII.

Also provided herein are fusion proteins that include a monoclonal antibody or antigen-binding fragment disclosed herein and a heterologous protein or peptide. In some embodiments, the heterologous protein is an Fc protein. In some examples, the Fc protein is a mouse Fc or a human Fc protein. In some embodiments, the heterologous peptide is not endogenous to humans (for example, the heterologous peptide is a peptide neo-epitope).

Compositions that include a pharmaceutically acceptable carrier and a monoclonal antibody or antigen-binding fragment, CAR, isolated cell (such as a CAR expressing cell, for example a CAR T cell), immunoconjugate, ADC, multi-specific antibody, antibody-nanoparticle conjugate, or fusion protein disclosed herein are further provided by the present disclosure.

Also provided are nucleic acid molecules encoding a monoclonal antibody or antigen-binding fragment disclosed herein. Further provided are nucleic acid molecules encoding a CAR, immunoconjugate, multi-specific antibody, or fusion protein disclosed herein. In some embodiments, the nucleic acid molecule is operably linked to a promoter. Vectors that include the nucleic acid molecules are further provided herein.

In some embodiments, the nucleotide sequence of the VH domain is at least 80%, at least 85%, at least 90%, at least 95%, at least 96%, at least 97%, at least 98% or at least 99% identical to SEQ ID NO: 1. In some embodiments, the nucleotide sequence of the VL domain is at least 80%, at least 85%, at least 90%, at least 95%, at least 96%, at least 97%, at least 98% or at least 99% identical to SEQ ID NO: 3. In some examples, the nucleotide sequence of the VH domain comprises or consists of SEQ ID NO: 1 and the nucleotide sequence of the VL domain comprises of consists of SEQ ID NO: 3.

In some embodiments, the nucleotide sequence of the VH domain is at least 80%, at least 85%, at least 90%, at least 95%, at least 96%, at least 97%, at least 98% or at least 99% identical to SEQ ID NO: 5. In some embodiments, the nucleotide sequence of the VL domain is at least 80%, at least 85%, at least 90%, at least 95%, at least 96%, at least 97%, at least 98% or at least 99% identical to SEQ ID NO: 7. In some examples, the nucleotide sequence of the VH domain comprises or consists of SEQ ID NO: 5 and the nucleotide sequence of the VL domain comprises of consists of SEQ ID NO: 7.

In some embodiments, provided herein is a nucleic acid construct that expresses a CAR and a truncated human EGFR (huEGFRt). In some embodiments, the nucleic acid comprises in the 5' to 3' direction: a nucleic acid encoding a first granulocyte-macrophage colony stimulating factor receptor signal sequence (GMCSFRss); a nucleic acid encoding a GPC2-specific monoclonal antibody or antigen-binding fragment disclosed herein; a nucleic acid encoding an extracellular hinge region; a nucleic acid encoding a transmembrane domain; a nucleic acid encoding an intracellular co-stimulatory domain; a nucleic acid encoding a intracellular signaling domain; a nucleic acid encoding a self-cleaving 2A peptide; a nucleic acid encoding a second GMCSFRss; and a nucleic acid encoding a truncated human epidermal growth factor receptor (huEGFRt). In some examples, the nucleic acid further includes a human elongation factor 1α (EF1α) promoter sequence 5' of the nucleic acid encoding the first GMCSFRss. In some examples, the hinge region comprises a CD8α hinge region. In some examples, the transmembrane domain comprises a CD8α transmembrane domain. In some examples, the costimulatory signaling moiety comprises a 4-1BB signaling moiety. In some examples, the signaling domain comprises a CD3ζ signaling domain. In some examples, the antigen-binding fragment is a single-chain variable fragment (scFv). In particular non-limiting examples, the scFv comprises the amino acid sequence of SEQ ID NO: 9, SEQ ID NO: 10, SEQ ID NO: 11, SEQ ID NO: 12 or SEQ ID NO: 21.

Also provided is an isolated cell co-expressing a CPC2-specific CAR disclosed herein and huEGFRt. In some examples, the cell is a cytotoxic T lymphocyte (CTL).

IV. Immunoconjugates

The disclosed monoclonal antibodies can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect expression of a target antigen by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512, 658; 5,602,095; 5,608,039; 5,821,238; and 5,854,044; U.S. Patent Application Publication No. 2015/0099707; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), such as for one or more amino acid residues within one or more T-cell epitopes and/or B cell epitopes of PE, or deletion of one or more T-cell and/or B-cell epitopes (see, for example, U.S. Patent Application Publication No. 2015/0099707).

Contemplated forms of PE also include deimmunized forms of PE, for example versions with domain II deleted (for example, PE24). Deimmunized forms of PE are described in, for example, PCT Publication Nos. WO 2005/052006, WO 2007/016150, WO 2007/014743, WO 2007/031741, WO 2009/32954, WO 2011/32022, WO 2012/154530, and WO 2012/170617.

The antibodies described herein can also be used to target any number of different diagnostic or therapeutic compounds to cells expressing the tumor or viral antigen on their surface. Thus, an antibody of the present disclosure can be attached directly or via a linker to a drug that is to be delivered directly to cells expressing cell-surface antigen. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an antibody can be an encapsulation system, such as a nanoparticle, liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

V. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010; Dai et al., *J Natl Cancer Inst* 108(7):djv439, 2016). In many instances, the binding moiety is an antigen binding fragment of a monoclonal antibody, such as a scFv or single-domain antibody. The spacer/hinge region typically includes sequences from IgG subclasses, such as IgG1, IgG4, IgD and CD8 domains. The transmembrane domain can be can derived from a variety of different T cell proteins, such as CD3ζ, CD4, CD8 or CD28. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28, 4-1BB (CD137, TNFRSF9), OX-40 (CD134), ICOS, CD27 and/or DAP10.

CTLs expressing CARs can be used to target a specific cell type, such as a GPC2-positive tumor cell. Thus, the monoclonal antibodies disclosed herein can be used to engineer CTLs that express a CAR containing the GPC2-specific monoclonal antibody (or fragment thereof), thereby targeting the engineered CTLs to GPC2-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a GPC2-specific antibody. Also provided are isolated nucleic acid molecules and vectors encoding the CARs, and host cells, such as CTLs, expressing the CARs. CTLs expressing CARs comprised of a GPC2-specific monoclonal antibody can be used for the treatment of cancers that express GPC2. In some embodiments herein, the CAR is a bispecific CAR.

In some instances, it is desirable to regulate the activation and expansion of CAR-expressing T cells after they have been infused into a patient. Several strategies have been developed to module CAR-expressing T cells in vivo, including the use of antibody-based switches that mediate interactions between CAR-expressing T cells and targeted tumors cells, as described by Rodgers et al. (*Proc Natl Acad Sci USA* 113(4):E459-E468, 2016). The antibody-based switches are comprised of a tumor antigen-specific antibody that has been grafted with a peptide neo-epitope (PNE).

Switchable CAR T (sCAR-T) cells are designed to specifically bind the PNE. Since the sCAR-T cells do not bind endogenous antigens, the presence of the switch is required for its activation.

Thus, provided herein are antibody-based switches that include a GPC2-specific antibody disclosed herein fused to a heterologous peptide, such as a PNE. In some embodiments, the heterologous peptide is not endogenous to humans (for example, it is a peptide that is not found in the human proteome). In some examples, the heterologous peptide is about 8 amino acids to about 20 amino acids in length, such about 10 to about 18 amino acids in length, such as about 12 to about 16 amino acids in length, such as about 14 amino acids in length. In particular examples, the heterologous peptide is about 8, 9, 10, 11, 12, 13, 14, 15, 16, 17, 18, 19 or 20 amino acids in length. In a specific non-limiting example, the PNE comprises or consists of NYHLENEVARLKKL (SEQ ID NO: 13).

In some embodiments, the CAR includes a signal peptide sequence, e.g., N-terminal to the antigen binding domain. The signal peptide sequence can be any suitable signal peptide sequence, such as a signal sequence from granulocyte-macrophage colony-stimulating factor receptor (GMCSFR), immunoglobulin light chain kappa, or IL-2. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

In some embodiments, the CARs disclosed herein are expressed from a construct (such as from a lentivirus vector) that also expresses a truncated version of human EGFR (huEGFRt). The CAR and huEGFRt are separated by a self-cleaving peptide sequence (such as T2A) such that upon expression in a transduced cell, the CAR is cleaved from huEGFRt.

In some embodiments disclosed herein, the CAR constructs encode the following amino acid sequences, in the N-terminal to C-terminal direction:

```
GMCSFRss:
                                        (SEQ ID NO: 14)
MLLLVTSLLLCELPHPAFLLIP

NdeI: HM

Antigen-binding: a GPC2-specific scFv
(such as any one of SEQ ID NOs: 9-12)

SpeI: TS

CD8α hinge:
                                        (SEQ ID NO: 15)
TTTPAPRPPTPAPTIASQPLSLRPEACRPAAGGAVHTRGLDFACD CD8α TM:
                                        (SEQ ID NO: 16)
IYIWAPLAGTCGVLLLSLVIT 4-1BB:
                                        (SEQ ID NO: 17)
KRGRKKLLYIFKQPFMRPVQTTQEEDGCSCRFPEEEEGGCEL CD3ζ:
                                        (SEQ ID NO: 18)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR

T2A:
                                        (SEQ ID NO: 19)
EGRGSLLTCGDVEENPGP

GMCSFRss:
                                        (SEQ ID NO: 14)
MLLLVTSLLLCELPHPAFLLIP huEGFRt:
                                        (SEQ ID NO: 20)
RKVCNGIGIGEFKDSLSINATNIKHFKNCTSISGDLHILPVAFRGDSFT
HTPPLDPQELDILKTVKEITGFLLIQAWPENRTDLHAFENLEIIRGRTK
QHGQFSLAVVSLNITSLGLRSLKEISDGDVIISGNKNLCYANTINWKKL
FGTSGQKTKIISNRGENSCKATGQVCHALCSPEGCWGPEPRDCVSCRNV
SRGRECVDKCNLLEGEPREFVENSECIQCHPECLPQAMNITCTGRGPDN
CIQCAHYIDGPHCVKTCPAGVMGENNTLVWKYADAGHVCHLCHPNCTYG
CTGPGLEGCPTNGPKIPSIATGMVGALLLLLVVALGIGLFM
```

The human epidermal growth factor receptor is comprised of four extracellular domains, a transmembrane domain and three intracellular domains. The EGFR domains are found in the following N-terminal to C-terminal order: Domain I-Domain II-Domain III-Domain IV-transmembrane (TM) domain-juxtamembrane domain-tyrosine kinase domain-C-terminal tail. Domain I and Domain III are leucine-rich domains that participate in ligand binding. Domain II and Domain IV are cysteine-rich domains and do not make contact with EGFR ligands. Domain II mediates formation of homo- or hetero-dimers with analogous domains from other EGFR family members, and Domain IV can form disulfide bonds with Domain II. The EGFR™ domain makes a single pass through the cell membrane and may play a role in protein dimerization. The intracellular domain includes the juxtamembrane domain, tyrosine kinase domain and C-terminal tail, which mediate EGFR signal transduction (Wee and Wang, *Cancers* 9(52), doi:10.3390/cancers9050052; Ferguson, *Annu Rev Biophys* 37:353-373, 2008; Wang et al., *Blood* 118(5):1255-1263, 2011).

A truncated version of human EGFR, referred to herein as "huEGFRt" includes only Domain III, Domain IV and the TM domain. Thus, huEGFRt lacks Domain I, Domain II, and all three intracellular domains. huEGFRt is not capable of binding EGF and lacks signaling activity. However, this molecule retains the capacity to bind particular EGFR-specific monoclonal antibodies, such as FDA-approved cetuximab (PCT Publication No. WO 2011/056894, which is herein incorporated by reference).

Transduction of T cells with a construct (such as a lentivirus vector) encoding both huEGFRt and a tumor antigen-specific CAR disclosed herein allows for selection of transduced T cells using labelled EGFR monoclonal antibody cetuximab (ERBITUX™). For example, cetuximab can be labeled with biotin, and transduced T cells can be selected using anti-biotin magnetic beads, which are commercially available (such as from Miltenyi Biotec). Co-expression of huEGFRt also allows for in vivo tracking of adoptively transferred CAR-expressing T cells. Furthermore, binding of cetuximab to T cells expressing huEGFRt induces cytotoxicity of ADCC effector cells, thereby providing a mechanism to eliminate transduced T cells in vivo (Wang et al., *Blood* 118(5):1255-1263, 2011), such as at the conclusion of therapy.

VI. Antibody-Drug Conjugates (ADCs)

ADCs are compounds comprised of a tumor antigen-specific antibody (or antigen-binding fragment thereof) and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-ketogalactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) GPC2. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, vinca alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256, 746; 4,260,608; 4,265,814; 4,294,757; 4,307,016; 4,308, 268; 4,308,269; 4,309,428; 4,313,946; 4,315,929; 4,317, 821; 4,322,348; 4,331,598; 4,361,650; 4,364,866; 4,424, 219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663, 149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a GPC2-positive cancer alone or in combination with another therapeutic agent and/or in combination with any standard therapy for the treatment of cancer (such as surgical resection of the tumor, chemotherapy or radiation therapy).

VII. Multi-Specific Antibodies

Multi-specific antibodies are recombinant proteins comprised of antigen-binding fragments of two or more different monoclonal antibodies. For example, bispecific antibodies are comprised of antigen-binding fragments of two different monoclonal antibodies. Thus, bispecific antibodies bind two different antigens and trispecific antibodies bind three different antigens. Multi-specific antibodies can be used for cancer immunotherapy by simultaneously targeting, for example, both CTLs (such as a CTL receptor component such as CD3) or effector natural killer (NK) cells, and at least one tumor antigen. The GPC2-specific monoclonal antibodies disclosed herein can be used to generate multi-specific (such as bispecific or trispecific) antibodies that target both GPC2 and CTLs, or target both GPC2 and NK cells, thereby providing a means to treat GPC2-expressing cancers.

Bi-specific T-cell engagers (BiTEs) are a type of bispecific monoclonal antibody that are fusions of a first single-chain variable fragment (scFv) that targets a tumor antigen and a second scFv that binds T cells, such as bind CD3 on T cells. In some embodiments herein, one of the binding moieties of the BiTE (such as one of the scFv molecules) is specific for GPC2.

Bi-specific killer cell engagers (BiKEs) are a type of bispecific monoclonal antibody that are fusions of a first scFv that targets a tumor antigen and a second scFv that binds a NK cell activating receptor, such as CD16.

Provided herein are multi-specific, such as trispecific or bispecific, monoclonal antibodies comprising a GPC2-specific monoclonal antibody. In some embodiments, the multi-specific monoclonal antibody further comprises a monoclonal antibody, or antigen-binding fragment thereof, that specifically binds a component of the T cell receptor, such as CD3. In other embodiments, the multi-specific monoclonal antibody further comprises a monoclonal antibody, or antigen-binding fragment thereof, that specifically binds a NK cell activating receptor, such as CD16, Ly49, or CD94. Also provided are isolated nucleic acid molecules and vectors encoding the multi-specific antibodies, and host cells comprising the nucleic acid molecules or vectors. Multi-specific antibodies comprising a GPC2-specific antibody can be used for the treatment of cancers that express GPC2. Thus, provided herein are methods of treating a subject with cancer by selecting a subject with a cancer that expresses GPC2, and administering to the subject a therapeutically effective amount of the GPC2-targeting multi-specific antibody.

VIII. Antibody-Nanoparticle Conjugates

The monoclonal antibodies disclosed herein can be conjugated to a variety of different types of nanoparticles to deliver cytotoxic agents or other anti-cancer agents directly to tumor cells via binding of the antibody to a tumor specific antigen (e.g. GPC2) expressed on the surface of tumor cells. The use of nanoparticles reduces off-target side effects and can also improve drug bioavailability and reduce the dose of a drug required to achieve a therapeutic effect. Nanoparticle formulations can be tailored to suit the drug that is to be carried or encapsulated within the nanoparticle. For example, hydrophobic molecules can be incorporated inside the core of a nanoparticle, while hydrophilic drugs can be carried within an aqueous core protected by a polymeric or lipid shell. Examples of nanoparticles include, but at not limited to, nanospheres, nanocapsules, liposomes, dendrimers, polymeric micelles, niosomes, and polymeric nanoparticles (Fay and Scott, *Immunotherapy* 3(3):381-394, 2011).

Liposomes are currently one of the most common types of nanoparticles used for drug delivery. An antibody conjugated to a liposome is often referred to as an "immunoliposome." The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Niosomes are non-ionic surfactant-based vesicles having a structure similar to liposomes. The membranes of niosomes are composed only of nonionic surfactants, such as polyglyceryl-alkyl ethers or N-palmitoylglucosamine Niosomes range from small, unilamellar to large, multilamellar particles. These nanoparticles are monodisperse, water-soluble, chemically stable, have low toxicity, are biodegradable and non-immunogenic, and increase bioavailability of encapsulated drugs.

Dendrimers include a range of branched polymer complexes. These nanoparticles are water-soluble, biocompatible and are sufficiently non-immunogenic for human use. Generally, dendrimers consist of an initiator core, surrounded by a layer of a selected polymer that is grafted to the core, forming a branched macromolecular complex. Dendrimers are typically produced using polymers such as poly(amidoamine) or poly(L-lysine). Dendrimers have been used for a variety of therapeutic and diagnostic applications, including for the delivery of DNA, RNA, bioimaging contrast agents and chemotherapeutic agents.

Polymeric micelles are composed of aggregates of amphiphilic co-polymers (consisting of both hydrophilic and hydrophobic monomer units) assembled into hydrophobic cores, surrounded by a corona of hydrophilic polymeric chains exposed to the aqueous environment. In many cases, the polymers used to prepare polymeric micelles are heterobifunctional copolymers composed of a hydrophilic block of PEG, poly(vinyl pyrrolidone) and hydrophobic poly(L-lactide) or poly(L-lysine) that forms the particle core. Polymeric micelles can be used to carry drugs that have poor solubility. These nanoparticles have been used to encapsulate a number of anti-cancer drugs, including doxorubicin and camptothecin. Cationic micelles have also been developed to carry DNA or RNA molecules.

Polymeric nanoparticles include both nanospheres and nanocapsules. Nanospheres consist of a solid matrix of polymer, while nanocapsules contain an aqueous core. The formulation selected typically depends on the solubility of the therapeutic agent to be carried/encapsulated; poorly water-soluble drugs are more readily encapsulated within a nanospheres, while water-soluble and labile drugs, such as DNA and proteins, are more readily encapsulated within nanocapsules. The polymers used to produce these nanoparticles include, for example, poly(acrylamide), poly(ester), poly(alkylcyanoacrylates), poly(lactic acid) (PLA), poly (glycolic acids) (PGA), and poly(D,L-lactic-co-glycolic acid) (PLGA).

Antibodies (or fragments thereof) can be conjugated to a suitable nanoparticle according to standard methods known in the art. For example, conjugation can be either covalent or noncovalent. In some embodiments in which the nanoparticle is a liposome, the antibody is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies to nanoparticles (Paszko and Senge, *Curr Med Chem* 19(31) 5239-5277, 2012).

IX. Compositions and Methods of Use

Compositions are provided that include one or more of the disclosed monoclonal antibodies that bind (for example specifically bind) GPC2 in a carrier. Compositions comprising ADCs, CARs (and CTLs comprising CARs), multi-specific (such as bispecific or trispecific) antibodies, antibody-nanoparticle conjugates, immunoliposomes and immunoconjugates are also provided. The compositions can be prepared in unit dosage forms for administration to a subject. The amount and timing of administration are at the discretion of the treating clinician to achieve the desired outcome. The antibody, ADC, CAR, CTL, multi-specific antibody, antibody-nanoparticle conjugate, immunoliposome or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, multi-specific (such as bispecific or trispecific) antibody, antibody-nanoparticle conjugate, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, multi-specific antibody, antibody-nanoparticle conjugate, or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19*th ed.*, Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, ADCs, CARs, multi-specific (such as bispecific or trispecific) antibodies, antibody-nanoparticle conjugates, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include, for example, microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, multi-specific (such as bispecific or trispecific) antibodies, antibody-nanoparticle conjugates, immunoliposomes and immunoconjugates disclosed herein can be administered to slow or inhibit the growth of tumor cells or inhibit the metastasis of tumor cells, such as GPC2-positive cancers. In these applications, a therapeutically effective amount of a composition is administered to a subject in an amount sufficient to inhibit growth, replication or metastasis of cancer cells, or to inhibit a sign or a symptom of the cancer. Thus, in some examples, the disclosed methods reduce the size, weight and/or volume of a primary tumor and/or a metastasis by at least 20%, at least 25%, at least 50%, at least 75%, at least 80%, at least 90%, at last 95%, at least 99%, or even 100%. Thus, in some examples, the disclosed methods reduce the number of metastases by at least 20%, at least 25%, at least 50%, at least 75%, at least 80%, at least 90%, at last 95%, at least 99%, or even 100%. Suitable subjects may include those diagnosed with a cancer that expresses GPC2, such as, but not limited to neuroblastoma, medulloblastoma, retinoblastoma, acute lymphoblastic leukemia, embryonal rhabdomyosarcoma, alveolar rhabdomyosarcoma, Ewing's sarcoma, desmoplastic small round cell tumor or osteosarcoma.

Provided herein is a method of treating a GPC2-positive cancer in a subject by administering to the subject a therapeutically effective amount of a GPC2-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. Also provided herein is a method of inhibiting tumor growth or metastasis of a GPC2-positive cancer in a subject by administering to the subject a therapeutically effective amount of a GPC2-specific antibody, immunoconjugate, CAR (e.g. a CTL expressing a CAR), ADC, multi-specific (such as bispecific or trispecific) antibody, antibody-nanoparticle conjugate, immunoliposome or composition disclosed herein. In some embodiments, the GPC2-positive cancer is a neuroblastoma, medulloblastoma, retinoblastoma, acute lymphoblastic leukemia, embryonal rhabdomyosarcoma, alveolar rhabdomyosarcoma, Ewing's sarcoma, desmoplastic small round cell tumor or osteosarcoma.

A therapeutically effective amount of a GPC2-specific monoclonal antibody (or fragment thereof), ADC, CAR (e.g. a CTL expressing a CAR), multi-specific (such as bispecific or trispecific) antibody, immunoconjugate, immunoliposome or composition disclosed herein will depend upon the severity of the disease, the type of disease, and the general state of the patient's health. A therapeutically effective amount of the antibody-based composition is that which provides either subjective relief of a symptom(s) or an objectively identifiable improvement as noted by the clinician or other qualified observer.

Administration of the GPC2-specific antibodies, ADCs, CARs, immunoconjugates, multi-specific (such as bispecific or trispecific) antibodies, antibody-nanoparticle conjugates, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein (for example sequentially or concurrently). Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Non-limiting examples of other biologics (such as a monoclonal antibody) that can be used with the antibodies, compositions and immunoconjugates disclosed herein include an antibody that antagonizes PD-1 or PD-L1, such as Atezolizumab, MPDL3280A, BNS-936558 (Nivolumab), Pembrolizumab, Pidilizumab, CT011, AMP-224, AMP-514, MEDI-0680, BMS-936559, BMS935559, MEDI-4736, MPDL-3280A, MSB-0010718C, MGA-271, Indoximod, Epacadostat, BMS-986016, MEDI-4736, MEDI-4737, MK-4166, BMS-663513, PF-05082566 (PF-2566), Lirilumab, and Durvalumab. In some examples, the additional therapeutic agent administered is one or more of 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelimumab, Tucotuzumab celmoleukin, Veltuzumab, Volociximab, Votumumab, and Zalutumumab. Another exemplary treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

Also provided herein is a kit that includes a GPC2-specific monoclonal antibody or antigen-binding fragment, a CAR, an isolated cell, an immunoconjugate, an ADC, a multi-specific antibody, an antibody-nanoparticle conjugate, a fusion protein, or a composition disclosed herein, and a second therapeutic agent for treating cancer. In some examples, the second therapeutic agent is a radioactive or chemical compound.

B. Methods for Diagnosis and Detection

Methods are provided herein for detecting GPC2 protein in vitro or in vivo. In some cases, GPC2 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

Provided herein is a method of determining if a subject has a GPC2-positive cancer by contacting a sample from the subject with a GPC2-specific monoclonal antibody disclosed herein; and detecting binding of the antibody to the sample. An increase in binding of the antibody to the sample as compared to binding of the antibody to a control sample identifies the subject as having a GPC2-positive cancer.

In another embodiment, provided is a method of confirming a diagnosis of a GPC2-positive cancer in a subject by contacting a sample from a subject diagnosed with a GPC2-positive cancer with a GPC2-specific monoclonal antibody disclosed herein; and detecting binding of the antibody to the sample. An increase in binding of the antibody to the sample as compared to binding of the antibody to a control sample confirms the diagnosis of a GPC2-positive cancer in the subject.

In some examples of the disclosed methods, the monoclonal antibody is directly labeled.

In other examples, the methods further include contacting a second antibody that specifically binds the monoclonal antibody with the sample; and detecting the binding of the second antibody. An increase in binding of the second antibody to the sample as compared to binding of the second antibody to a control sample detects a GPC2-positive cancer in the subject or confirms the diagnosis of a GPC2-positive cancer in the subject.

In some cases, the cancer is a neuroblastoma, medulloblastoma, retinoblastoma, acute lymphoblastic leukemia, embryonal rhabdomyosarcoma, alveolar rhabdomyosarcoma, Ewing's sarcoma, desmoplastic small round cell tumor or osteosarcoma.

In some examples, the control sample is a sample from a subject without cancer. In particular examples, the sample is a blood or tissue sample.

In some embodiments of the methods of diagnosis and detection, the antibody that binds (for example specifically binds) GPC2 is directly labeled with a detectable label. In another embodiment, the antibody that binds (for example, specifically binds) GPC2 (the first antibody) is unlabeled and a second antibody or other molecule that can bind the antibody that specifically binds GPC2 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, GPC2 can be assayed in a biological sample by a competition immunoassay utilizing GPC2 protein standards labeled with a detectable substance and an unlabeled antibody that specifically binds GPC2. In this assay, the biological sample, the labeled GPC2 protein standards and the antibody that specifically bind GPC2 are combined and the amount of labeled GPC2 protein standard bound to the unlabeled antibody is determined. The amount of GPC2 in the biological sample is inversely proportional to the amount of labeled GPC2 protein standard bound to the antibody that specifically binds GPC2.

The immunoassays and methods disclosed herein can be used for a number of purposes. In one embodiment, the antibody that specifically binds may be used to detect the production of GPC2 in cells in cell culture. In another embodiment, the antibody can be used to detect the amount of GPC2 in a biological sample, such as a tissue sample, or a blood or serum sample. In some examples, the GPC2 is cell-surface GPC2. In other examples, the GPC2 protein is soluble (e.g. in a cell culture supernatant or in a body fluid sample, such as a blood or serum sample).

In one embodiment, a kit is provided for detecting GPC2 in a biological sample, such as a blood sample or tissue sample. For example, to confirm a cancer diagnosis in a subject, a biopsy can be performed to obtain a tissue sample for histological examination. Kits for detecting a polypeptide can include a monoclonal antibody that specifically binds GPC2, such as any of the monoclonal antibodies disclosed herein. In a further embodiment, the antibody is labeled (for example, with a fluorescent, radioactive, or an enzymatic label).

In one embodiment, a kit includes instructional materials disclosing means of use of an antibody that binds GPC2. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting GPC2 in a biological sample generally includes the steps of contacting the biological sample with an antibody which specifically reacts, under immunologically reactive conditions, to GPC2. The antibody is allowed to specifically bind under immunologically reactive conditions to form an immune complex, and the presence of the immune complex (bound antibody) is detected directly or indirectly.

The antibodies disclosed herein can also be utilized in immunoassays, such as, but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind GPC2, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Isolation and Characterization of High Affinity GPC2-Specific Antibodies GPC2-specific monoclonal antibodies were isolated using mouse hybridoma technology. For immunization, a 50-mer peptide (residues 504-553) corresponding to the C-terminal end of cell surface protein GPC2 was synthesized. An additional cysteine residue was introduced to the N-terminus of the peptide. Therefore, it is believed that monoclonal antibodies (mAbs) raised against this peptide bind the C-terminal end of membrane-bound GPC2. Three C57BL/6 mice were immunized three times and boosted with peptide-KLH conjugate. Spleen cell fusions were conducted with the two best mice. Two antibodies, CT3 and CT5, were isolated among ten clones and isotyped as IgG1κ. The nucleotide and amino acid sequences of the VH and VL domains of CT3 and CT5 are set forth herein as SEQ ID NOs: 1-8. The locations of the CDR sequences in each domain are shown in Tables 1-4 (see Section III above).

Figure 1B:
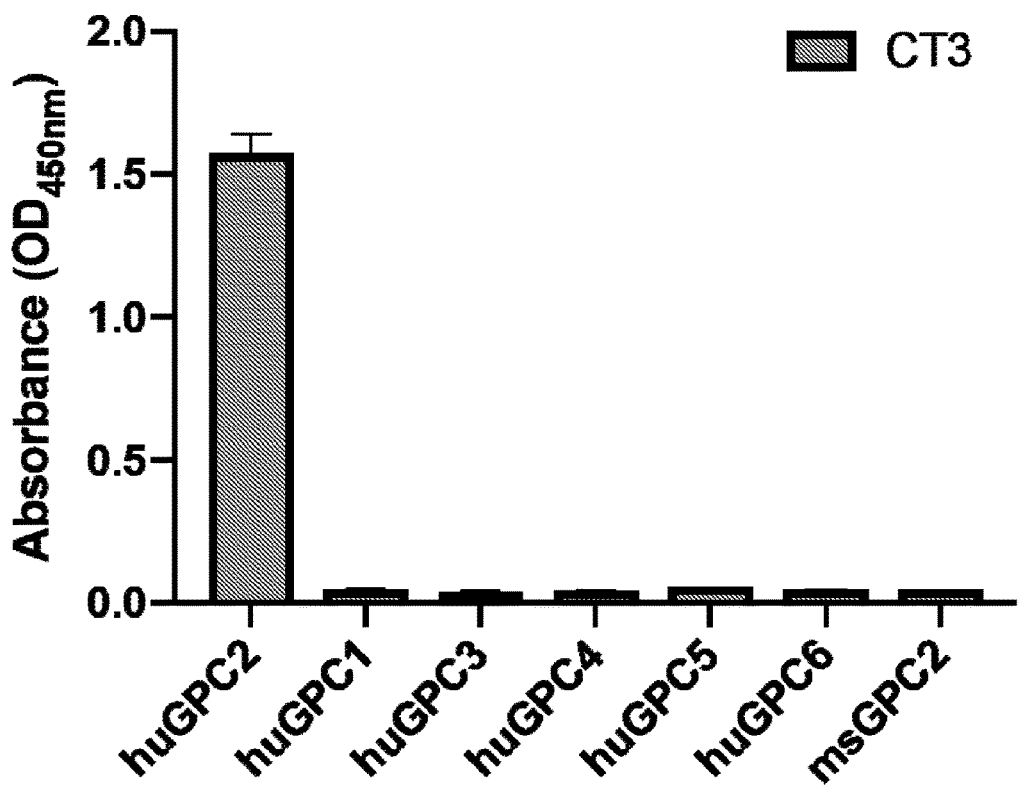
FIG. 1B: ELISA analysis of CT3 binding to human glypican proteins (huGPC1, huGPC2, huGPC3, huGPC4, huGPC5 and huGPC6) and mouse GPC2 (msGPC2). The CT3 antibody specifically binds human GPC2.
Figure 1C:
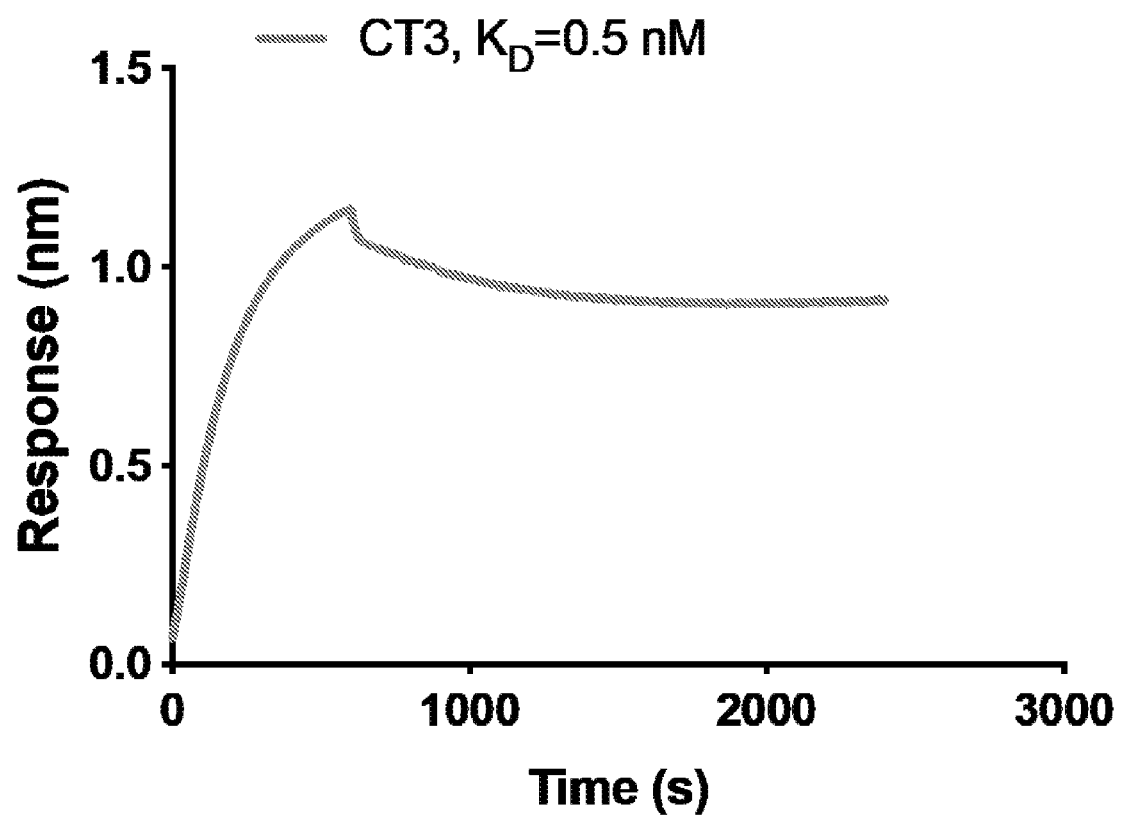
FIG. 1C: Octet kinetic analysis for the interaction between CT3 antibody and human GPC2. CT3 binds GPC2 with high affinity ($K_D$=0.5 nM).

ELISA was performed to determine the binding specificity of both antibodies using recombinant human and/or mouse glypican proteins. As shown in FIG. 1A, CT3 and CT5 only bound human GPC2, not human GPC3, GPC5 or GPC6. CT3 was further evaluated for the capacity to bind human GPC proteins and mouse GPC2. As shown in FIG. 1B, CT3 antibody specifically bound only human GPC2. Octet kinetic analysis was performed to measure binding affinity of CT3 antibody to human GPC2. As shown in FIG. 1C, CT3 binds GPC2 with high affinity ($K_D$=0.5 nM).

The CT3 and CT5 antibodies were further evaluated by flow cytometry to determine whether they can bind cell-surface expressed GPC2. In a first study, binding of CT5 to two GPC2-expressing neuroblastoma cell lines, LAN1 and IMR5, was tested. The results demonstrated that CT5 antibody bound GPC2 on both neuroblastoma cell lines (FIG. 2A). A second study measured binding of CT3 to GPC2-negative A431 cells, GPC2-positive G10 cells (a GPC2-overexpressing A431 cell line), IMR5 cells and F8 cells (a GPC2-overexpressing IMR5 cell line). As shown in FIG. 2B, CT3 antibody specifically recognized GPC2 expressed on the cell surface of all three GPC2-positive cell lines.

Figure 3:
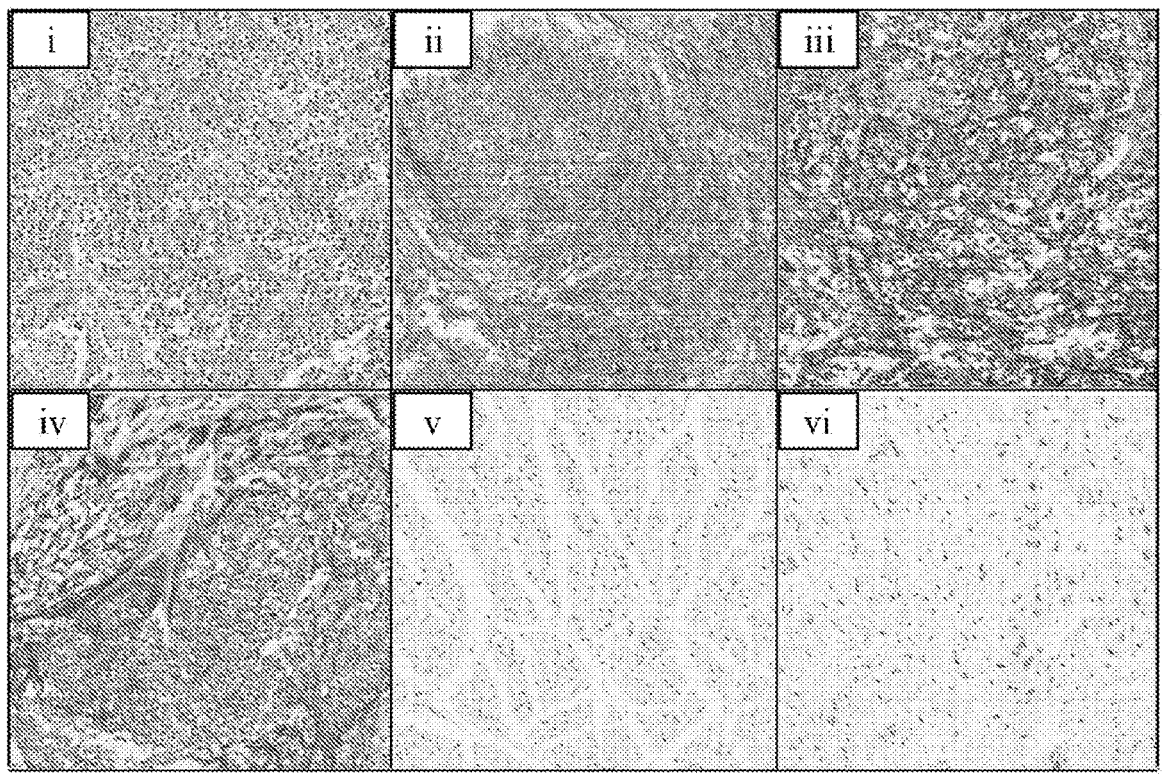
FIG. 3: GPC2 expression in human neuroblastoma tumors. Expression of GPC2 in neuroblastoma tumors (i to iv) and normal nerve (v and vi) tissues as determined by immunohistochemistry. The tissues were labeled with 1 μg/ml CT3 antibody.
Figure 4:
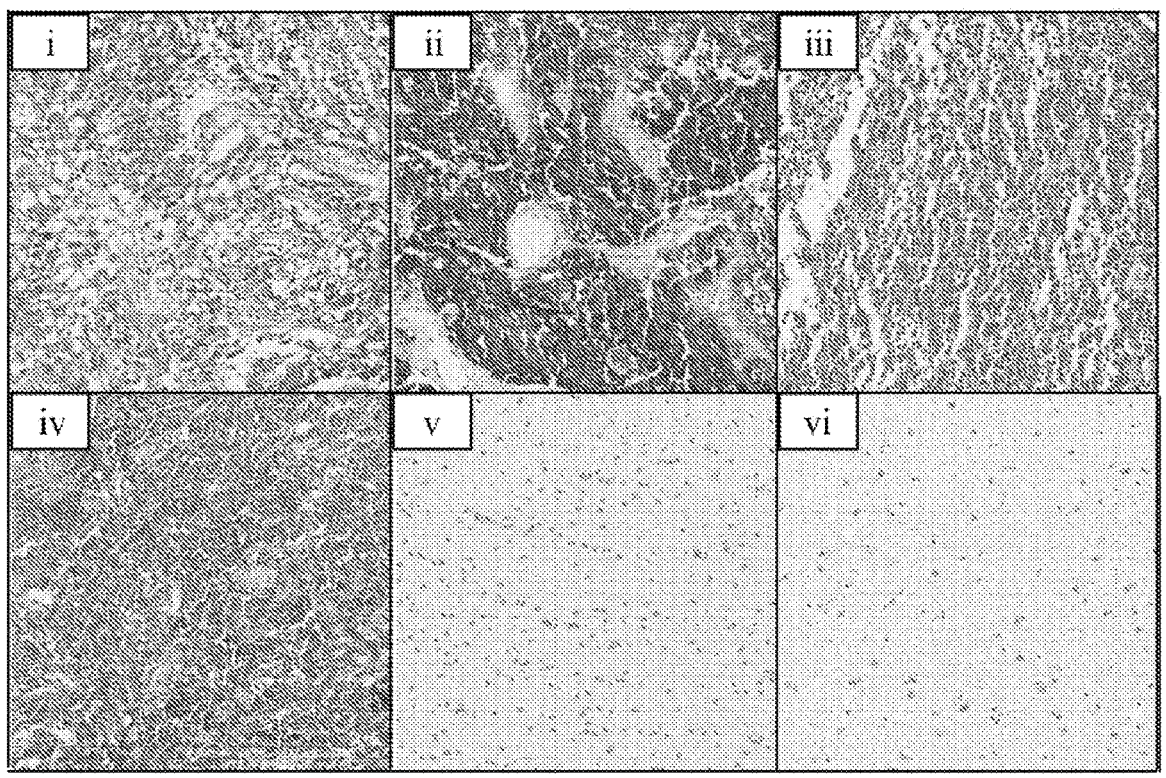
FIG. 4: GPC2 expression in human medulloblastoma tumors. Expression of GPC2 in medulloblastoma tumors (i to iv) and normal brain (v and vi) tissues as determined by immunohistochemistry. The tissues were labeled with 1 μg/ml CT3 antibody.
Figure 5:
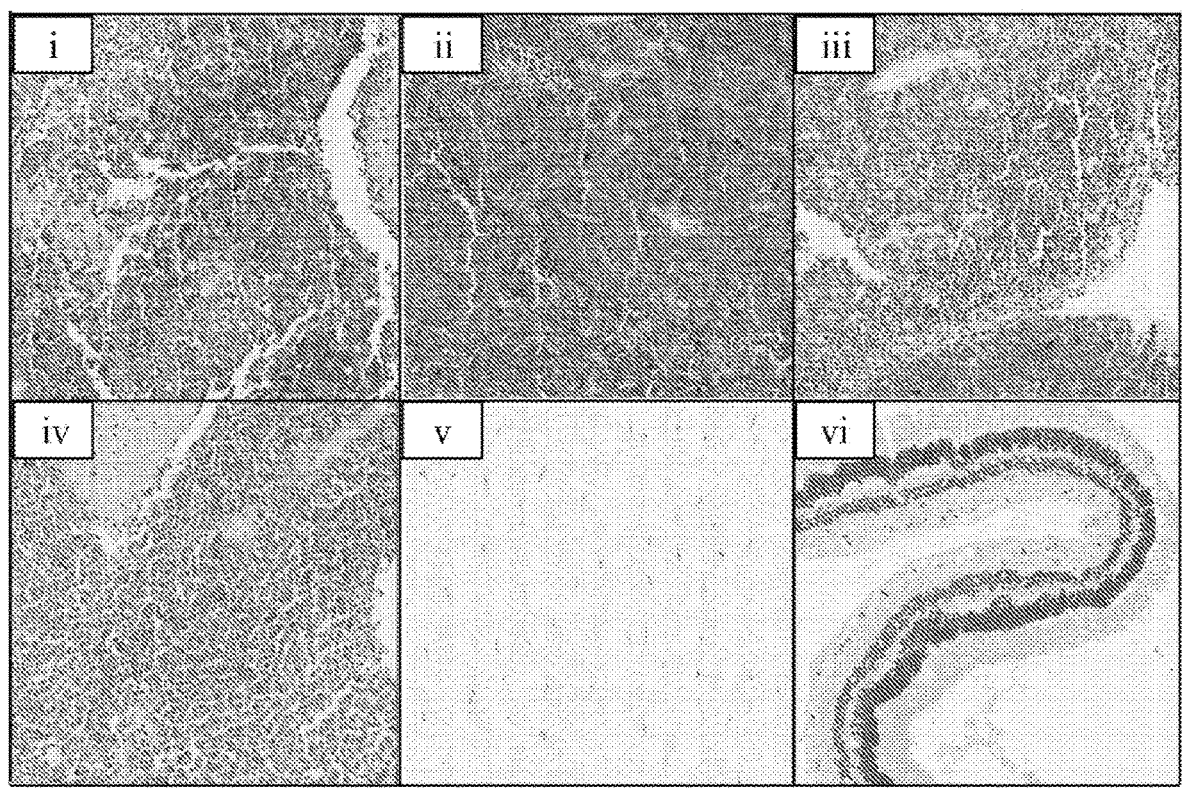
FIG. 5: GPC2 expression in human retinoblastoma tumors. Expression of GPC2 in retinoblastoma tumors (i to iv) and cancer adjacent eye (v and vi) tissues as determined by immunohistochemistry. The tissues were labeled with 1 μg/ml CT3 antibody.
Figure 6:
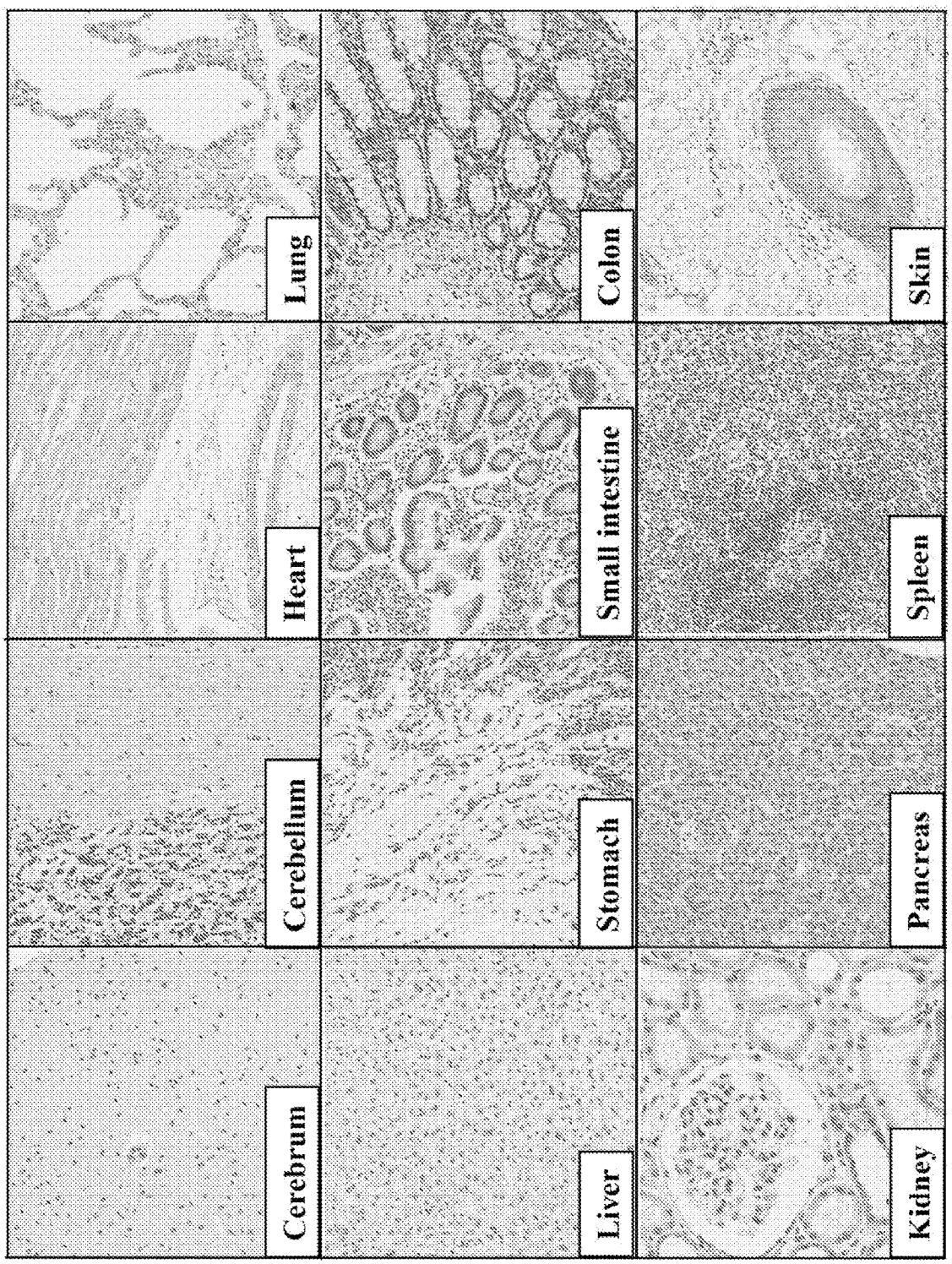
FIG. 6: GPC2 expression in human normal tissues. Expression of GPC2 in human normal tissues including brain, heart, lung, liver, stomach, small intestine, colon, pancreas, spleen, kidney, and skin as determined by immunohistochemistry. The tissues were labeled with 1 μg/ml CT3 antibody. No significant GPC2 staining was detected in any of the normal tissues.

To evaluate the CT3 and CT5 antibodies for immunohistochemical applications, GPC2 expression in human tissues from patients with neuroblastoma or nonmalignant disease was examined using the CT3 antibody. Tissues were labelled with 1 µg/ml CT3 antibody in all experiments. As shown in FIG. 3, GPC2 labeling was apparent in specimens derived from patients with neuroblastoma (i-iv), but essentially undetectable in normal peripheral nerves from patients with nonmalignant disease (v and vi). Neuroblastoma tumor tissues showed strong GPC2 staining in 23 of the 25 cases (92%). GPC2 expression in other pediatric cancers, including medulloblastoma and retinoblastoma, was also evaluated using the CT3 antibody. As shown in FIG. 4, strong GPC2 expression was found in 10 of the 20 cases (50%) of medulloblastoma (i to iv), whereas no staining was detected in normal brain specimens (v and vi). Nearly 80% of retinoblastoma specimens (11 of 14 cases) showed high levels of GPC2 expression as compared with cancer adjacent normal cornea and retina tissues (FIG. 5). To further analyze GPC2 expression in normal human tissues, a FDA-recommended human normal tissue array was probed with the CT3 antibody. No significant GPC2 staining was observed in the normal tissues, including essential organs such as the brain, heart, lung, and liver (FIG. 6). These results suggest a tumor-specific expression of GPC2 and the potential usage of these antibodies as diagnostic tools for neuroblastoma, medulloblastoma, retinoblastoma and other cancers.

Figure 7A:
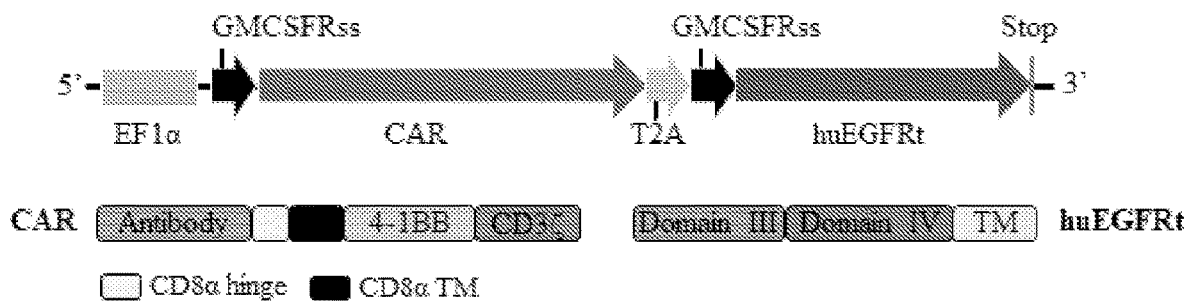
FIGS. 7A-7E: CT3 CAR T cells targeting GPC2 kill neuroblastoma cells.
Figure 7B:
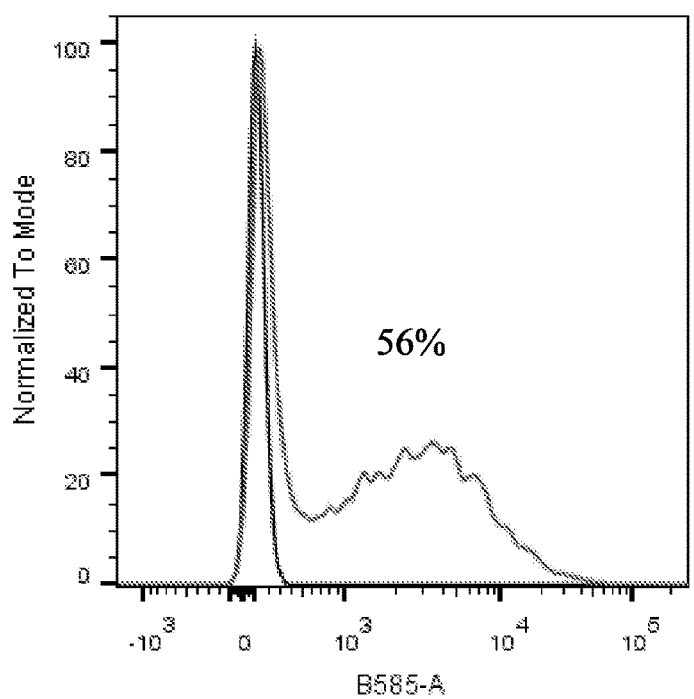
Figure 7C:
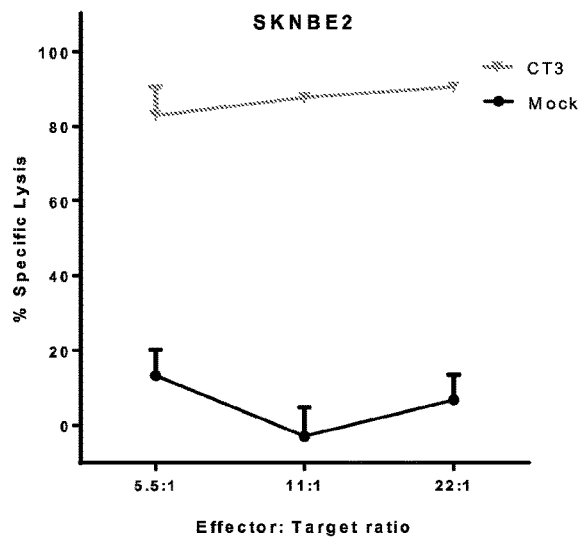
Figure 7D:
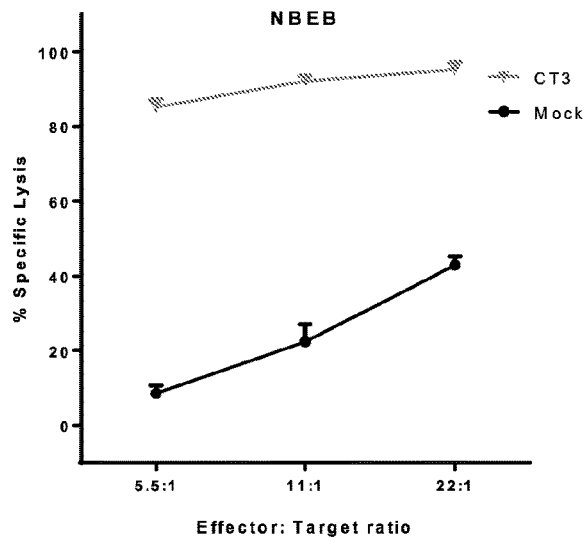
Figure 7E:
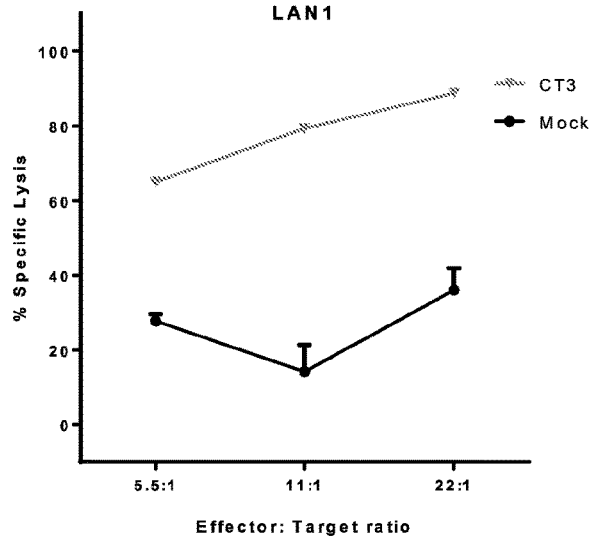

To explore therapeutic applications of the anti-GPC2 mAbs, a chimeric antigen receptor (CAR) was constructed using the single-chain variable fragment (scFv) of CT3 antibody. The CAR nucleic acid construct contained in the 5' to 3' direction: a nucleic acid encoding a first GMCSFR signal sequence; a nucleic acid encoding the CT3 scFv; a nucleic acid encoding the CD8α extracellular hinge region; a nucleic acid encoding the CD8α transmembrane (TM) domain; a nucleic acid encoding the 4-1BB intracellular co-stimulatory domain; a nucleic acid encoding the CD3ζ intracellular signaling domain; a nucleic acid encoding the self-cleaving T2A peptide; a nucleic acid encoding a second GMCSFR signal sequence; and a nucleic acid encoding huEGFRt (FIG. 7A). As shown in FIG. 7B, the transduction efficiency of CT3 CAR in human T cells was 56%. Three GPC2-positive neuroblastoma cell lines (SKNBE2, NBEB and LAN1) were efficiently lysed by the CT3 CAR T cells even at effector:target ratio (E:T) as low as 5.5:1 (FIGS. 7C-7E). By contrast, mock-transduced T cell-mediated killing was minimal in neuroblastoma cells.

Figure 8C:
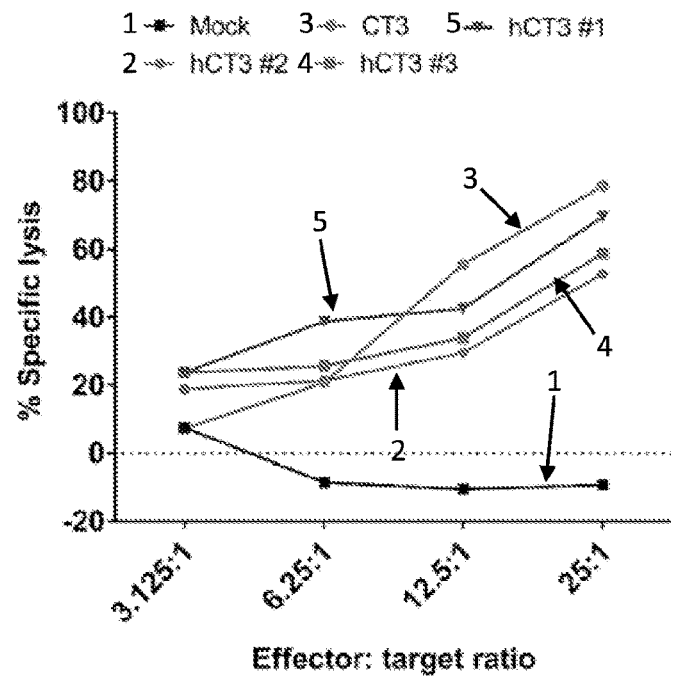
Figure 8D:
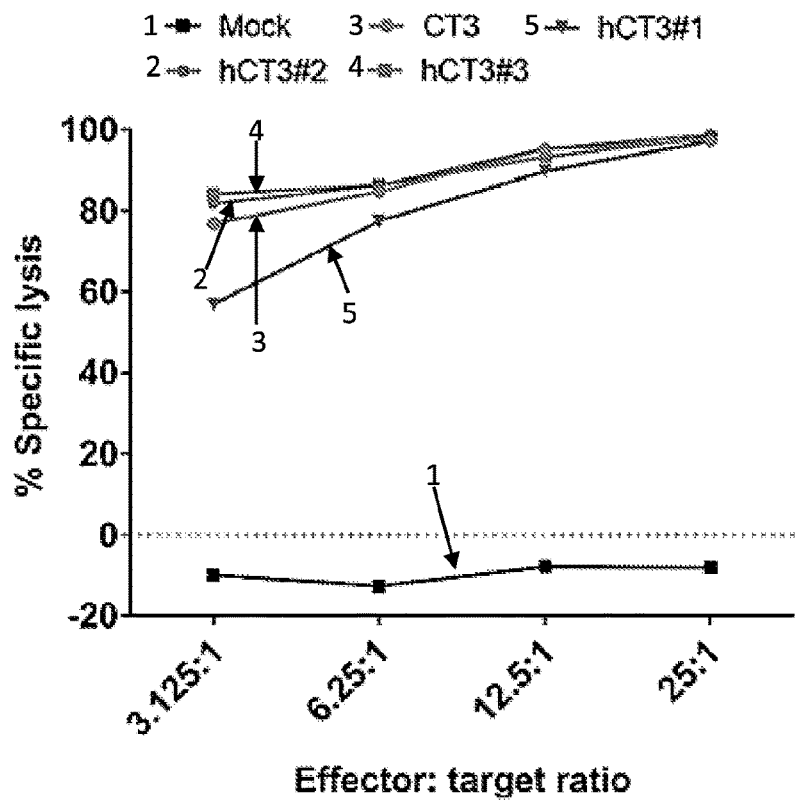

To humanize the CT3 antibody for clinical applications for treating cancer patients, the CT3 CDRs were grafted to human framework sequences. The humanized scFv constructs contained the combined (Kabat/IMGT/Paratome) CDRs of CT3 (see Tables 1 and 2) and human framework sequence. The VH and VL domains were separated by a $(G_3S)_4$ linker. Three clones were generated: hCT3-1 (SEQ ID NO: 10), hCT3-2 (SEQ ID NO: 11) and hCT3-3 (SEQ ID NO: 21). CAR T cells that expressed humanized CT3 antibodies exhibited potent killing activity comparable to the original CT3 based CAR T cells against GPC2 positive tumor cells (G10, IMR5 and F8; FIGS. 8B-8D), but not against GPC2-negative A431 cells (FIG. 8A). The data was not normalized based on their transduction efficiency. If normalized by their transduction efficiency, humanized CT3 derived CAR T cells are more active than the original CT3 CAR T cells because humanized CT3 CARs have a reduced transduction efficiency compared to the original CT3 CAR.

CT3 CAR T cells were also tested in a murine neuroblastoma model. NSG mice were administered 7 million IMR5-luc tumor cells on Day 0. On Day 35, IMR5 tumor-bearing NSG mice were administered mock T cells, or 2.5 million, 5 million, or 10 million CT3 CAR T cells via tail vein injection (FIG. 9A). Tumor burden was monitored by bioluminescent imaging on the day of CART cell infusion, and on Days 3, 11, 19 and 28 post-CART cell infusion (FIG. 9B). CT3 CAR T cells significantly regressed the neuroblastoma tumor growth in mice at higher doses (5 million and 10 million), while the low dose (2.5 million) inhibited the tumor growth. Persistence of GPC2-targeted CAR T cells in vivo was evaluated by measuring CAR vector positive cells in mouse spleens after 2-4 weeks of treatment. Specifically, spleens were harvested at Day 34 for mice treated with 2.5 million CAR T cells, at Day 14 for mice treated with 5 million CAR T cells, and at Day 28 for mice treated with 10 million CAR T cells. As shown in FIG. 10, 41.2%, 26.54% and 21.2% of cells harvested from mice treated with 2.5 million, 5 million and 10 million CAR T cells, respectively, were identified as CAR T cells, indicating that CAR T cells remained present in mouse spleen for at least one month following treatment.

Figure 12C:
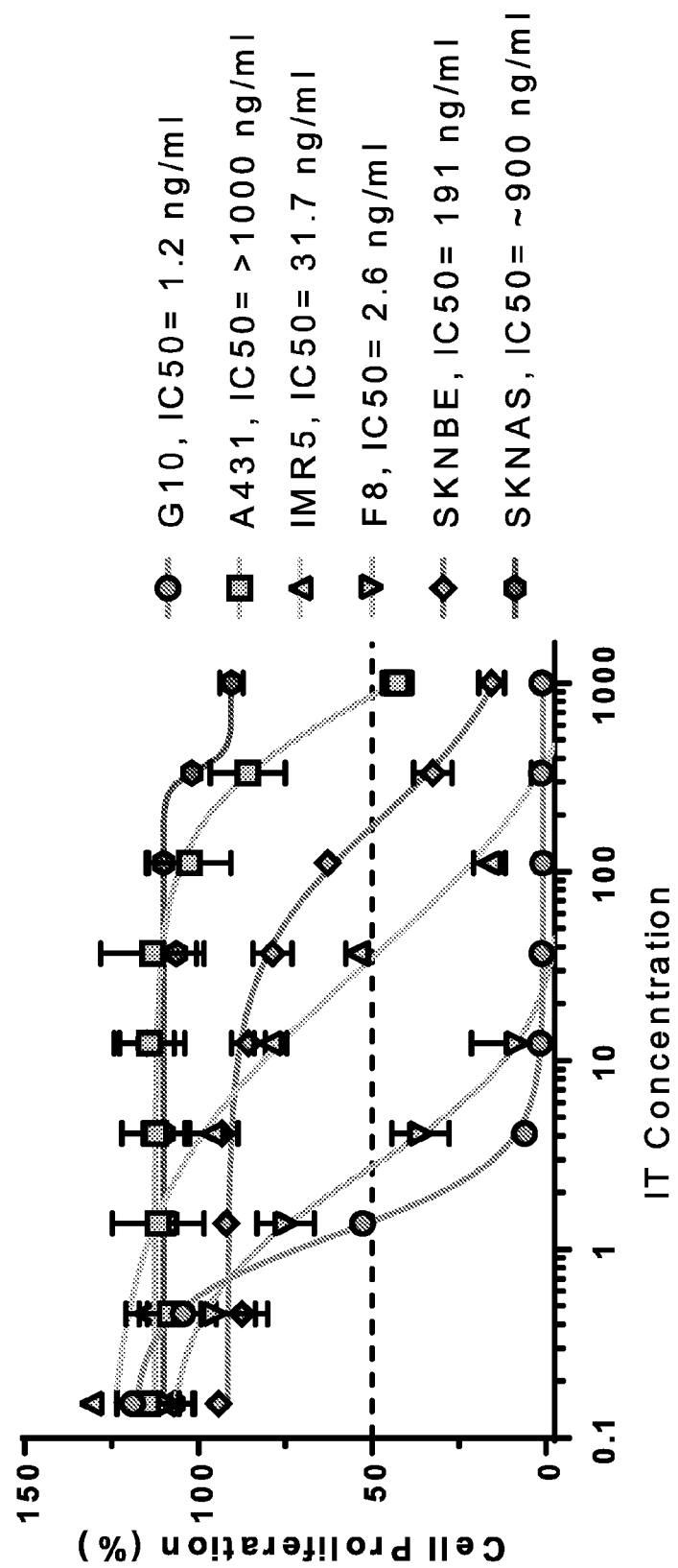

To test the CT3 antibody in the immunotoxin format, CT3 CDRs were grafted to the framework sequence of mouse antibody SS1 (see Chowdhury and Pastan, *Nat Biotechnol* 17:568-572, 1999; Pastan et al., *Nat Rev Cancer* 6:559-565, 2006). The SS1P immunotoxin has been produced and tested in clinical trials for treating mesothelioma, ovarian cancer and pancreatic cancer. The scFv contained the combined (Kabat/IMGT/Paratome) CDRs of CT3, the framework residues of SS1 and a $(G_3S)_4$ linker between the VH and VL domains. The resultant scFv was referred to as sCT3 (SEQ ID NO: 12). An immunotoxin comprising the sCT3 scFv and a truncated *Pseudomonas* exotoxin (PE38) was generated. FIGS. 12A-12B show the production of the sCT3-PE38 immunotoxin. It had a purity and yield similar to SS1P. sCT3-PE38 was tested for its ability to kill GPC2-expressing cells. Cells were incubated with varying concentrations of immunotoxin for three days, then cell number was determined using the WST-8 cell proliferation assay. Cell proliferation in the untreated wells was set to 100% when calculating inhibition of cell proliferation. The sCT3-PE38 immunotoxin killed GPC2-positive tumor cell lines, but not GPC2-negative cells (FIG. 12C). These results demonstrated that cell inhibition caused by sCT3-PE38 is antigen-dependent.

Figure 11A:
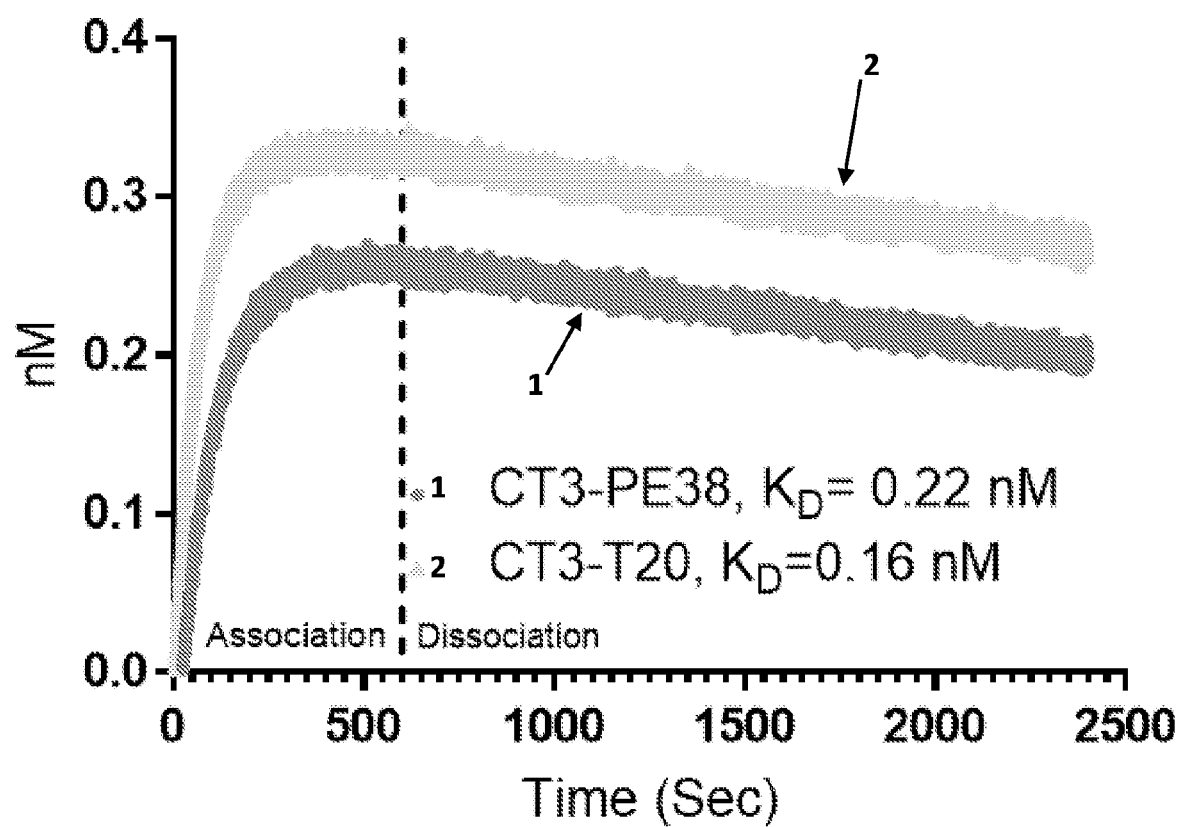
FIGS. 11A-11G: Characterization of the CT3-PE38 and CT3-T20 immunotoxins.
Figure 11B:
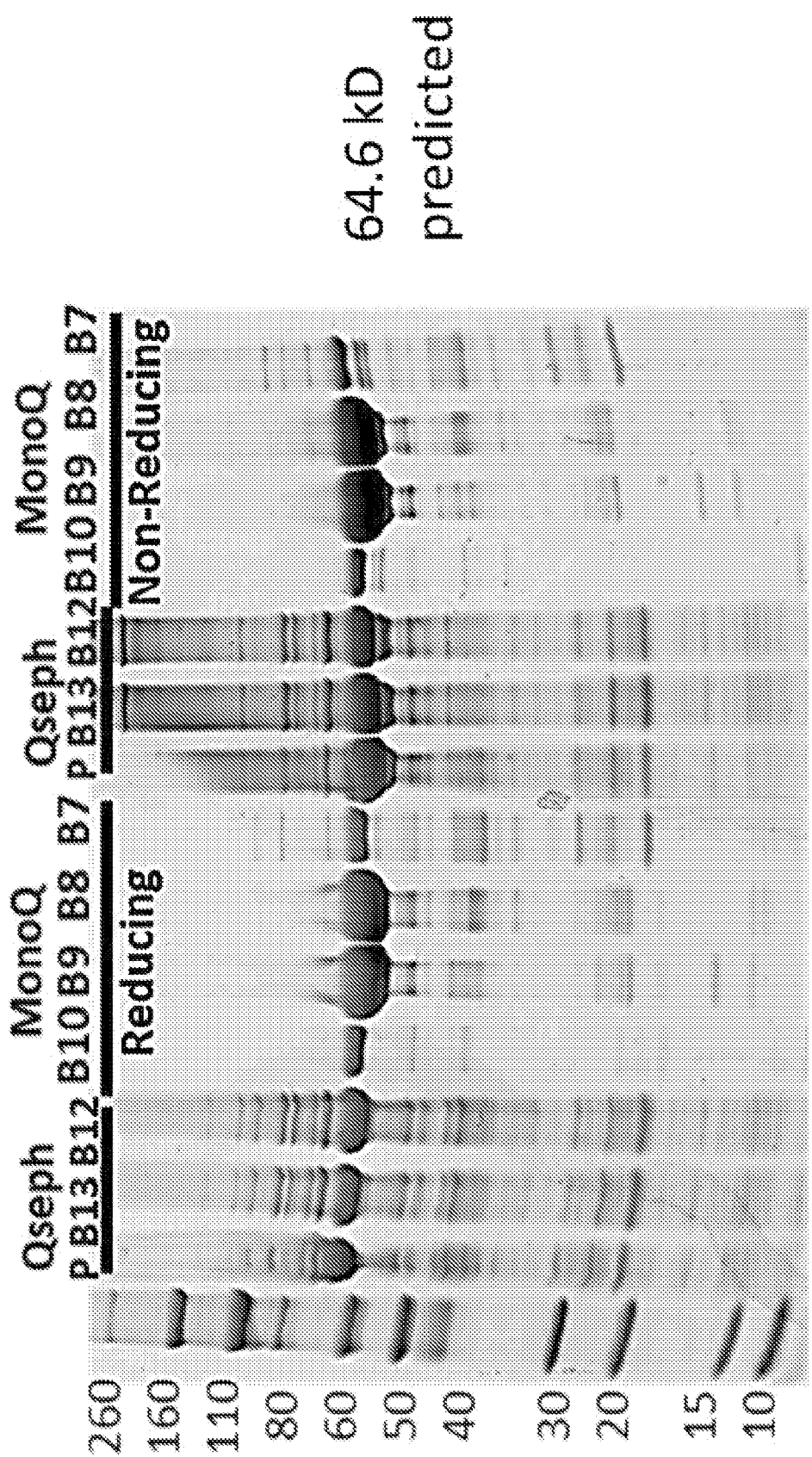
Figure 11C:
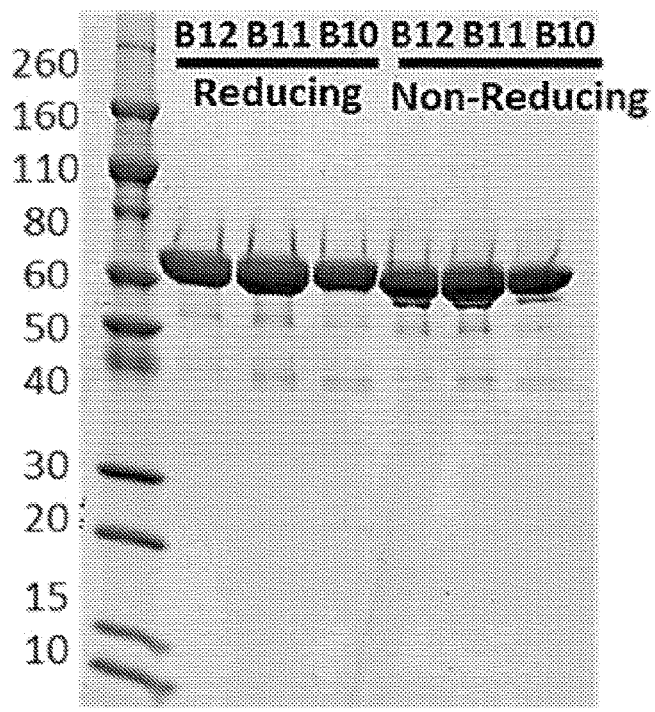
Figure 11D:
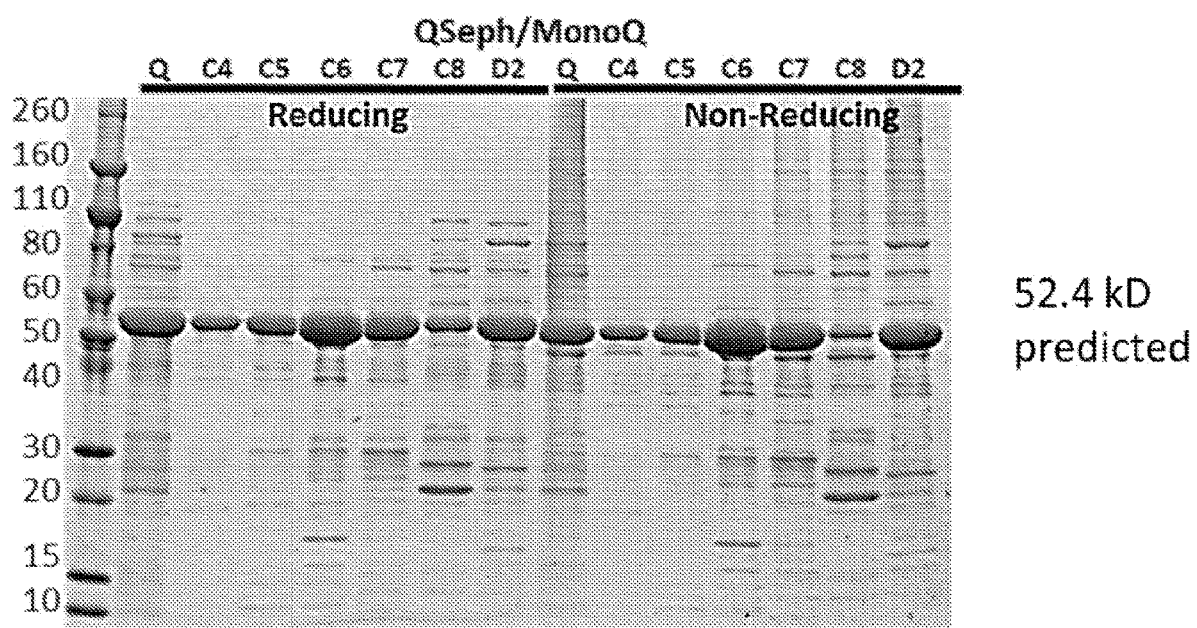
Figure 11E:
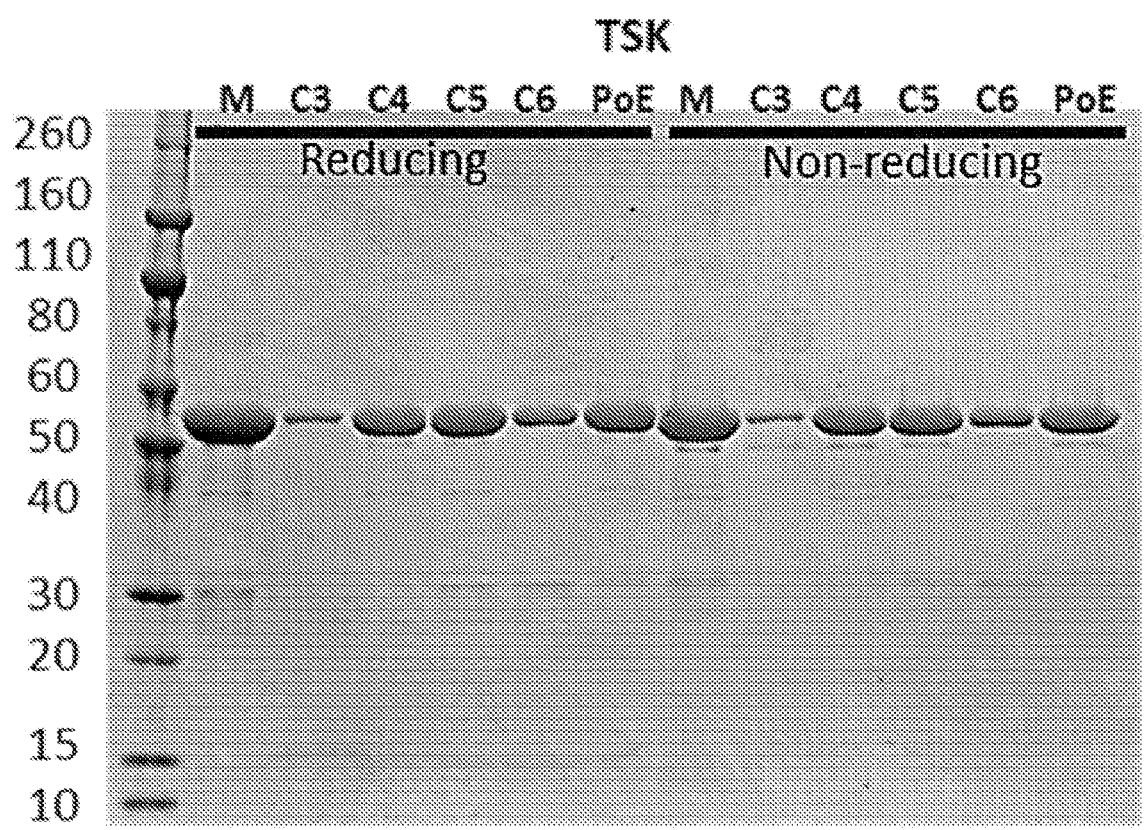
Figure 11F:
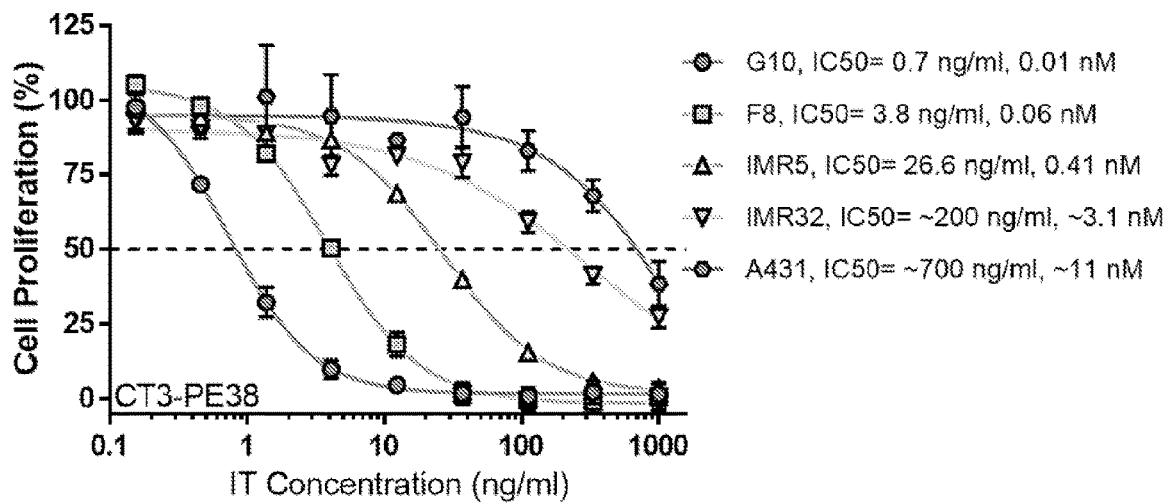
Figure 11G:
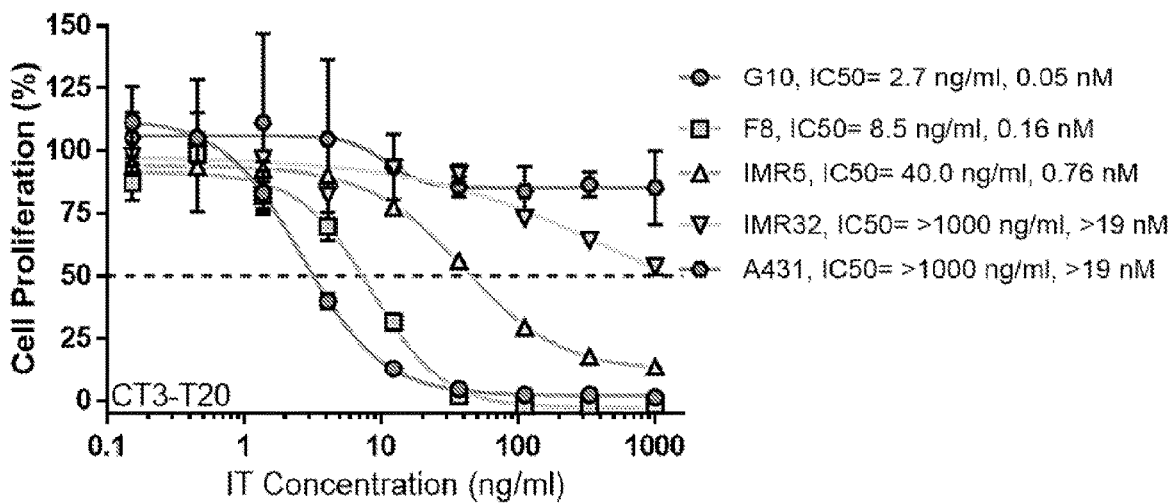

Two additional GPC2-targeted immunotoxins were developed using the CT3 scFv of SEQ ID NO: 9, and either PE38 (SEQ ID NO: 22) or T20 (SEQ ID NO: 23) as the toxin. Octet kinetic analysis was performed to evaluate binding of the GPC2-targeted immunotoxins to human GPC2. Human GPC2-His (250 ng/ml) was loaded onto Ni-NTA biosensor using an Octet Red96e system. Immunotoxins (CT3-PE38 and CT3-T20) were added at 100 nM to determine the affinity of binding. Association occurred for 600 seconds and dissociation occurred for 1800 seconds. Affinity ($K_D$) of CT3-PE38 and CT3-T20 for human GPC2 was determined to be 0.22 nM and 0.16 nM, respectively (FIG. 11A). Due to its high affinity for human GPC2, CT3 is well suited for immunotoxin development. Tris-Glycine 4-20% gels were used to evaluate fraction purities during elution of the CT3-PE38 (FIGS. 11B-11C) and CT3-T20 (FIGS. 11D-11E) immunotoxins. The two immunotoxins were then analyzed for their ability to kill GPC2-expressing cells lines. Cells were incubated with varying concentrations of immunotoxin for three days and cell number was determined using the WST-8 cell proliferation assay. Treatment with CT3-PE38 (FIG. 11F) and CT3-T20 (FIG. 11G) caused inhibition of GPC2-positive G10, F8, and IMR5 cells. In contrast, the antigen-low IMR32 and antigen-negative-A431 cells showed no inhibition.

Next, experiments were conducted to evaluate the GPC2-targeted immunotoxins in animal models of GPC2-expressing tumors. Ten million F8 cells in Matrigel were injected into the right dorsal flank of nude mice. Treatment with PBS, CT3-PE38 (0.25 mg/kg) or CT3-T20 (2 mg/kg) began when the average tumor volume reached 100 mm$^3$. Treatment with either immunotoxin resulted in a significant decrease in tumor volume (p<0.0001) and the immunotoxins were well-tolerated (FIG. 13).

Figure 14A:
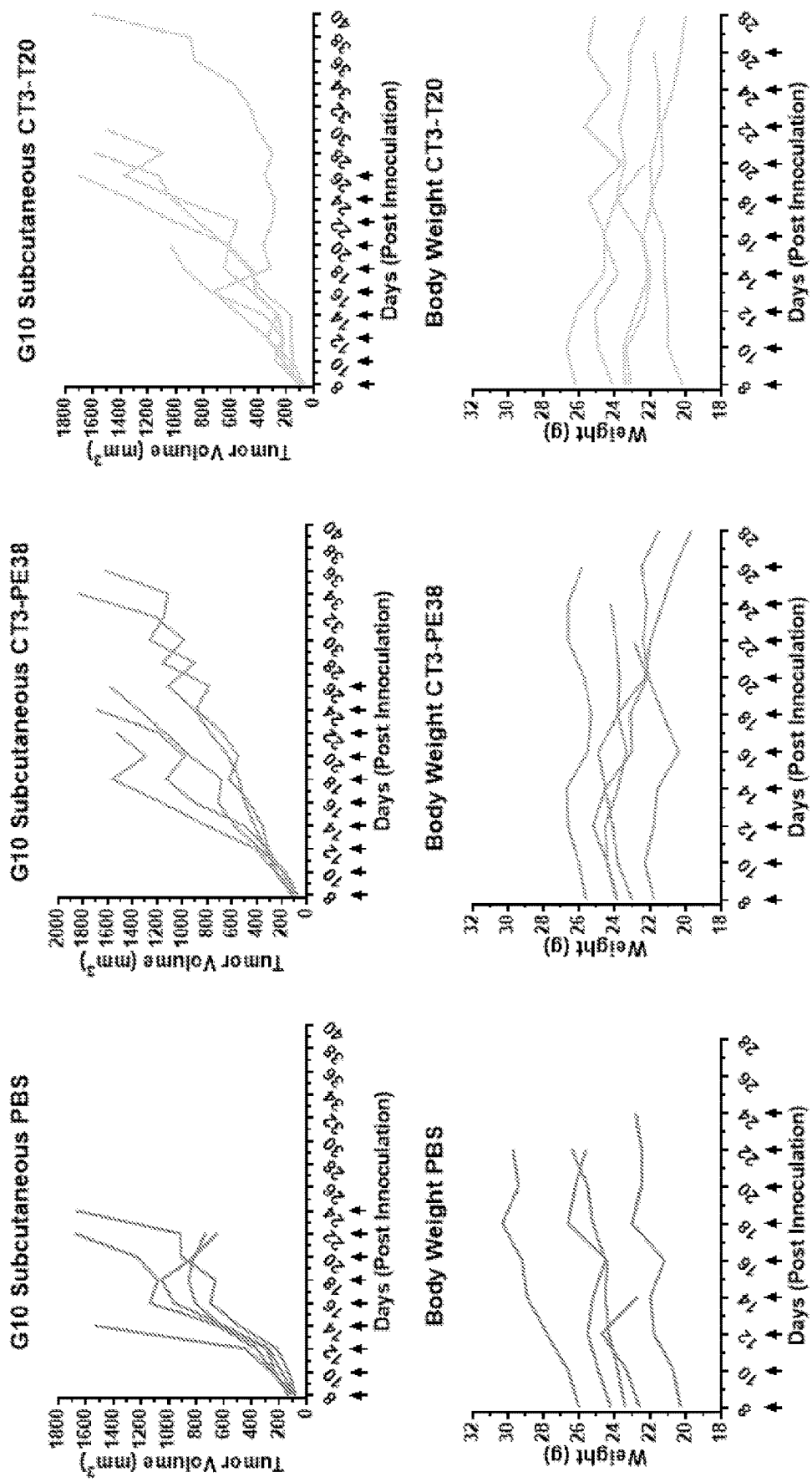
FIGS. 14A-14B: Two million G10 cells in Matrigel were injected into the right dorsal flank of nude mice. Treatment with PBS, CT3-PE38 (0.25 mg/kg) or CT3-T20 (6 mg/kg) began when average tumor volume reached 100 mm$^3$. Arrows indicate treatment days. Tumor volume (FIG. 14A), body weight (FIG. 14A) and survival (FIG. 14B) were assessed. Mice were euthanized when tumors exceeded 1500 mm$^3$ or when tumors began to ulcerate. Average survival for the immunotoxin groups was 28 days compared to 21 days for the PBS-treated group. The Mantel-Cox test was used to determine significance in the Kaplan-Meier survival curve, *$p<0.05$, n=5. CT3 based immunotoxin treatment led to increased survival of nude mice in the G10 subcutaneous xenograft model. CT3-T20 was well tolerated in mice at doses as high as 6 mg/kg.
Figure 14B:
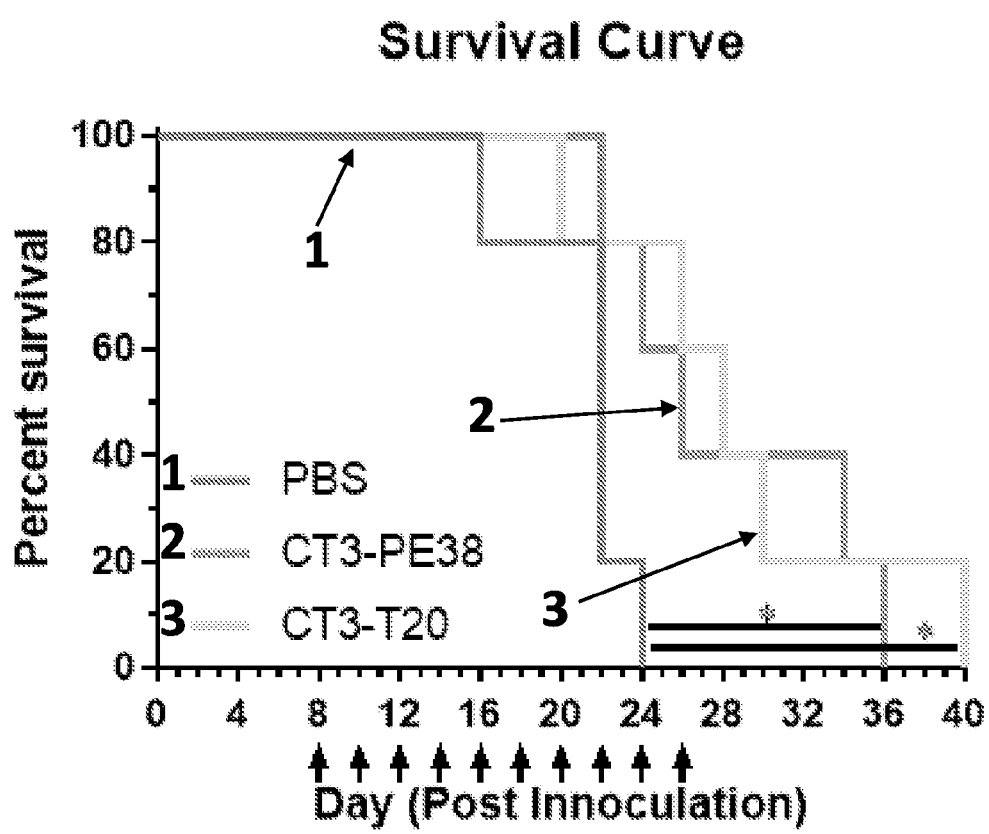

In another study, two million G10 cells in Matrigel were injected into the right dorsal flank of nude mice. Treatment with PBS, CT3-PE38 (0.25 mg/kg) or CT3-T20 (6 mg/kg) began when the average tumor volume reached 100 mm$^3$. Mice were euthanized when tumors exceeded 1500 mm$^3$ or when tumors began to ulcerate. Average survival for the immunotoxin groups was 28 days compared to 21 days for the PBS-treated group. CT3 based immunotoxin treatment led to significantly increased survival (p<0.05) of nude mice in the G10 subcutaneous xenograft model (FIG. 14B). CT3-T20 was well tolerated in mice at doses as high as 6 mg/kg (FIG. 14A).

In a third study, five million IMR5 cells were injected via tail vein into nude mice. Mice were treated with PBS or CT3-T20 (4 mg/kg). Radiance was determined with an IVIS Lumina Series III following a 100 μl injection of xenolight D-luciferin (30 mg/ml) (FIG. 15A). Treatment with CT3-T20 immunotoxin caused reduced tumor burden (FIG. 15B) in the IMR5 metastatic model.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. A monoclonal antibody that binds glypican-2 (GPC2), or an antigen-binding fragment thereof, comprising a variable heavy (VH) domain and a variable light (VL) domain, wherein:
the VH domain comprises the CDR sequences of SEQ ID NO: 2 and the VL domain comprises the CDR sequences of SEQ ID NO: 4; or
the VH domain comprises the CDR sequences of SEQ ID NO: 6 and the VL domain comprises the CDR sequences of SEQ ID NO: 8.

2. The monoclonal antibody or antigen-binding fragment of claim 1,
wherein the CDR sequences are defined using the Kabat, IMGT or Paratome numbering schemes, or a combination of the Kabat, IMGT and Paratome numbering schemes.

3. The monoclonal antibody or antigen-binding fragment of claim 1, wherein:
the VH domain comprises residues 31-35, 50-66 and 99-112 of SEQ ID NO: residues 26-33, 51-58 and 97-112 of SEQ ID NO: 2; residues 26-35, 47-61 and 97-112 of SEQ ID NO: 2; or residues 26-35, 47-66 and 97-112 of SEQ ID NO: 2; and
the VL domain comprises residues 24-33, 49-55 and 88-96 of SEQ ID NO: 4; residues 27-31, 49-51 and 88-96 of SEQ ID NO: 4; residues 27-33, 45-55 and 88-95 of SEQ ID NO: 4; or residues 24-33, 45-55 and 88-96 of SEQ ID NO: 4.

4. The monoclonal antibody or antigen-binding fragment of claim 1, wherein:
the VH domain comprises residues 31-35, 50-68 and 101-109 of SEQ ID NO: 6; residues 26-33, 51-60 and 99-109 of SEQ ID NO: 6; residues 27-35, 47-62 and 99-109 of SEQ ID NO: 6; or residues 26-35, 47-68 and 99-109 of SEQ ID NO: 6; and
the VL domain comprises residues 24-34, 50-56 and 89-96 of SEQ ID NO: 8; residues 27-32, 50-52 and 89-96 of SEQ ID NO: 8; residues 27-34, 46-56 and 89-95 of SEQ ID NO: 8; or residues 27-34, 46-56 and 89-96 of SEQ ID NO: 8.

5. The monoclonal antibody or antigen-binding fragment of claim 1, wherein:
the amino acid sequence of VH domain is at least 95% identical to SEQ ID NO: 2 and/or the amino acid sequence of the VL domain is at least 95% identical to SEQ ID NO: 4; or
the amino acid sequence of VH domain is at least 95% identical to SEQ ID NO: 6 and/or the amino acid sequence of the VL domain is at least 95% identical to SEQ ID NO: 5.

6. The monoclonal antibody or antigen-binding fragment of claim 1, wherein:
the amino acid sequence of the VH domain comprises or consists of SEQ ID NO: 2 and/or the amino acid sequence of the VL domain comprises or consists of SEQ ID NO: 4; or
the amino acid sequence of the VH domain comprises or consists of SEQ ID NO: 6 and/or the amino acid sequence of the VL domain comprises or consists of SEQ ID NO: 8.

7. The monoclonal antibody or antigen-binding fragment of claim 1, which is a humanized monoclonal antibody or antigen-binding fragment.

8. The antigen-binding fragment of claim 1, wherein the antigen-binding fragment is a single chain variable fragment (scFv), an Fab fragment, an Fab' fragment, an F(ab)'$_2$ fragment, or a disulfide stabilized variable fragment (dsFv).

9. The antigen-binding fragment of claim 8, wherein the antigen-binding fragment is a scFv comprising the amino acid sequence of SEQ ID NO: 9, SEQ ID NO: 10, SEQ ID NO: 11, SEQ ID NO: 12 or SEQ ID NO: 21.

10. A chimeric antigen receptor (CAR) comprising the monoclonal antibody or antigen-binding fragment of claim 1.

11. The CAR of claim 10, further comprising a hinge region, a transmembrane domain, a costimulatory signaling moiety, a signaling domain, or any combination thereof.

12. The CAR of claim 11, wherein:
the hinge region comprises a CD8a hinge region;
the transmembrane domain comprises a CD8α transmembrane domain;
the costimulatory signaling moiety comprises a 4-1BB signaling moiety; and/or
the signaling domain comprises a CD3ζ signaling domain.

13. The CAR of claim 10, wherein the antigen-binding fragment is a scFv comprising the amino acid sequence of SEQ ID NO: 9, SEQ ID NO: 10, SEQ ID NO: 11 or SEQ ID NO: 21.

14. An isolated cell expressing the CAR of claim 10.

15. The isolated cell of claim 14, which is a cytotoxic T lymphocyte (CTL).

16. An immunoconjugate comprising the monoclonal antibody or antigen-binding fragment of claim 1 and an effector molecule.

17. The immunoconjugate of claim 16, wherein the effector molecule is a toxin or a detectable label.

18. The immunoconjugate of claim 17, wherein the toxin is *Pseudomonas* exotoxin or a variant thereof.

19. The immunoconjugate of claim 17, wherein the detectable label comprises a fluorophore, an enzyme or a radioisotope.

20. An antibody-drug conjugate (ADC) comprising a drug conjugated to the monoclonal antibody or antigen-binding fragment of claim 1.

21. The ADC of claim 20, wherein the drug is a small molecule.

22. A multi-specific antibody comprising the monoclonal antibody or antigen-binding fragment of claim 1 and at least one additional monoclonal antibody or antigen-binding fragment thereof.

23. The multi-specific antibody of claim 22, which is a bispecific antibody.

24. An antibody-nanoparticle conjugate, comprising a nanoparticle conjugated to the monoclonal antibody or antigen-binding fragment of claim 1.

25. A fusion protein comprising the monoclonal antibody or antigen-binding fragment of claim 1 and a heterologous protein or peptide.

26. The fusion protein of claim 25, wherein the heterologous protein is an Fc protein.

27. A nucleic acid molecule encoding the monoclonal antibody or antigen-binding fragment of claim 1.

28. The nucleic acid molecule of claim 27, operably linked to a promoter.

29. A vector comprising the nucleic acid molecule of claim 27.

30. A nucleic acid molecule encoding a chimeric antigen receptor (CAR), comprising in the 5' to 3' direction:
a nucleic acid encoding a first granulocyte-macrophage colony stimulating factor receptor signal sequence (GMCSFRss);
a nucleic acid encoding the monoclonal antibody or antigen-binding fragment of claim 1;
a nucleic acid encoding an extracellular hinge region;
a nucleic acid encoding a transmembrane domain;
a nucleic acid encoding an intracellular co-stimulatory domain;
a nucleic acid encoding a intracellular signaling domain;
a nucleic acid encoding a self-cleaving 2A peptide;
a nucleic acid encoding a second GMCSFRss; and
a nucleic acid encoding a truncated human epidermal growth factor receptor (huEGFRt).

31. The nucleic acid molecule of claim 30, further comprising a human elongation factor 1α (EF1α) promoter sequence 5' of the nucleic acid encoding the first GMCSFRss.

32. The nucleic acid molecule of claim 30, wherein the antigen-binding fragment is a single-chain variable fragment (scFv).

33. A vector comprising the nucleic acid molecule of claim 30.

34. The vector of claim 33, wherein the vector is a lentiviral vector.

35. An isolated host cell comprising the nucleic acid molecule of claim 30.

36. A composition comprising a pharmaceutically acceptable carrier and the monoclonal antibody or antigen-binding fragment of claim 1.

37. A method of treating a GPC2-positive cancer in a subject, comprising administering to the subject the monoclonal antibody or antigen-binding fragment of claim 1.

38. A method of inhibiting tumor growth or metastasis of a GPC2-positive cancer in a subject, comprising administering to the subject the monoclonal antibody or antigen-binding fragment of claim 1.

39. The method of claim 37, wherein the GPC2-positive cancer is a pediatric cancer.

40. The method of claim 37, wherein the GPC2-positive cancer is a neuroblastoma, medulloblastoma, retinoblastoma, acute lymphoblastic leukemia, embryonal rhabdomyosarcoma, alveolar rhabdomyosarcoma, Ewing's sarcoma, desmoplastic small round cell tumor or osteosarcoma.

41. A method of detecting expression of GPC2 in a sample, comprising:
contacting the sample with the monoclonal antibody or antigen-binding fragment of claim 1; and
detecting binding of the antibody to the sample, thereby detecting expression of GPC2 in the sample.

42. The method of claim 41, wherein the monoclonal antibody or antigen-binding fragment is directly labeled.

43. The method of claim 41, further comprising:
contacting the monoclonal antibody or antigen-binding fragment with a second antibody, and
detecting the binding of the second antibody to the monoclonal antibody or antigen-binding fragment, thereby detecting expression of GPC2 in the sample.

44. The method of claim 41, wherein the sample is obtained from a subject suspected of having a GPC2-positive cancer.

45. The method of claim 41, wherein the sample is a tumor biopsy.

* * * * *